US012738366B2

(12) United States Patent
Mairs et al.

(10) Patent No.: US 12,738,366 B2
(45) Date of Patent: Sep. 15, 2026

(54) CLINICIAN USER INTERFACE

(71) Applicant: INSPIRE MEDICAL SYSTEMS, INC., Golden Valley, MN (US)

(72) Inventors: Nicholas Mairs, Minneapolis, MN (US); Brody Belland, St. Louis Park, MN (US); Kent Lee, Minneapolis, MN (US); John Rondoni, Plymouth, MN (US); Donovan Fellows, Lake Elmo, MN (US); Maxwell P. Lundeen, Minneapolis, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 413 days.

(21) Appl. No.: 18/196,680

(22) Filed: May 12, 2023

(65) Prior Publication Data

US 2023/0368901 A1 Nov. 16, 2023

Related U.S. Application Data

(60) Provisional application No. 63/341,854, filed on May 13, 2022.

(51) Int. Cl.

| | |
|---|---|
| ***G16H 40/20*** | (2018.01) |
| ***G16H 10/20*** | (2018.01) |
| ***G16H 20/30*** | (2018.01) |
| ***G16H 40/67*** | (2018.01) |

(52) U.S. Cl.

CPC ............. *G16H 40/20* (2018.01); *G16H 10/20* (2018.01); *G16H 20/30* (2018.01); *G16H 40/67* (2018.01)

(58) Field of Classification Search

CPC ........ G16H 40/20; G16H 10/20; G16H 20/30; G16H 40/67; G16H 50/70; G16H 10/60

USPC ........................................................ 705/2–3

See application file for complete search history.

(56) References Cited

U.S. PATENT DOCUMENTS

| | | | |
|---|---|---|---|
| 5,832,448 | A | 11/1998 | Brown |
| 7,469,697 | B2 | 12/2008 | Lee et al. |
| 11,089,998 | B2 | 8/2021 | Klee et al. |
| 11,367,023 | B2 | 6/2022 | Levings et al. |

(Continued)

FOREIGN PATENT DOCUMENTS

| | | | |
|---|---|---|---|
| WO | 2022003521 | A1 | 1/2022 |
| WO | 2022006181 | A1 | 1/2022 |

(Continued)

OTHER PUBLICATIONS

Brusie, "Advances in Neurostimulator Technology . . . " posted at sleepreviewmag.com, https://sleepreviewmag.com/sleep-treatments/therapy-devices/neurostimulators/advances-neurostimulator-technology-ease-utilization-sleep-patients, May 10, 2023 (Year: 2023).*

*Primary Examiner* — Joy Chng
(74) *Attorney, Agent, or Firm* — Dicke, Billig & Czaja, PLLC

(57) ABSTRACT

Examples are directed to methods, devices, systems, computer-readable storage medium. An example non-transitory computer-readable storage medium comprises instructions that when executed cause a processing resource to present a graphical user interface (GUI) associated with a clinician portal, the GUI including a plurality of GUI portions that are individually and selectively displayable to present patient data for a plurality of patients based on at least one filter for different classes of the plurality of patients.

20 Claims, 29 Drawing Sheets

(56) References Cited

U.S. PATENT DOCUMENTS

| | | | | |
|---|---|---|---|---|
| 11,419,496 | B2 | 8/2022 | Whiting et al. | |
| 11,501,868 | B2 | 11/2022 | Semen et al. | |
| 11,508,484 | B1 | 11/2022 | Liu et al. | |
| 2011/0061647 | A1* | 3/2011 | Stahmann .............. | A61B 5/285 128/202.16 |
| 2016/0364531 | A1 | 12/2016 | Kamalasan et al. | |
| 2017/0161461 | A1 | 6/2017 | Delangre et al. | |
| 2018/0360392 | A1 | 12/2018 | Stubbs et al. | |
| 2019/0126039 | A1* | 5/2019 | Yoo .................... | A61N 1/36007 |
| 2019/0148025 | A1 | 5/2019 | Stone et al. | |
| 2020/0242566 | A1 | 7/2020 | Agarwal et al. | |
| 2021/0038899 | A1 | 2/2021 | Stubbs et al. | |
| 2021/0338153 | A1 | 11/2021 | Barrera et al. | |
| 2022/0246293 | A1 | 8/2022 | Peake | |
| 2022/0330822 | A1 | 10/2022 | Whiting et al. | |
| 2022/0406420 | A1 | 12/2022 | Wren et al. | |

FOREIGN PATENT DOCUMENTS

| | | | | |
|---|---|---|---|---|
| WO | 2022182756 | A1 | 1/2022 | |
| WO | WO-2022246267 | A1 * | 11/2022 | ............. G16H 40/67 |

* cited by examiner

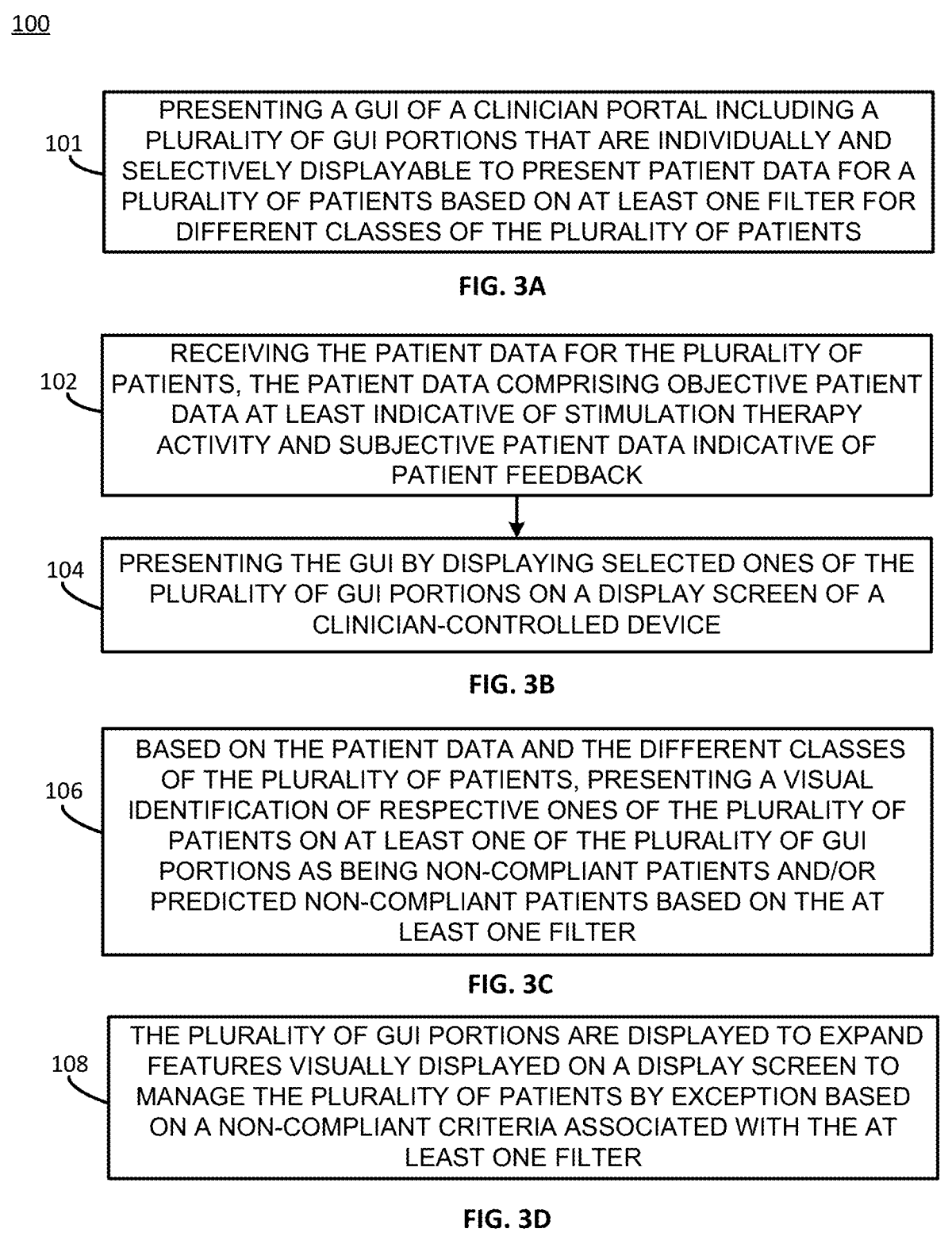

100

101 PRESENTING A GUI OF A CLINICIAN PORTAL INCLUDING A PLURALITY OF GUI PORTIONS THAT ARE INDIVIDUALLY AND SELECTIVELY DISPLAYABLE TO PRESENT PATIENT DATA FOR A PLURALITY OF PATIENTS BASED ON AT LEAST ONE FILTER FOR DIFFERENT CLASSES OF THE PLURALITY OF PATIENTS

FIG. 3A

102 RECEIVING THE PATIENT DATA FOR THE PLURALITY OF PATIENTS, THE PATIENT DATA COMPRISING OBJECTIVE PATIENT DATA AT LEAST INDICATIVE OF STIMULATION THERAPY ACTIVITY AND SUBJECTIVE PATIENT DATA INDICATIVE OF PATIENT FEEDBACK

104 PRESENTING THE GUI BY DISPLAYING SELECTED ONES OF THE PLURALITY OF GUI PORTIONS ON A DISPLAY SCREEN OF A CLINICIAN-CONTROLLED DEVICE

FIG. 3B

106 BASED ON THE PATIENT DATA AND THE DIFFERENT CLASSES OF THE PLURALITY OF PATIENTS, PRESENTING A VISUAL IDENTIFICATION OF RESPECTIVE ONES OF THE PLURALITY OF PATIENTS ON AT LEAST ONE OF THE PLURALITY OF GUI PORTIONS AS BEING NON-COMPLIANT PATIENTS AND/OR PREDICTED NON-COMPLIANT PATIENTS BASED ON THE AT LEAST ONE FILTER

FIG. 3C

108 THE PLURALITY OF GUI PORTIONS ARE DISPLAYED TO EXPAND FEATURES VISUALLY DISPLAYED ON A DISPLAY SCREEN TO MANAGE THE PLURALITY OF PATIENTS BY EXCEPTION BASED ON A NON-COMPLIANT CRITERIA ASSOCIATED WITH THE AT LEAST ONE FILTER

FIG. 3D

Figure 4A:
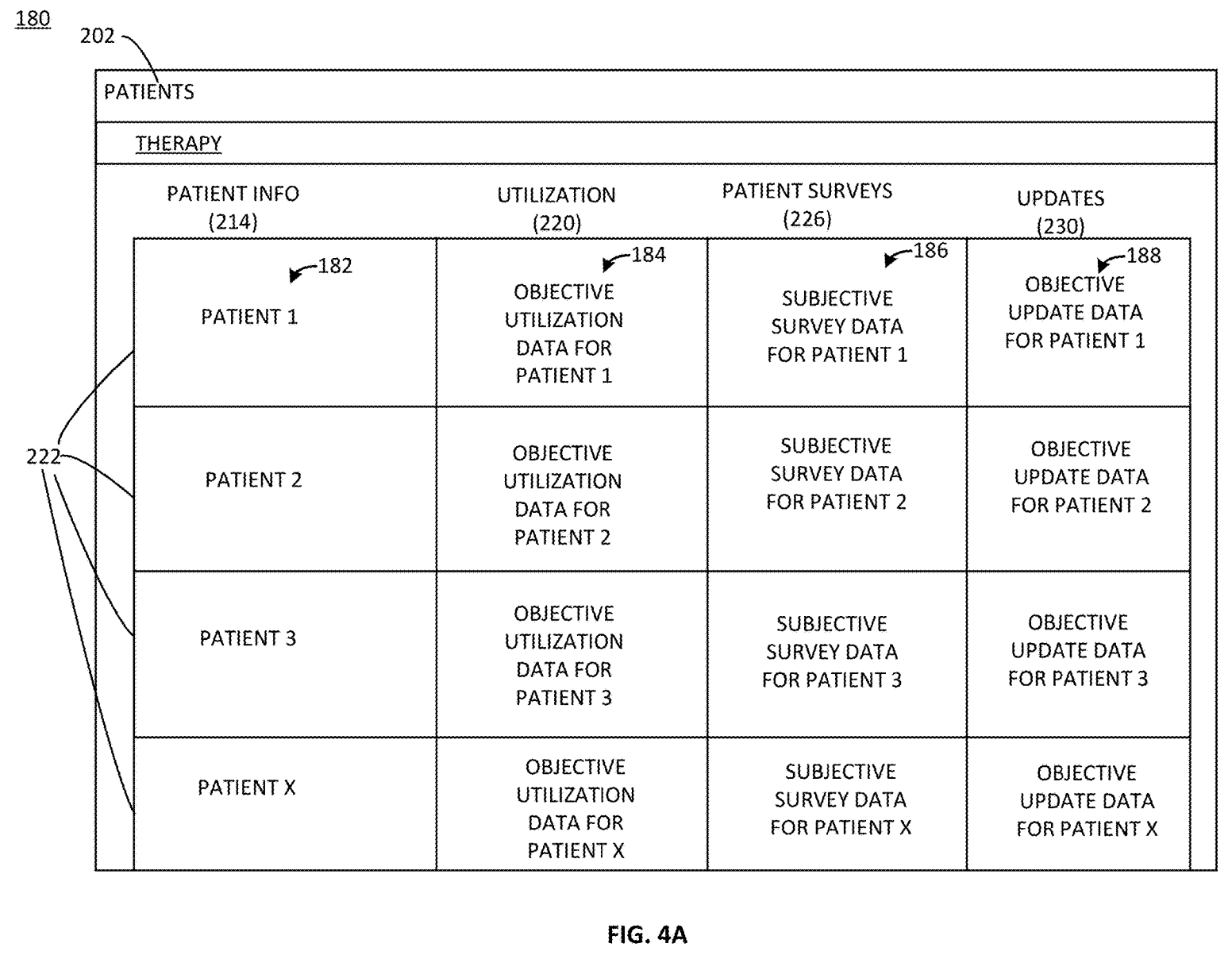

| PATIENT INFO (214) | UTILIZATION (220) | PATIENT SURVEYS (226) | UPDATES (230) |
|---|---|---|---|
| PATIENT 1 | OBJECTIVE UTILIZATION DATA FOR PATIENT 1 | SUBJECTIVE SURVEY DATA FOR PATIENT 1 | OBJECTIVE UPDATE DATA FOR PATIENT 1 |
| PATIENT 2 | OBJECTIVE UTILIZATION DATA FOR PATIENT 2 | SUBJECTIVE SURVEY DATA FOR PATIENT 2 | OBJECTIVE UPDATE DATA FOR PATIENT 2 |
| PATIENT 3 | OBJECTIVE UTILIZATION DATA FOR PATIENT 3 | SUBJECTIVE SURVEY DATA FOR PATIENT 3 | OBJECTIVE UPDATE DATA FOR PATIENT 3 |
| PATIENT X | OBJECTIVE UTILIZATION DATA FOR PATIENT X | SUBJECTIVE SURVEY DATA FOR PATIENT X | OBJECTIVE UPDATE DATA FOR PATIENT X |

Figure 4B:
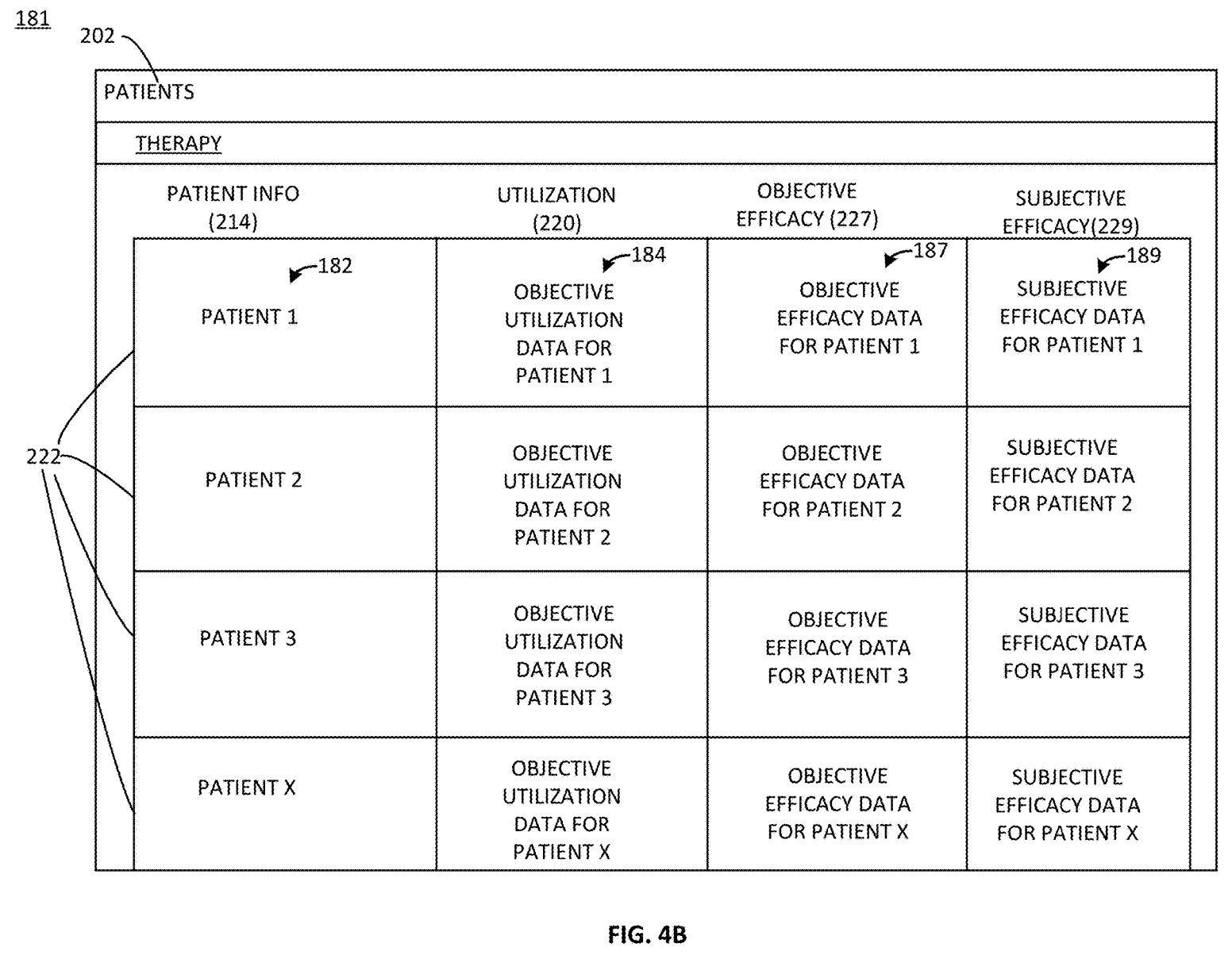

202 PATIENTS

THERAPY

| PATIENT INFO (214) | UTILIZATION (220) | OBJECTIVE EFFICACY (227) | SUBJECTIVE EFFICACY(229) |
|---|---|---|---|
| 182 PATIENT 1 | 184 OBJECTIVE UTILIZATION DATA FOR PATIENT 1 | 187 OBJECTIVE EFFICACY DATA FOR PATIENT 1 | 189 SUBJECTIVE EFFICACY DATA FOR PATIENT 1 |
| PATIENT 2 | OBJECTIVE UTILIZATION DATA FOR PATIENT 2 | OBJECTIVE EFFICACY DATA FOR PATIENT 2 | SUBJECTIVE EFFICACY DATA FOR PATIENT 2 |
| PATIENT 3 | OBJECTIVE UTILIZATION DATA FOR PATIENT 3 | OBJECTIVE EFFICACY DATA FOR PATIENT 3 | SUBJECTIVE EFFICACY DATA FOR PATIENT 3 |
| PATIENT X | OBJECTIVE UTILIZATION DATA FOR PATIENT X | OBJECTIVE EFFICACY DATA FOR PATIENT X | SUBJECTIVE EFFICACY DATA FOR PATIENT X |

222

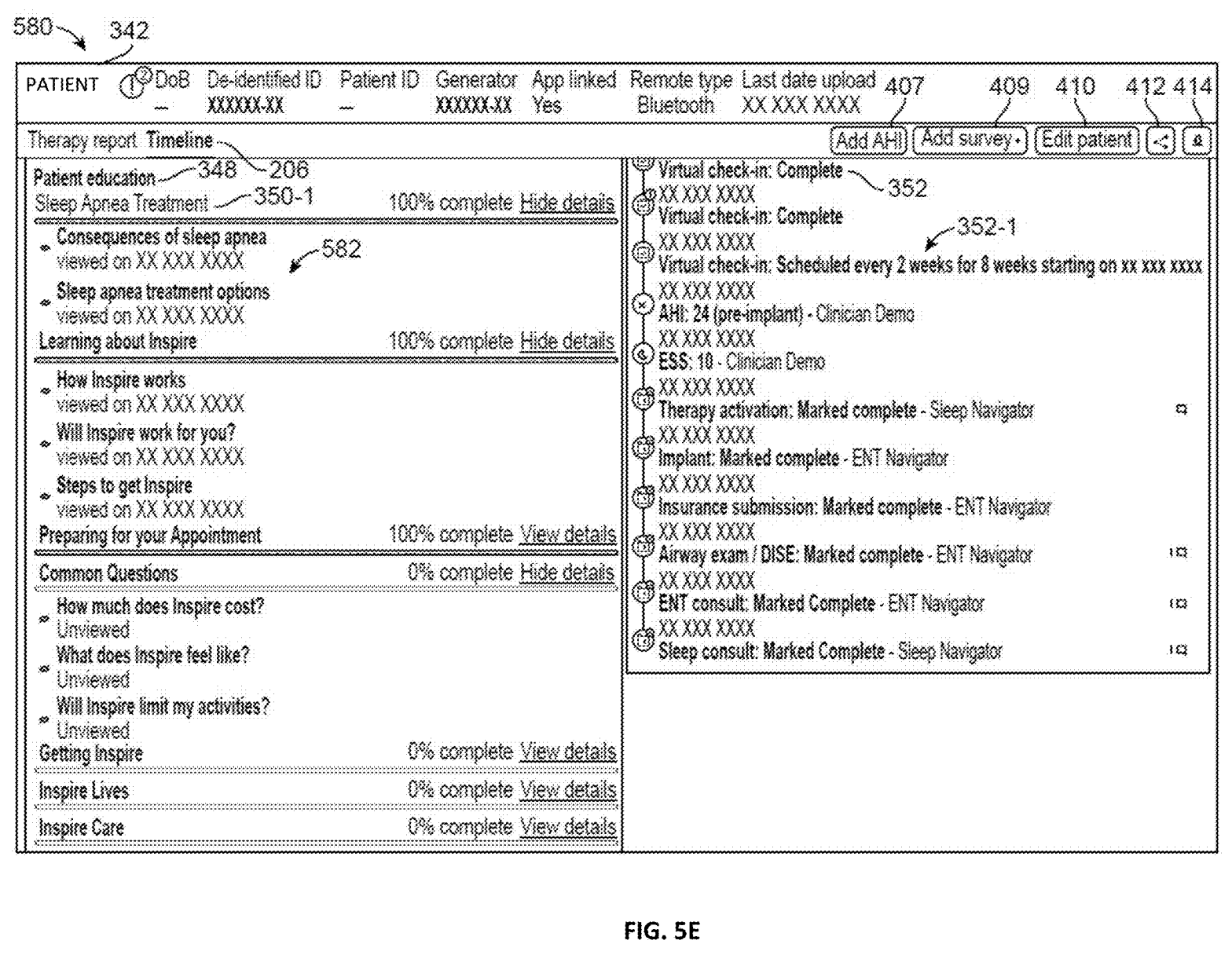

FIG. 4B 580
342
PATIENT DoB De-identified ID Patient ID Generator App linked Remote type Last date upload
— XXXXXX-XX — XXXXXX-XX Yes Bluetooth XX XXX XXXX
407 409 410 412 414
Add AHI Add survey Edit patient
Therapy report Timeline 206
Patient education 348
Sleep Apnea Treatment 350-1
582
Consequences of sleep apnea
viewed on XX XXX XXXX
Sleep apnea treatment options
viewed on XX XXX XXXX
100% complete Hide details
Learning about Inspire 100% complete Hide details
How Inspire works
viewed on XX XXX XXXX
Will Inspire work for you?
viewed on XX XXX XXXX
Steps to get Inspire
viewed on XX XXX XXXX
Preparing for your Appointment 100% complete View details
Common Questions 0% complete Hide details
How much does Inspire cost?
Unviewed
What does Inspire feel like?
Unviewed
Will Inspire limit my activities?
Unviewed
Getting Inspire 0% complete View details
Inspire Lives 0% complete View details
Inspire Care 0% complete View details Virtual check-in: Complete 352
XX XXX XXXX
Virtual check-in: Complete
XX XXX XXXX
Virtual check-in: Scheduled every 2 weeks for 8 weeks starting on xx xxx xxxx 352-1
XX XXX XXXX
AHI: 24 (pre-implant) - Clinician Demo
XX XXX XXXX
ESS: 10 - Clinician Demo
XX XXX XXXX
Therapy activation: Marked complete - Sleep Navigator
XX XXX XXXX
Implant: Marked complete - ENT Navigator
XX XXX XXXX
Insurance submission: Marked complete - ENT Navigator
XX XXX XXXX
Airway exam / DISE: Marked complete - ENT Navigator
XX XXX XXXX
ENT consult: Marked Complete - ENT Navigator
XX XXX XXXX
Sleep consult: Marked Complete - Sleep Navigator

FIG. 5E

CLINICIAN USER INTERFACE

CROSS-REFERENCE TO RELATED APPLICATIONS

This application claims the benefit of the filing date of U.S. Provisional Application Ser. No. 63/341,854, filed May 13, 2022 and entitled "Clinician User Interface," the entire teachings of which are incorporated herein by reference.

BACKGROUND

Some implantable medical devices (IMDs) may communicate with external devices to provide information regarding operation of the IMD within the patient, status of the patient, and the like.

BRIEF DESCRIPTION OF THE DRAWINGS

FIGS. 3A-3D are flow diagrams schematically representing example methods for providing a GUI.

FIGS. 4A-4M are each a diagram schematically representing example GUI portions.

FIGS. 5A-5G are each a diagram schematically representing further example GUI portions which are patient specific.

FIG. 8A is a block diagram schematically representing an example control portion.

FIG. 8B is a diagram schematically illustrating at least some example arrangements of a control portion.

FIG. 9 is a block diagram schematically representing an example user interface.

DETAILED DESCRIPTION

Figure 1:
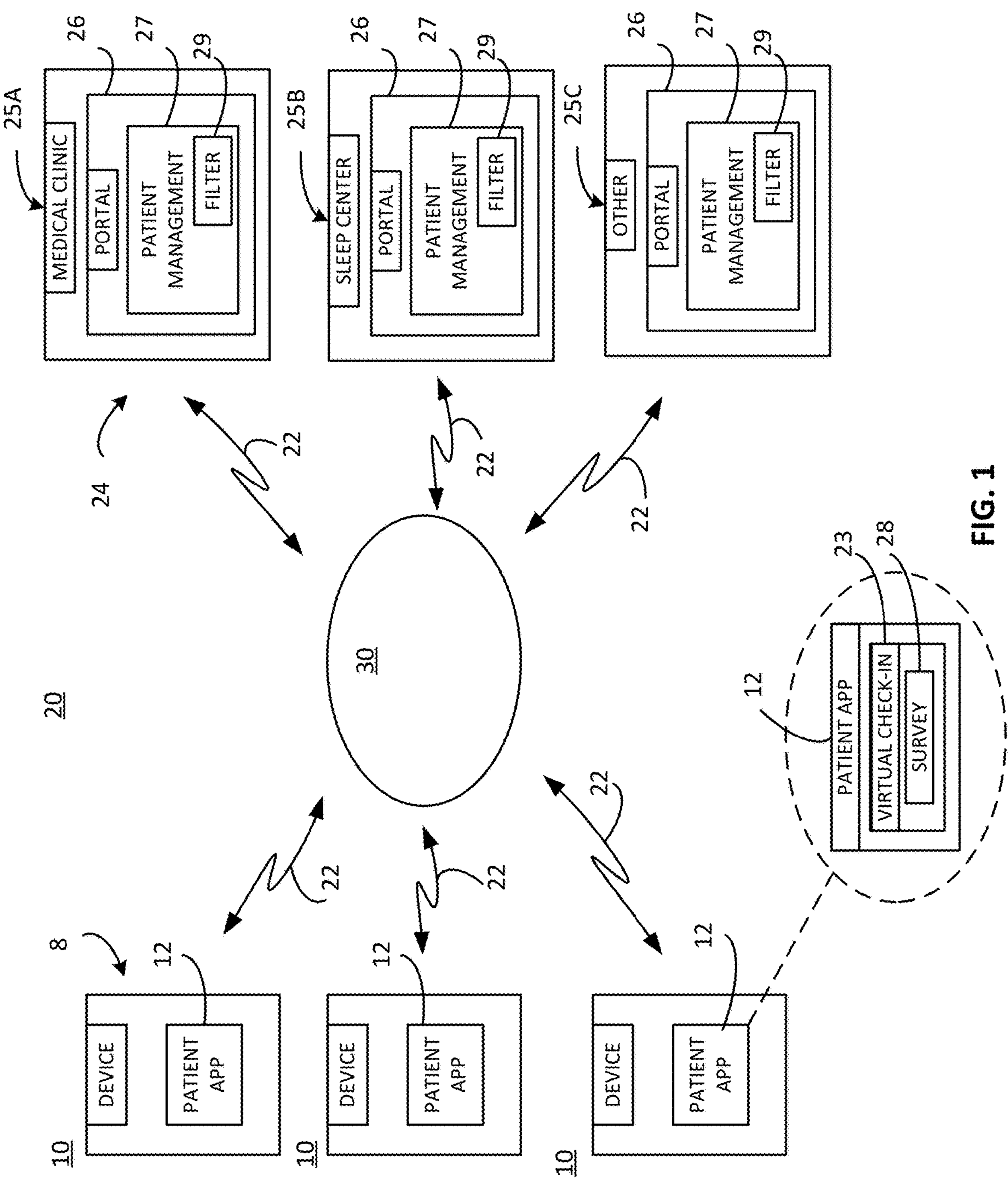
FIGS. 1-2 are diagrams schematically representing example arrangements for providing care, which may include providing a graphical user interface (GUI).

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to integrating information from different sources and/or pathways, etc., and displaying the integrated information on a graphic user interface (GUI) associated with a clinician portal in a manner used to enhance patient compliance with treatment, such as treating sleep disordered breathing (SDB). In some examples, the different sources and/or pathways may comprise patient management information, stimulation therapy information, and/or third party diagnostic/monitoring information. In some examples, integrating such information may enhance efficacy of stimulation therapy and/or of patient management. The third party diagnostic/monitoring information may be obtained from third party diagnostic/monitoring devices, which may communicate with the devices used to perform patient management and/or devices used to perform stimulation therapy. It will be understood that at least some examples use the disparate sources of information as a closed loop feedback to take actions, such as delivering stimulation therapy, performing patient management actions, adjusting monitoring, and the like. Moreover, each action in turn, may produce further feedback communicated to the various devices and therapy, monitoring, management elements hosted among or on such devices.

At least some examples of the present disclosure are directed to facilitating patient care and enhancing patient compliance with the patient care. In some examples, patient compliance (sometimes referred to as "patient adherence"), as used herein, refers to or includes a patient adhering to a treatment plan developed by a clinician. In some examples, non-compliance, by contrast, refers to or includes patient deviations from the treatment plan. A non-compliant patient may include patients which are non-compliant and patients which may (technically) be compliant but which have issues (e.g., provide negative answers to questions in a patient survey, which indicate an issue(s)). These issues may indicate that the patient may become or is predicted to become non-compliant, sometimes referred to herein as "predicted non-compliance" or "predicted or near non-compliant patient." In some examples, a method, device, and/or system to facilitate patient care may comprise arrangements which provide for enhanced communication and workflows between and among: (1) a patient and a clinician regarding the status or progress of their therapy and/or evaluation as a patient candidate; and (2) multiple clinicians (e.g., caregiver entities) forming a patient care team. In some examples, a device manufacturer or service provider may also communicate via such workflows with the care team and/or the patient to facilitate patient care and clinician performance.

At least some examples of the present disclosure provide tools to obtain information about how and when a patient volitionally utilizes stimulation therapy based on the times and days that the patient turns the therapy on and off. The tool may include or be provided on a portal that a clinician may access from a computing device, herein generally referred to as a "clinician portal". This information provides objectivity regarding when a patient starts, pauses, and/or ends nightly therapy, among other information, such as stimulation amplitude changes, and the like. In some examples, this objective patient data may be displayed in a GUI associated with a clinician (viewable by a clinician) together with subjective patient data, such as a patient's subjective experience during nightly stimulation therapy, after such therapy (e.g., during the daytime), and the like. By providing both the objective patient data and the subjective patient data juxtaposed (or otherwise located nearby) in a portion of a GUI, a clinician may enhance their ability to discern relationships between stimulation therapy settings, volitional patient usage (or non-usage) of the stimulation therapy, patient symptoms, and the like. The discernment of such relationships may, in turn, inform decisions resulting in changes to stimulation therapy parameters or resulting in no change to stimulation therapy parameters, among other considerations, such as contacting the patient to increase patient compliance.

Accordingly, via at least some of these examples, a clinician may efficiently and effectively become informed of the status, progress, health of their patients, which may contribute to patient compliance, therapy efficacy, and/or improved patient outcomes. By providing patient stimulation therapy usage information on such a timely basis, the example clinician portals, patient management systems, and/or methods also may facilitate a clinician in making interventions, patient education/encouragement, etc., within a time frame more likely to maintain or improve a trajectory of successful patient compliance, therapy efficacy, and/or patient outcomes. At least some example interventions include adjusting stimulation therapy settings and then application of the modified stimulation settings in (e.g. prior to, during, and/or after) delivery of stimulation therapy to the patient (via the IMD) during a nightly therapy period.

In some such examples, while the example display tools (e.g., available within a GUI portion associated with a clinician portal) may inform the clinician in evaluating stimulation therapy treatment decisions, the example display tools provide the clinician with appropriate autonomy in making medical decisions and/or using their discretion as appropriate regarding adjustment of parameters of the programmer, IMD, etc.

Among other aspects, the example methods, device, and/or systems may comprise a virtual check-in, which is engageable on a mobile application (e.g., app on a display of a computing device) and may provide feedback from the patient to the clinician regarding their usage and experience in using a therapy device. Once received, the patient data may at least partially drive clinician workflows on GUI portions of the clinician portal adapted to facilitate patient care for a plurality of patients. Among other features, these workflows driven via GUIs may facilitate a clinician in quickly identifying patients which warrant faster or deeper attention to help the patient achieve desirable treatment outcomes. Similarly, these workflows (via the GUI portions) facilitate communication and coordination among members (e.g., clinicians) of the care team which represent different types of entities (e.g., sleep study center, medical clinic, surgical facility, etc.) treating the patient.

In some examples, as used herein, the term "clinician" refers to or includes a device therapy technician, sleep study technician, a physician, or other medical worker (e.g., health care professional) suitably experienced to perform (or assist with) the example methods and systems of patient management and patient care of the present disclosure.

In some instances, the example methods, devices, and/or systems may comprise displaying at least some patient data and tools (and/or device management information and tools) via a GUI, such as on a desktop workstation, mobile computing tablet (or other convenient mobile computing device), and the like.

In some examples, methods, devices, and/or systems of patient management may comprise a patient remote control communicating its usage data wirelessly via a patient app (e.g., on a patient communication device) to a clinician portal. Via such arrangements, the clinician may receive patient usage data quickly, and in a manner convenient to the patient because the usage information may be sent from the patient's home, etc. The clinician may receive this usage data after use of the stimulation therapy each night such that, with regard to at least nightly usage metrics, the clinician is kept up to date on a near real-time basis.

This arrangement stands in sharp contrast to some commercially available systems which may communicate usage information from a patient remote control by requiring the patient to bring their patient remote control to a facility at which the usage information may be downloaded, transferred, etc., from the patient remote control to the clinician-controlled device for viewing on a clinician portal. In such commercially available arrangements, a clinician receives updates regarding patient usage considerably less frequently and less conveniently than the nightly usage data available each day in the various examples of the present disclosure.

As used herein, a GUI may comprise a viewable area, which may comprise a single GUI portion occupying an entire viewable area on a display screen of a computing device or multiple GUI portions co-displayed within the entire viewable area. Some of the multiple GUI portions may be similar to each other as to size, shape, location, appearance (e.g., border thickness, color, etc.) and/or content, while some of the GUI portions may be dissimilar to each other as to size, shape, location, accents (e.g., border thickness, color, etc.) and/or content. In general terms, when multiple GUI portions are present in a viewable area of GUI, the portions may be understood as being co-displayed in proximity to each other since the GUI portions are simultaneously present in the same viewable area. In some such examples, at least some (e.g., at least two) of the co-displayed GUI portion may be in close proximity to each other within the viewable area of the GUI, whether they are side-by-side, corner-to-corner in a diagonal relationship, top-to-bottom arrangement, and the like.

In some examples in which the GUI portions or regions within a GUI portion are in close proximity to each other, the GUI portions or regions within a GUI may be referred to as being juxtaposed relative to each other. In some such examples, the GUI portions are arranged relative to each other to draw a user's (e.g., viewer) attention more quickly to the content of the juxtaposed GUI portions. In some examples, a particular GUI portion may be presented to be conspicuously noticeable by size (e.g., larger), by location (e.g., center), by shape (e.g., different shape), and/or other parameters within a viewable area of the GUI. Other GUI portions may have less prominent features to accentuate the prominence of the favored GUI portion. The user may include a clinician or other person monitoring patient outcomes.

In some examples, a user may select a single GUI portion to occupy the entire viewable area of the GUI or substantially the entire viewable area of the GUI.

Whether or not a single GUI portion occupies an entire viewable area (or substantially the entire viewable area), in some examples, any given GUI portion may comprise multiple regions, with some regions (of the same GUI portion) being similar as to size, shape, location, orientation, accents (e.g., border thickness, color, etc.) and/or content, and/or with some regions (of the same GUI portion) of which similar as to size, shape, location, orientation, accents (e.g., border thickness, color, etc.) and/or content. The regions also may be understood as being juxtaposed or co-displayed in proximity to each other since they are simultaneously present in the same viewable area. In some such examples, at least some (e.g., at least two) of the co-displayed GUI portions may be close proximity to each other within the viewable area of the GUI, whether displayed side-by-side, corner-to-corner in a diagonal relationship, top-to-bottom arrangement, and the like.

In some examples, different instances (e.g., different patients) of the same type of content (e.g., utilization) may be arranged within a GUI portion in such close proximity (e.g., juxtaposed) to each other, with the same type of content being arranged within one region of a GUI portion while another type(s) of content may be provided within a different region(s) of the same GUI portion. For instance, one region of the GUI portion may display one or more instances of patient utilization, such as within a column shaped utilization region. The instances of patient utilization may be listed vertically within the column, such as one listing per patient. In some examples, the same GUI portion may comprise a second region that comprises a column shaped patient survey region displayed in close proximity to (e.g., juxtaposed with) the utilization region, such as side-by-side, etc. The patient survey region also may display one or more instances of patient utilization, such as listing them vertically within the column, such as one listing per patient. In some examples, the listing for a particular patient within the utilization region may be displayed (e.g., juxtaposed) side-by-side with a corresponding listing for the same patient within the patient survey region (e.g., column). In some examples, objective patient data (e.g., utilization) may be displayed in a juxtaposed and/or integrated manner with subjective patient data (e.g., patient survey). The co-display of different types of patient data may effectively integrate patient data from different sources in a convenient manner by which the clinician may more quickly form an impression of the compliance of the patient, effectiveness of the therapy, ways in which the patient may be non-compliant, etc. Although the above, and various GUI portions illustrated herein, describes regions of the GUI portions as including columns, examples are not so limited and the regions may be differently shaped.

In some examples, respective regions of the GUI portions may exclusively present objective patient data and other respective regions may exclusively present subjective patient data. In some examples, the region(s) presenting objective patient data are juxtaposed with the region(s) presenting subjectively patient data. In some examples, at least one region may present both objective patient data and subjective patient data. For example, at least one region of a GUI portion may be automatically populated using visual identification of patients of a plurality of patients that exhibit non-compliance and/or a highest degree of non-compliance for a class of non-compliance represented within the respective region (e.g., column).

These examples, and additional examples, are further described in association with at least FIGS. 1-13F.

Figure 2:
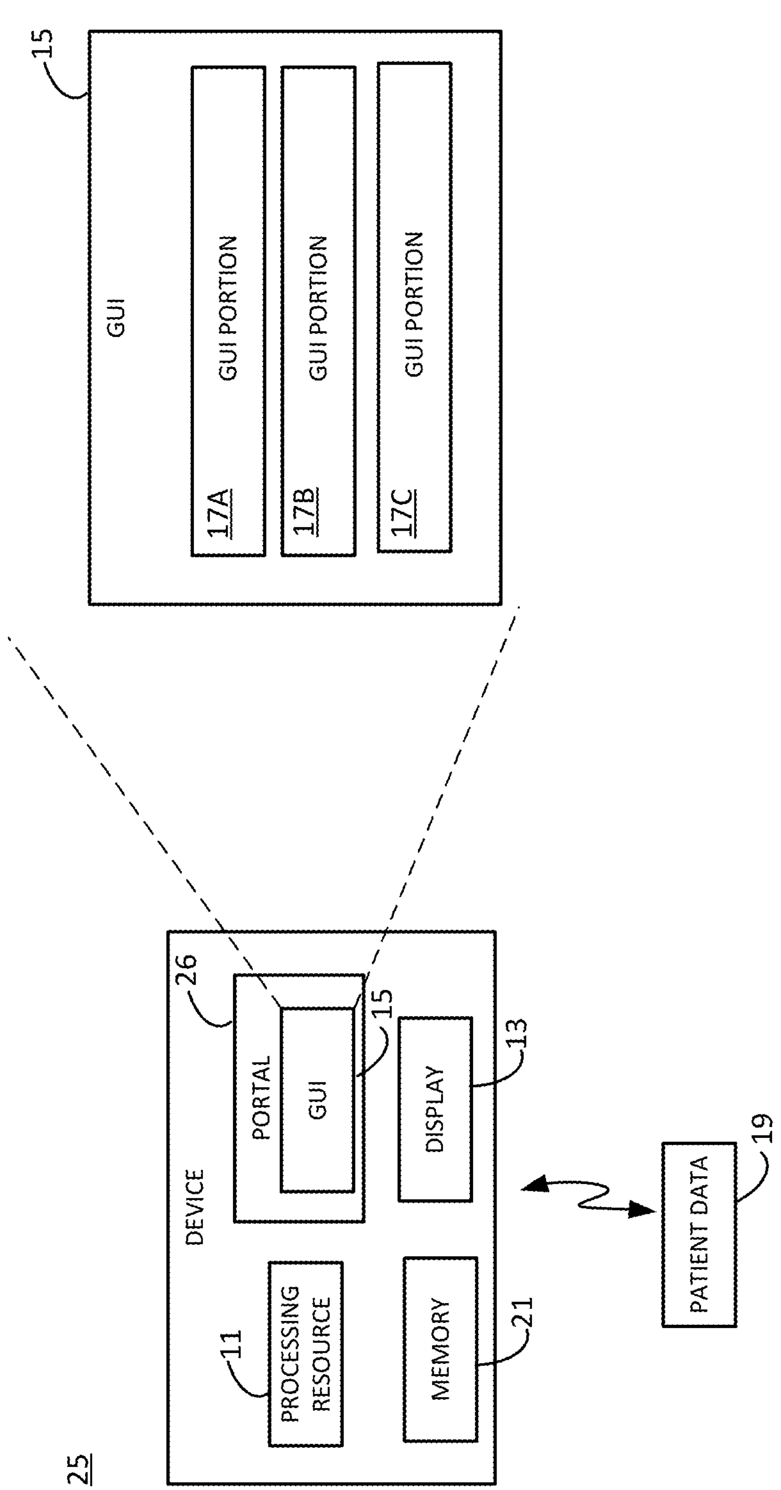

FIGS. 1-2 are diagrams schematically representing example arrangements for providing care, which may include providing a GUI. The arrangements illustrated by FIGS. 1-2 may be used to implement the methods illustrated by any of FIGS. 3A-3D and FIG. 6 and/or to present a GUI as illustrated in connection with any of FIGS. 4A-5G. In some examples, at least some of the example arrangements include IMDs, patient remote controls, third-party diagnostic/monitoring devices, clinician portals, cloud resources and/or other processing resource, patient management systems, patient apps, GUIs, control portions, instructions, workflows, engines, functions, parameters, and/or methods, etc., as described in association with at least FIGS. 7-13F. In some examples, arrangements may be implemented via at least some elements other than those described in association with at least FIGS. 7-13F. The components illustrated by FIGS. 1-2 may be combined in various different combinations and/or may include implementations of one another.

More specifically, FIG. 1 shows an example arrangement 20 used to provide a GUI which may be associated with a clinician portal. The arrangement 20 may comprise an array 8 of computing devices 10, each of which host a patient app 12 relating to patient care. The patient app 12 may provide patient education, enable communication with a caregiver, device servicer, device manufacturer, etc. In some such examples, at least some of the computing devices 10 comprise a mobile computing device, such as a mobile smart phone, tablet, smartwatch, etc., which has a display to provide for operation of, and display of, the patient app 12. As further shown in FIG. 1, in some examples the patient app 12 may comprise a virtual check-in app or function 23 to facilitate a patient checking in with a caregiver, such as a clinician. Among other functions and features, the virtual check-in app 23 may comprise a patient survey 28, which leads the patient through a series of questions (e.g., queries) regarding use of their therapy device, how often they use the device, what may be preventing them from using the device, perceived sleep quality, and the like. At least some answers of the example queries may be used to and/or form patient data, such as patient data 19 illustrated in connection with FIG. 2.

As further shown in FIG. 1, the devices 10 may communicate with other devices, entities, etc., via service provider 30 and a wireless communication protocol as represented by directional arrows 22 and/or wired communication protocol in some examples. It will be understood that service provider 30 may comprise a processing resource and/or other type of computing resource, including programming, provided via the service provider 30 to provide, support, and manage the patient management app 27 for the care entities 25A-25C and the patient app 12 for the patients, which facilitates patient care and facilitates coordinated interaction among the care entities 25A-25C with each other and the respective patients. In some examples, service provider 30 may comprise at least a portion of, and/or an example implementation of, the control portion 920 (FIG. 8B) and user interface 940 (FIG. 9). In some examples, the service provider 30 may comprise a device manufacturer or servicer, or third party contracted by a device manufacturer and which may be implemented by or include a processing resource or service (at least partially) implemented via the cloud. The service provided by the service provider 30 may be hosted via the internet, world wide web, and/or other network communication link.

As further shown in FIG. 1, example arrangement 20 may comprise an array 24 of entities 25A, 25B, 25C, which provide care in some manner to a patient associated with one of the devices 10. The entities 25A, 25B, 25C may work together in at least some aspects to help coordinate care for the patient(s). Each entity may provide a particular form of expertise in patient care, such examples in which one entity 25A comprises a medical clinic, another entity 25B comprises a sleep center, and other entities supportive of patient care 25C. There may greater or fewer than three entities which form at least part of a care team.

Each entity 25A-25C may comprise a processing resource and/or other computing resource, such as workstation or other computing device which may be stationary or mobile, including display screen (e.g., 13 of FIG. 2) to support operation and display of a GUI of clinician portal 26. Among other functions and features, the clinician portal 26 may comprise a patient management app 27 by which the particular care provider (e.g., medical clinic, sleep center, etc.)

may manage patient care among a group of patients, for an individual patient, etc. The patient management app 27 also may enable communicating with other entities (e.g., among 25A-25C) regarding patient care of the patients associated with devices 10. In some examples, the entities 25A-25C may communicate with each other via a cloud computing system (e.g., network communication link, internet, web, etc.) as represented via indicators 22.

At least some features and attributes of the patient management app 27 and/or patient app 12 are further described in association with FIGS. 2-13F, including but not limited to the at least one filter 29.

FIG. 2 illustrates an example device 25. In some examples, the device 25 may be controlled or otherwise accessible by a clinician, and may sometimes be referred to herein generally as "a clinician-controlled device 25". The clinician-controlled device 25 includes a processing resource 11 and display screen 13. In some examples, the clinician-controlled device 25 may form part of an overall system, such as forming part of the arrangement 20 illustrated by FIG. 1 and/or including an example implementation of entities 25A-25C. In some examples, the device 25 further includes a memory 21, as further described herein.

The display screen 13 may be configured with the processing resource 11 to present a GUI 15 associated with a clinician portal 26 including a plurality of GUI portions 17A, 17B, 17C that are individually and selectively displayable to present patient data for a plurality of patients based on at least one filter for different classes of the plurality of patients. In some examples, presenting a GUI or a GUI portion of the GUI, as used herein, may refer to or include populating the GUI portion with at least a portion of the patient data and/or displaying the GUI portion that is populated using the at least portion of the patient data.

In some examples, patient data comprises objective patient data at least indicative of stimulation therapy activity and/or subjective patient data indicative of patient feedback. For example, the display screen 13 and processing resource 11 may present the GUI 15 by displaying at least one of the plurality of GUI portions 17A, 17B, 17C as populated using at least portions of the objective patient data juxtaposed with at least portions of the subjective patient data for at least one of the plurality of the patients, such as one, a subset, or all of the plurality of patients.

In some examples, the processing resource 11 is configured to receive the patient data 19 for the plurality of patients. The patient data 19 may comprise objective patient data at least indicative of stimulation therapy activity and subjective patient data indicative of patient feedback. The patient data 19 may be received from a variety of sources, as further described herein, and may be selectively integrated together by the processing resource 11. The processing resource 11 may be associated with a cloud computing system or other type of networking system in which a plurality of sources may communicate the patient data 19 for aggregation, compilation, etc. In some examples, the various types of patient data 19 may be selectively integrated and/or, in some examples, may be juxtaposed together (e.g., co-displayed in close proximity) on a GUI portion 17A, 17B, 17C. As shown by the close-up of the GUI 15, in some examples, the display screen 13 and processing resource 11 may present the GUI 15 by displaying selective ones of the plurality of GUI portions 17A, 17B, 17C on the display screen 13 of the clinician-controlled device 25, as further described herein.

In some examples, the processing resource 11 may be configured to implement the clinician portal 26 and to selectively integrate the patient data 19 comprising objective and subjective patient data. For example, the display screen 13 and processing resource 11 may present the plurality of GUI portions 17A, 17B, 17C which are populated using at least a portion of the selectively integrated data. In some examples, respective ones of the plurality of GUI portions 17A, 17B, 17C may expand on features (e.g., parameters) associated with the patient data that is populated in and visually displayed by the respective GUI portion 17A, 17B, 17C as compared to others of the GUI portions 17A, 17B, 17C.

As further described herein, the clinician portal 26 may be accessible by the clinician and may provide automatic display of non-compliant patients on respective ones of the GUI portions 17A, 17B, 17C in a manner that is efficient for the clinician to see and to transition between different GUI portions 17A, 17B, 17C to obtain additional information and to interact with the patient(s). For example, the display screen 13 and processing resource 11 may be configured to, based on the patient data and the different classes of the plurality of patients, present a visual identification of respective ones of the plurality of patients on at least one of the plurality of GUI portions 17A, 17B, 17C as being non-compliant patients and/or predicted non-compliant patients based on the at least one filter for different classes of the plurality of patients. In some examples, the plurality of GUI portions 17A, 17B, 17C are displayed to expand features visually displayed on the display screen 13 (e.g., of a clinician-controlled device 25) to manage the plurality of patients by exception based on a non-compliant criteria associated with the at least one filter, as further described herein.

In some examples, the different classes of the plurality of patients may comprise patients with IMDs that are categorized as non-compliant patients and compliant patients. In some examples, classes may be referred to as categories or types. In some examples, as used herein, compliant patients refer to or include patients which are following a treatment plan according to at least one criteria (e.g., threshold, rate, reference) that is associated with the at least one filter. Non-compliant patients, in contrast, may refer to or include patients which are outside of at least one criteria of a treatment plan.

In some examples, as noted above, the different classes of the plurality of patients comprise a plurality of classes of non-compliant patients with IMDs. For example, the plurality of classes of non-compliant patients may comprise: (i) under-utilizing patients which utilize the IMDs or other device at a rate less than a criteria and/or threshold; (ii) under-surveying patients which complete a patient survey outside a threshold time period; and (iii) under-updating patients which provide a therapy-related update status outside a threshold time period; (iv) attention-warranting-answer patients which provide an answer to a patient survey that is indicative of an issue (for the patient and which may be associated with the treatment plan); and/or (v) attention-warranting-titration patients which exhibit certain stimulation amplitude change behavior (e.g., deviation from a stimulation amplitude change reference), as further described herein. In some examples, an attention-warranting answer patient may sometimes provide an answer which is adverse, at least in the context of patient subjective experience.

In some examples, the plurality of GUI portions 17A, 17B, 17C include a main GUI display which automatically presents (e.g., populates and/or displays) a plurality of different (types of) non-compliance classes for each of the plurality of patients and a degree of each of the different non-compliance classes based on the at least one filter for different classes of the plurality of patients and, in some examples, as juxtaposed together. As further described herein, areas, e.g., icons and links, of the main GUI display may be selectable to transition to other respective ones of the GUI portions 17A, 17B, 17C that expand on respective features, such as shown by the GUI portion 180 described in connection with FIG. 4A and/or the GUI portion 200 described in connection with FIG. 4C. As may be appreciated, the GUI 15 of the clinician portal 26 may include GUI portions in addition to those illustrated by FIG. 2 at least some of which may be displayed at different times and/or based on clinician input, at least one filter, and/or sorting.

In some examples, the main GUI display may be a therapy-based display which is automatically displayed by the processing resource 11 when the clinician logs in to the clinician portal 26 and/or in response to the clinician selecting a therapy icon on one of the GUI portions 17A, 17B, 17B. In some examples, an icon, as used herein, refers to or includes a function displayed as a selectable graphic or text on the GUI portion as displayed on a display screen of a computing device, which is selectable to cause an action to occur, such as transitioning to another GUI portion or adding to the GUI portion that displays different and/or expanded information. The classes may include a plurality of different non-compliance classes, such as (but not limited to) the above-described different classes of non-compliant patients including under-utilizing patients, under-surveying patients, under-updating patients, attention-warranting-answer patients, and/or attention-warranting-titration patients (e.g., over or under titrating patients). Each non-compliance class may be associated with a different criteria (e.g., threshold, reference, rate or other criteria) which causes the patient to be visually identified (e.g., flagged) as being non-compliant for the particular non-compliant class (e.g., a category of non-compliance) and/or presenting of the degree of non-compliance. The degree may include a level, a relative level, an absolute numerical value, or other variations, such as an amount of time.

In some examples, respective ones of the plurality of GUI portions 17A, 17B, 17C may be represented (by the processing resource 11 and display screen 13) on other ones of the plurality of GUI portions 17A, 17B, 17C via a corresponding icon, each of which is user selectable to cause transitions between respective ones of the GUI portions 17A, 17B, 17C. For example, as further illustrated by the GUI portion 180 in connection with FIG. 4A and/or the GUI portion 200 in connection with FIG. 4C, the main GUI display may include different icons which are user selectable to cause transition to other GUI portions which expand on features of the patient data.

In some examples, the display screen 13 and processing resource 11 may automatically present visual identification of non-compliant patients of the plurality of patients based on the at least one filter for different classes of the plurality of patients to improve patient compliance, prevent patient non-compliance, and/or mitigate further patient non-compliance and on least a subset of the plurality of GUI portions 17A, 17B, 17C.

In some examples, the objective patient data may comprise stimulation therapy activity reported from an IMD associated with each respective one of the plurality of patients and/or physiologic information reported from an IMD associated with each respective one of the plurality of patients. Specific example objective patient data is further described herein.

In some examples, the subjective patient data may comprise patient feedback such as patient survey data associated with the stimulation therapy activity and/or energy levels (e.g., tired) and/or clinician provided feedback based on interaction with the patient. Specific example subjective patient data is further described herein.

As noted above, the patient data 19 may be received from a variety of sources with are directly or indirectly in communication with the clinician portal 26, such as via the processing resource 11. For example, the processing resource 11 may receive the patient data 19 for each respective patient of the plurality of patients from a plurality of sources selected from: (i) an IMD; (ii) a patient communication device; and (iii) clinician input to the clinician portal 26. Non-limiting examples of a patient communication device include a dedicated patient remote control and a consumer electronic device. In some examples, the patient communication device may comprise a non-dedicated patient remote control. Example consumer electronic device include a smartphone, a tablet, a laptop computer, desktop computer, and a smartwatch, among other devices such as a third party sensor or device.

In some examples, the dedicated patient remote control may be in communication with the IMD and with the consumer electronic device, and the consumer electronic device may communicate with the processing resource 11. For example, the patient remote control may be in communication with, and is to at least receive the objective patient data from, the IMD. In some examples, the consumer electronic device is in communication with, and is to at least receive the objective patient data from, the patient remote control. In some examples, the consumer electronic device (with appropriate security measures) may communicate directly with the IMD.

In some examples, the processing resource 11 is configured to, based on the patient data 19 for a patient of the plurality of patients, perform patient care by determining, within the clinician portal 26, a stimulation therapy to be delivered to upper airway patency-related tissue to treat SDB. For example, the processing resource 11 may communicate the determined stimulation therapy (e.g., from the clinician-controlled device in communication with clinician portal 26 or the processing resource 11 otherwise implementing the clinician portal 26) to an IMD of the patient via: (i) a dedicated patient remote control, and/or (ii) a consumer electronic device. In some examples, communicating the delivered stimulation therapy may include sending a signal to a stimulation element, such as a stimulation element of an IMD, to cause delivery of a stimulation signal to the upper airway patency-related tissue. As further described below, in some examples, the processing resource 11 may include a distributed resource such that the communication via the processing resource 11 may be implemented via: (i) the clinician-controlled device 25, (ii) the dedicated patient remote control, and/or (iii) the consumer electronic device and/or others, such as the service provider 30.

In some examples, the stimulation element (which may form part of a system with the device 25), is configured to deliver the stimulation signal to the patient in response to the signal from the processing resource 11. For example, the stimulation element may placed at or proximate to the upper airway patency-related tissue and delivers the stimulation signal to the upper airway patency-related tissue to treat the patient.

In some examples, the processing resource 11 is configured to, based on the patient data, perform patient care by determining at least one patient management action and communicating the at least one patient management action to a patient communication device. For example, the at least one patient management action may comprise: (i) scheduling a patient office visit; (ii) implementing a communication and/or a command to adjust parameters of stimulation therapy; (iii) implementing a communication and/or a command to adjust parameters of sensing; and/or (iv) implementing a communication and/or a command to adjust parameters of external patient monitoring.

In some examples, the display screen 13 and processing resource 11 are configured to automatically present information which visually identifies non-compliant patients of the plurality of patients based on the at least one filter (e.g., filter 29 of FIG. 1) for different classes of the plurality of patients and an input field for clinician input via at least a portion of the plurality of GUI portions 17A, 17B, 17C. In some examples, an input field, as used herein, refers to or includes an area or region of the GUI portion that is selectable and which the clinician may enter data into.

In some examples, the processing resource 11 may automatically output data to at least one patient communication device in response to clinician input to the input field to drive patient compliance. For example, the output data may include notification of a patient management action and/or notification of determined stimulation therapy, such as those described above.

In some example, at least a subset of the plurality of GUI portions 17A, 17B, 17B may be patient specific, such as illustrated further herein at least in association with FIGS. 5A-5G, and are selectable from at least another subset of the plurality of GUI portions which visually identify the plurality of patients, such as illustrated herein at least in association with FIGS. 4A-4M.

In some examples, the processing resource 11 is configured to identify a patient of the plurality of patients based on at least one filter and in at least one of the plurality of GUI.portions 17A, 17B, 17B, receive a clinician input to the at least one of the plurality of GUI portions 17A, 17B, 17C associated with the patient, and/or, in response, output a communication to a patient communication device associated with the patient. In some examples, the communication is provided prior to the patient being classified as non-compliant or in response to the patient being classified as non-compliant based on the at least one filter, which may be used to improve patient compliance and/or prevent or mitigate non-compliance.

As noted above, the patient data 19 may be received from a plurality of different sources. For the example, the processing resource 11 (or another resource associated with the clinician portal 26) may receive the objective patient data from patient communication devices, the objective patient data comprising sensed physiologic information and/or externally monitored information including: (i) IMD usage; (ii) cardiac information; (iii) respiratory information; (iv) chest motion; (v) oxygen desaturation information; (vi) peripheral arterial information; (vii) blood pressure; (viii) body position; (ix) acoustic information including snoring; (x) sleep information including time spent in bed, total sleep time, start time, stop time, and sleep stage(s); and/or (xi) SDB-related index information, among other information, such as external interruptions (e.g., acoustic noises and/or pressure on the bed indicating external interruptions to sleep).

In some examples, the processing resource 11 (or another resource associated with the clinician portal 26) may receive the subjective patient data from patient communication devices, the: subjective patient data comprising patient survey information including: (i) IMD usage; (ii) comfort levels; (iii) usage hindrances; (iv) device visible indicators; (v) snoring levels; and/or (vi) energy levels, among other information, such as external interruptions for sleep.

Examples are not limited to the above described sources of patient data and may include other sources. For example, the patient data 19 may further comprise patient management information input to the clinician portal 26 via clinician input to at least one of the plurality of GUI portions 17A, 17B, 17C. Other examples may include patient data from external monitoring circuitry, as further described herein.

While FIG. 2 shows a clinician-controlled device 25 that includes the display screen 13, in some examples, an arrangement may include the processing resource 11 and memory 21 which stores at least some of the instructions and patient data, and the processing resource 11 may execute the instructions to implement any of the above described examples, including providing the GUI display(s) and other actions. In some examples, the processing resource 11 and memory 21 may form part of the same device, such as the clinician-controlled device 25. In some examples, the processing resource 11 and memory 21 may form part of different devices, such as distributed resources of a cloud computing system and/or other network-type system having distributed resources. In some examples, the arrangement or system may further include the display screen 13 to provide the display of the GUI 15 and/or the stimulation element to deliver stimulation to a patient, as described above.

Some examples are directed to the instructions executable by the processing resource 11. The instructions may be downloadable to the memory 21 or otherwise stored by memory remotely located from the clinician-controlled device 25 and provided to the clinician-controlled device 25 for storing locally and for executing to implement the clinician portal 26. In some examples, the instructions are executable by the processing resource 11 to implement any of the above-described GUI displays and/or other implementations as described by FIG. 2.

In some examples, the device 25 of FIG. 2 may form part of an arrangement deployable in a method or as a system, to solicit, manage, sort, and communicate patient information to facilitate patient care, such as the arrangement 20 illustrated by FIG. 1.

FIGS. 3A-3D are flow diagrams schematically representing example methods for providing a GUI. The method(s) may be used to present a GUI, such as the GUI portions and regions, as described above and as further illustrated in connection with FIGS. 4A-5G, and/or may be implemented by the arrangement 20 and/or device 25 as described above in connection with any of FIGS. 1-2. In some examples, the method 100 may be implemented using at least some of the example arrangements including IMDs, patient remote controls, third-party diagnostic/monitoring devices, clinician portals, cloud resources and/or other processing resource, patient management systems, patient apps, GUIs, control portions, instructions, workflows, engines, functions, parameters, and/or methods, etc., as described in association with at least FIGS. 7-13F. In some examples, method 100 may be implemented via at least some elements other than those described in association with at least FIGS. 7-13F. The flow diagrams illustrated by FIGS. 3A-3D may be combined in various different combinations and/or may include implementations of one another.

As shown at 101 in FIG. 3A, the method 100 comprises presenting, using a processing resource, a GUI associated with a clinician portal including a plurality of GUI portions that are individually and selectively displayable to present patient data for a plurality of patients based on at least one filter for different classes of the plurality of patients.

As shown at 102 in FIG. 3B, in some examples, the method 100 comprises receiving, via the processing resource, the patient data for the plurality of patients, the patient data comprising objective patient data at least indicative of stimulation therapy activity and subjective patient data indicative of patient feedback. As shown at 104 in FIG. 3B, the method 100 may further include presenting the GUI by displaying selected ones of the plurality of GUI portions on a display screen of a clinician-controlled device. As previously and further described herein, the clinician portal may be accessible by the clinician and may provide automatic display of non-compliant patients on respective ones of the GUI portions in a manner that is efficient for the clinician to see and to transition between different GUI portions to obtain additional information and to interact with the patient(s). For example, as shown at 106 in FIG. 3C, the method 100 may further comprise, based on the patient data and the different classes of the plurality of patients, presenting a visual identification of respective ones of the plurality of patients on at least one of the plurality of GUI portions as being non-compliant patients and/or predicted non-compliant patients based on the at least one filter for different classes of the plurality of patients. In some examples, as shown at 108 in FIG. 3D, the plurality of GUI portions are displayed to expand features visually displayed on a display screen (e.g., of a clinician-controlled device) to manage the plurality of patients by exception based on a non-compliant criteria associated with the at least one filter, as further described herein.

Method examples are not limited to the features as illustrated by FIGS. 3A-3D and may include variations and further features, such as any of those described in connection with FIGS. 1-2 and further described herein in connection with FIGS. 4A-13F.

FIGS. 4A-5G are diagrams schematically representing several example GUI portions, which are displayable on a display screen associated with a computing device which may be mobile (e.g., phone, tablet, etc.) or stationary (e.g., desktop, workstation, etc.). In some examples, the GUI portions in FIGS. 4A-5G may comprise example implementations of the patient management app 860 operable and displayable as a GUI associated with a clinician portal 855, as further described in association with FIG. 7. Accordingly, these example GUI portions in FIGS. 4A-5G also comprise example implementations of the control portion 900 in FIG. 8A and/or user interface 940 in FIG. 9. In some examples, the GUI portions in FIGS. 4A-5G may be displayed as part of the methods described in connection with any of FIGS. 3A-3D.

In some examples, as used herein, a GUI refers to or includes visual components that convey information and represent actions that may be taken by a user, such as allowing for interaction with computing devices through icons, text, and/or audio. The GUI may be a visual display of text and graphics, including icons, which are displayed on a display screen of the computing device. A GUI portion refers to or includes a displayed portion of the GUI, which may include different displayed screens and/or different portions of a displayed screen.

It will be further understood that the arrangement of the various portions displayed on each respective GUI portion and/or the detailed listings within each respective GUI portion may act as a workflow method which a clinician (and/or a patient in some instances) may perform to advance patient care. Similarly, it will be apparent from FIG. 7 and the GUI portions in FIGS. 4A-5G, and the device, control portions, etc. in association with FIGS. 7-13F, that the various features, arrangements, components, etc. may be embodied as a system or apparatus.

FIGS. 4A-4M are each a diagram schematically representing example GUI portions. In some examples, the GUI portions of the clinician portal may be juxtaposed with each other in that the portions are selectable to transition therebetween. For example, and as further illustrated by the process of FIG. 6, a clinician may select different icons to cause a transition between respective ones of the GUI portions, where a transition includes causing display of the respective GUI portion on a display screen.

Figure 4C:
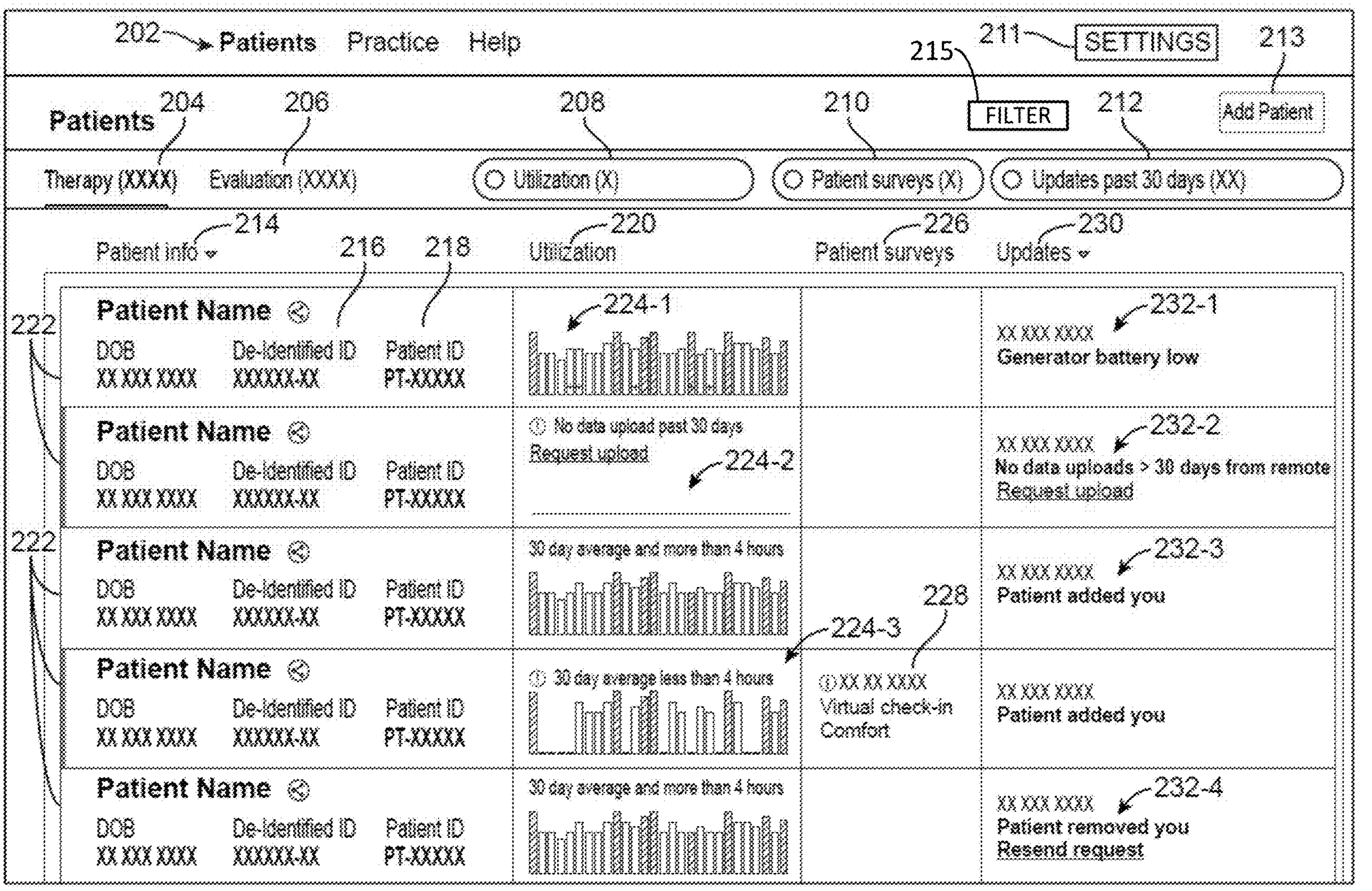

FIG. 4A is a block diagram schematically representing an example GUI portion 180, and which may comprise an example implementation of the patient management app 860 (FIG. 7), control portion 900 (FIG. 8A), and/or user interface 940 (FIG. 9), and/or may be presented according to any of the methods 100 (FIGS. 3A-3D) and/or by any device 25 and/or arrangement 20 (FIGS. 1-2). As shown in FIG. 4A, the GUI portion 180 comprises a banner including a patient indicator or icon 202, among other function selector icons (e.g., practice, help, etc.), such as a therapy icon 204 and an evaluation icon 206 as further described and illustrated by FIG. 4C. In some examples, the GUI portion 180 is populated using, and/or displays, patient data for a plurality of patients that includes both objective patient data and subjective patient data. The patient data may be populated in a patient identifying region 214, utilization region 220, patient survey region 226, and update region 230 for a group of example patient listings 222 (e.g., patient records for a plurality of patients in the group). In some examples, each patient listing 222 comprises, under patient identifying region 214, a name and/or other identifying information 182. A clinician may select a particular patient for further review, with at least some of those details being illustrated and further described herein.

In some examples, each patient listing 222 comprises subjective patient data and objective patient data for each of the patients and which is concurrently displayed on the GUI portion 180. The objective patient data and subjective patient data may be populated and/or co-displayed in proximity to each other in the regions 214, 220, 226, 230 of the GUI portion 180, such that the objective and subjective patient data is simultaneously present in the same viewable area.

At least some of the regions 214, 220, 226, 230 may display visual identification of respective patients of the listing 222 that are non-compliant based on at least one criteria. In some examples, the GUI portion 180 may present patient data for a plurality of patients based on at least one filter for different classes of the plurality of patients, such as classes of compliant patients and non-compliant patients. For example, the GUI portion 180 (or GUI portion 181 of FIG. 4B), which is sometimes herein referred to as "the main GUI display" or "the main therapy GUI portion", may be automatically populated using, and/or displays, a plurality of different non-compliance classes juxtaposed together via the utilization region 220, the patient survey region 226, and the update region 230 for each of the plurality of patients of the group and in the patient listing 222. In some examples, the different non-compliance classes may include the previously described under-utilizing patients, under-surveying patients, under-updating patients, attention-warranting-answer patients, and/or attention-warranting-titration patients.

As shown by FIG. 4A, respective regions 214, 220, 230 of the GUI portion 180 may present objective patient data while other respective regions 226 may present subjective patient data and/or may present both objective and subjective patient data. For example, at least one of the regions 214, 220, 226, 230 of the GUI portion 180 may be automatically populated using visual identification of patients of a plurality of patients that exhibit non-compliance and/or a highest degree of non-compliance for a class of non-compliance represented within the respective region (e.g., column).

As previously described, the patient data may be received and aggregated from a variety of sources. The GUI portion 180 may present the patient data from the different sources in a convenient manner by which the clinician may more quickly form an impression of the compliance of the patient, effectiveness of the therapy, ways in which the patient may be non-compliant, etc. Example parameters, icons, links, and/or indicators which may be populated in or displayed as: (i) the patient information 182 in the patient identifying region 214, (ii) the objective utilization data 184 in the utilization region 220, (iii) the subjective patient survey data 186 in the patient survey region 226, and/or (iv) the objective update data 188 in the update region 230, as further described herein at least in connection with FIG. 4C.

FIG. 4B is a block diagram schematically representing an example GUI portion 200, which may comprise one example implementation of the GUI portion 180 of FIG. 4A but with the GUI portion 181 including different and/or additional regions than GUI portion 180 of FIG. 4A, and/or the regions are displayed in different orders. Accordingly, examples of the present disclosure are not limited to the specific regions, patient data, and orders of the regions as illustrated by GUI portions 180, 181 of FIGS. 4A-4B. The common features and attributes of GUI portions 180, 181 of FIGS. 4A-4B, as illustrated by the common numbering, are not repeated for ease of reference. Similar to GUI portion 180 of FIG. 4A, the GUI portion 181 may be populated using, and/or displays, patient data for a plurality of patients that includes both objective patient data and subjective patient data. The patient data may be populated in the patient identifying region 214, utilization (or adherence) region 220, objective efficacy region 227, and subjective efficacy (or benefit) region 229 for a group of example patient listings 222.

At least some of the regions 214, 220, 227, 229 may display visual identification of respective patients of the listing 222 that are non-compliant based on at least one criteria. In some examples, the GUI portion 181 may present patient data for a plurality of patients based on at least one filter for different classes of the plurality of patients, such as classes of compliant patients and non-compliant patients, as previously described.

Similar to FIG. 4A, respective regions 214, 220, 227 of the GUI portion 181 may present objective patient data while other respective region(s) 229 may present subjective patient data. In some examples, at least one of the regions 214, 220, 227, 229 of the GUI portion 181 may be automatically populated using visual identification of patients of a plurality of patients that exhibit non-compliance and/or a highest degree of non-compliance for a class of non-compliance represented within the respective region (e.g., column).

The GUI portion 181 may present the patient data from the different sources in a convenient manner. Example parameters, icons, links, and/or indicators which may be populated in or displayed as: (i) the patient information 182 in the patient identifying region 214, (ii) the objective utilization data 184 in the utilization region 220, (iii) objective efficacy data 187 in the objective efficacy region 227, and/or (iv) subjective efficacy data 189 in the update region 229, at least some of which is further described in connection with FIG. 4C and the remaining described below.

In some examples, the objective and subjective efficacy data 187, 189 may include data indicative of patient adherence or non-compliance, such as factors indicating the patient is likely to or is adhering to a treatment plan and/or factors indicating the patient is or is likely to become non-compliant, is non-compliant, and/or causes of non-compliance, such as patient discomfort, stress, sleep disturbances, sleep information, titration, and patient outcome (e.g., AHI), among other factors. In some examples, the objective efficacy data 187 may include the objective update data 188 (FIG. 4A), among other data, including but not limited to, data received from sensors (e.g., sounds or pressure indicative of sleep disturbances, sleep information, patient outcome parameters and other information sensed by external monitoring circuitry and/or the IMD). In some examples, the subjective efficacy data 189 may include the subjective patient survey data 186 (FIG. 4A), among other data, such as patient provided sleep information, sleep disturbances, snoring, usage, comfort and other data.

In some examples, the objective efficacy region 227 refers to or includes a region displaying objective patient data 187 pertaining to an objective efficacy and/or adherence of the patient to the treatment plan. The objective efficacy region 227 may display objective efficacy data 187, such as objective factors which may indicate the patient is or may be likely to become compliant or non-compliant. Some non-limiting examples of objective factors which may indicate the patient is compliant or is adhering to the treatment plan, or likely to, include usage, patient outcome (e.g., such as any sensed parameter function 1374, as further described in connection with FIG. 10, and/or determined parameter 2500 as further described in connection with FIG. 12), sleep information, snoring, and other sensed parameters. Some non-limiting example objective factors which may indicate the patient is or may be likely to become non-compliant include data pertaining to a patient not completing a patient survey within a time period, not providing utilization data within the time period or a second time period, titrating (e.g., stimulation amplitude changes that deviate from a reference), snoring, sleep interruptions (e.g., sensed via external monitoring of acoustic, pressure, or other factors), sensed sleep state and/or other sleep information, patient outcome parameters, and other sensed parameters.

The objective efficacy region 227 may inform a clinician of a therapy effectiveness indication and/or a usage indication, etc., to help the clinician determine which patients are doing well and which may warrant faster or deeper attention based on at least one criteria, such as at least one filter. In some examples, at least one filter associated with the objective efficacy region 227 may include the filter(s), as further described in connection with the update region 230 of FIG. 4C.

In some examples, the subjective efficacy region 229 refers to or includes a region displaying patient data pertaining to subjective efficacy and/or adherence of the patient to the treatment plan. The subjective efficacy region 229 may display subjective efficacy data 189, such as subjective factors which may indicate the patient is or may be likely to become compliant or non-compliant. Some non-limiting example subjective factors which may indicate the patient is or may be likely to become non-compliant include negative patient feedback, such as answers to a patient survey indicating the patient is not using the device every night, is not comfortable, has hindrances, has device visible indicators, snoring has not improved or is worsening, the patient is feeling tired, among other patient feedback. Some non-limiting examples of subjective factors which may indicate the patient is compliant or is adhering to the treatment plan, or likely to, include positive patient feedback, such as answers to a patient survey indicating the patient is using the device every night, is comfortable, has no hindrances, has no device visible indicators, snoring has improved or otherwise not causing issues, the patient has high or normal energy levels, among other patient feedback. In some examples, the subjective efficacy region 229 may be populated using data indicative of answers to automatic queries which are presented to the patient on a patient app which is implemented on a patient communication device, among other data, such as data from external monitoring circuitry and/or the IMD, as further described herein.

The subjective efficacy region 229 may inform a clinician of a therapy effectiveness indication and/or the subjective factors which may be a cause of or may cause the patient to be non-compliant based on at least one criteria, such as at least one filter. In some examples, at least one filter associated with the subjective efficacy region 229 may include the filter(s) as further described in connection with the patient survey region 226, as described by FIG. 4C.

FIG. 4C is a block diagram schematically representing an example GUI portion 200, and which may comprise one example implementation of the patient management app 860 (FIG. 7), control portion 900 (FIG. 8A), and/or user interface 940 (FIG. 8), and/or the GUI portion 180 of FIG. 4A or GUI portion 181 of FIG. 4B. As shown in FIG. 4C, in some examples, the GUI portion 200 comprises a banner including a patient icon 202, among other function selector icons (e.g., practice, help, etc.). With the patient icon 202 selected, the example GUI portion 200 may comprise a therapy icon 204 and an evaluation icon 206. FIG. 4C represents an example implementation upon selection of the therapy icon 204, which includes patient data populated and/or displayed in different regions of the GUI portion 200, including a patient identifying region 214, utilization region 220, patient survey region 226, and update region 230 for a group of example patient listings 222 (e.g., patient records for a plurality of patients in the group). In some examples, each patient listing 222 may comprise, in patient identifying region 214: (i) a name, (ii) a date of birth (DOB), (iii) a de-identified identifier (ID) 216, and/or (iv) a patient ID 218. A clinician may select a particular patient for further review, with at least some of those details being illustrated and further described herein in association with FIGS. 5A-5G.

As noted above, each patient listing 222 comprises subjective patient data and objective patient data for each of the patients and which is concurrently displayed on the GUI portion 200. For example, the GUI portion 200, which is sometimes herein referred to as "the main GUI display" or "the main therapy GUI portion", may be automatically populated using, and/or may display, a plurality of different non-compliance classes juxtaposed together via the utilization region 220, the patient survey region 226, and the update region 230 for each of the plurality of patients of the group and in the patient listing 222. In some examples, the different non-compliance classes may include the previously described under-utilizing patients, under-surveying patients, under-updating patients, and/or attention-warranting-answer patients. In some examples, the different non-compliance classes may include the previously described under-utilizing patients, under-surveying patients, under-updating patients, attention-warranting-answer patients, and/or attention-warranting-titration patients.

Each patient may include information for the different non-compliance classes, with respective patients visually identified or flagged based on at least one filter for different classes of the plurality of patients. In some examples, a filter, as used herein, refers to or includes a criteria, such as a threshold, a rate, or a reference, indicating a patient is compliant or non-compliant with respect to the particular compliance class. Patients which do not comply with or are outside the criteria, e.g., are below the threshold(s) or rate or deviate from a reference, may be visually identified or flagged on the GUI portion 200, such that the clinician may easily view non-compliant patients and/or predicted non-compliant patients.

The following describes each of the utilization region 220, the patient survey region 226, the update region 230, and the respective filters associated therewith.

In some examples, the utilization region 220 refers to or includes a region that displays patient data pertaining to average patient use of an IMD per day over a time period. In the particular example, the utilization region 220 includes use of IMD per day over thirty days. In some examples, use of the IMD may comprise delivery of stimulation therapy to the patient, and in other examples, may comprise general use of the IMD (e.g., wearing the IMD with IMD activated). In some examples, at least one filter associated with the utilization region 220 may include an average rate of use of the IMD that is less than a threshold (or other criteria) over the time period. For example, a first filter may include a thirty day average use of the IMD that is less than four hours. A second filter may include no utilization data uploaded for the time period, e.g., the thirty days. In some examples, a third and/or fourth filter may include a stimulation amplitude change that differs from a reference, such as a patient whose stimulation amplitude changes are overly-aggressive (e.g., overly-aggressive titration patient) or overly-passive (e.g., overly-passive titration patient) for a given period of time compared to the reference, as further described herein. As shown by FIG. 4C, in some examples, the utilization region 220 is populated using, and/or displays, data for patients that are compliant and patients that are non-compliant. More particularly, each patient listing 222, in the utilization region 220, may comprise data indicative of the patient use of an associated IMD. As shown at 224-1 and 224-2 of FIG. 4C, the utilization region 220 may include graphs with bars representing the IMD use per day and over the time period (e.g., 30 days). For patients that are non-compliant, the utilization region 220 may include a graph with a visual indication of the IMD utilization being below the threshold (e.g., an attention icon or indicator), as shown by 224-3, or absence of graph that visual indicates IMD utilization below the threshold (or other criteria), as shown by 224-2. More particularly, as shown by 224-2, for a patient with no utilization region 220 uploaded for the time period, a link may be displayed which is selectable to cause or initiate a communication to be output to a patient communication device to request upload of data (e.g., "Request upload"). Example patient communication devices are further described herein. In some examples, a visual indication may be displayed for attention-warranting-titration patients, such as overly-aggressive titration patients and/or overly-passive titration patients, which may be displayed in the utilization region 220 and/or another region, such as an objective efficacy region 227 of FIG. 4B.

As further described later in association with at least FIGS. 13A-13D, some overly-aggressive titration patients may become non-compliant via less usage or non-use after increasing their stimulation amplitude too quickly over a given period of time (e.g. days, weeks, months) which may cause discomfort, and then exhibit poor outcomes (e.g. disease burden (e.g. AHI) which is still too high). On the other hand, some overly-passive titration patients may become non-compliant from a lack of enthusiasm (which may lead to less usage, non-use) due to increasing their stimulation amplitude too slowly over a given period of time (e.g. days, weeks, months), from which they likely will exhibit poor outcomes (e.g. disease burden (e.g. AHI) which is still too high). Such poor outcomes may discourage the patient because the patient continues to experience too many apnea events.

In some examples, a filter may be used that is associated with a titration of the IMD or other stimulation therapy device. For example, the filter may be associated with a stimulation amplitude change (of the IMD) that is deviates from a reference (e.g., threshold or other criteria) for a patient. In some examples, the IMD or other stimulation therapy device may have a variable stimulation amplitude, which may be adjusted based on patient outcomes (e.g., responses to the therapy) and/or usage over a period of time to identify a setting that maximizes patient usage while minimizing disease burden (e.g., improving patient outcomes). In some example, the patient outcome may include a parameter, such as sleep quality, sleep disorder breathing burden (e.g., apnea-hypopnea index (AHI)), or other sensed or determined parameters.

Figure 10:
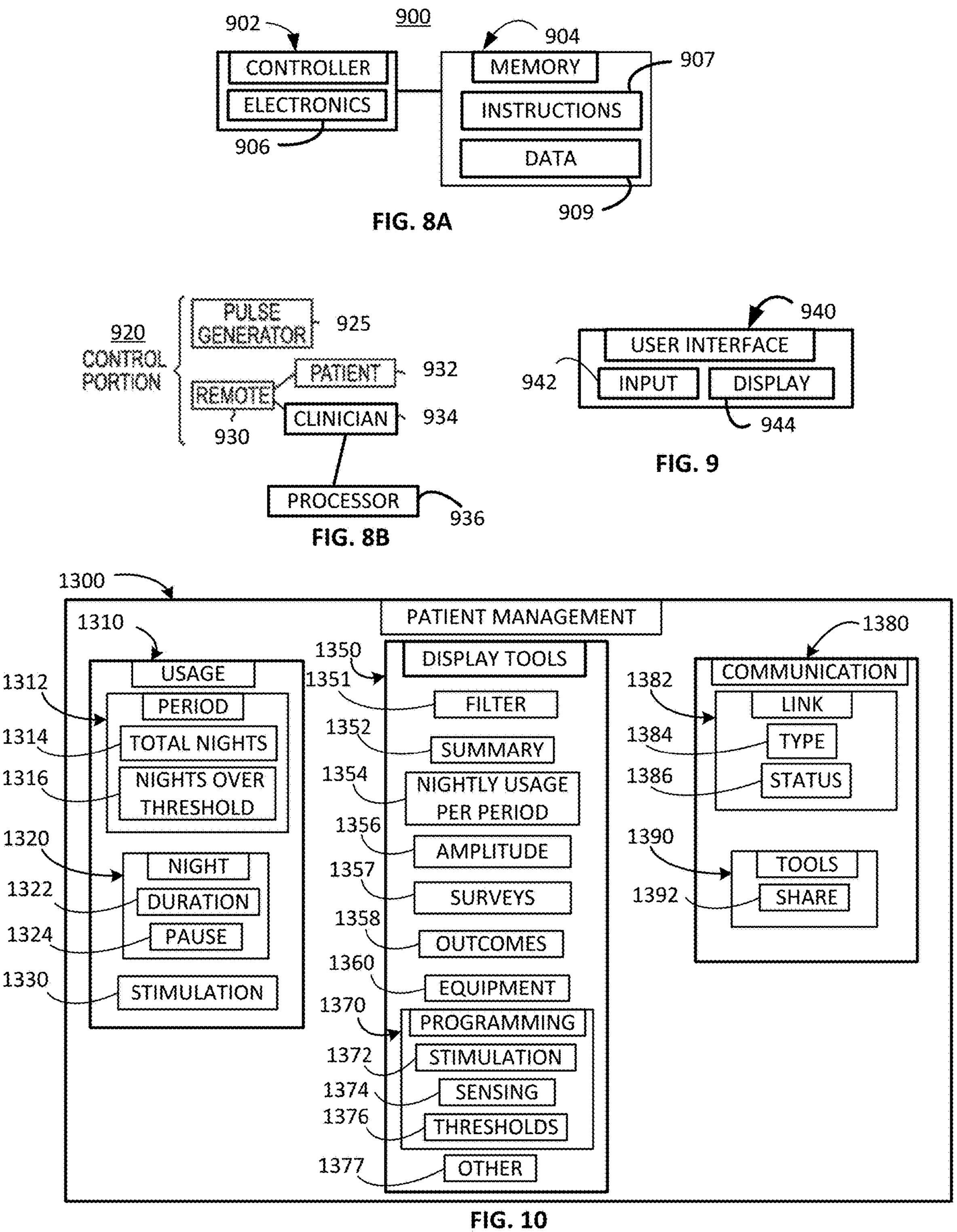
FIG. 10 is a block diagram schematically representing an example patient management engine.
Figures 11, 12:
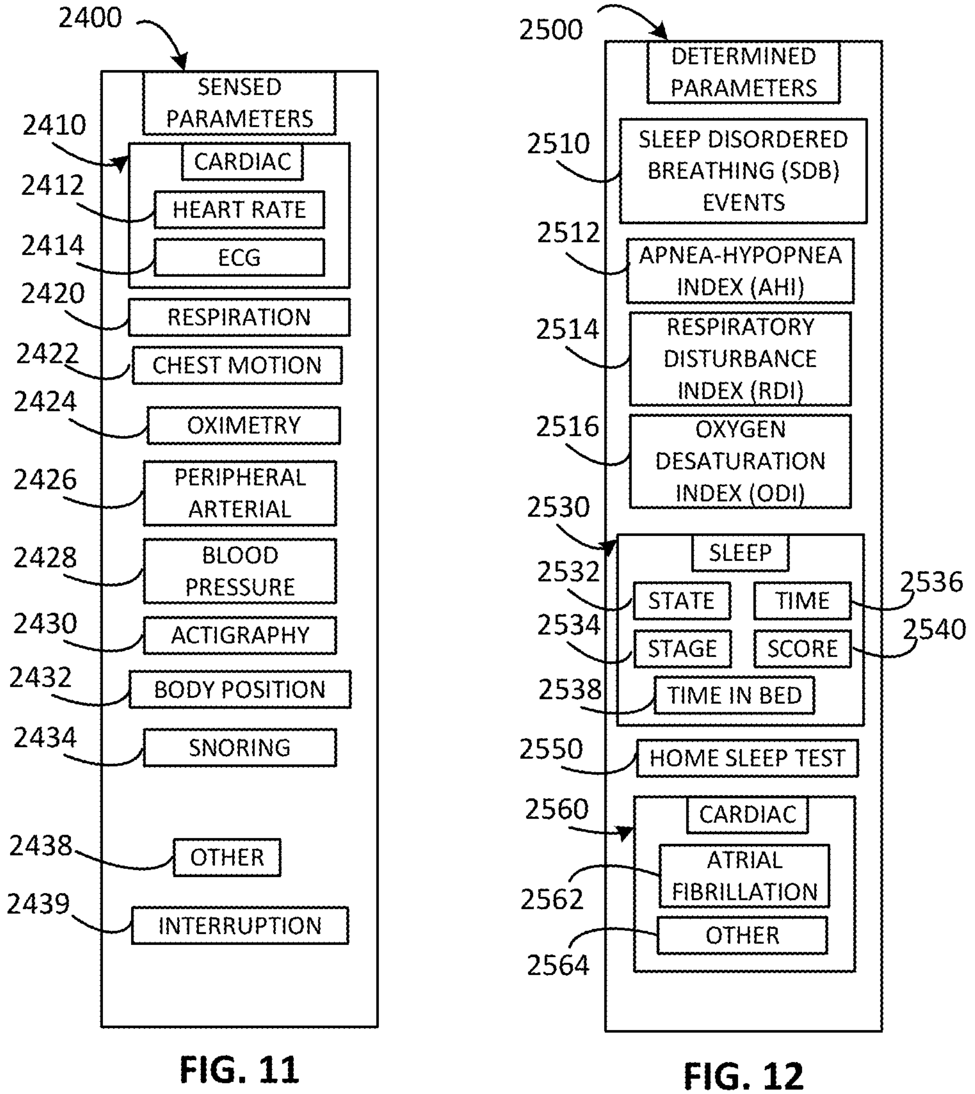
FIG. 11 is a block diagram schematically representing example sensing parameters associated with at least a third party diagnostic/monitoring portion.
FIG. 12 is a block diagram schematically representing example determined parameters associated with at least a third party diagnostic/monitoring portion.

In some examples, the patient outcome may include a sensed parameter function 1374 and/or determined parameter 2500 as further described herein in connection with FIGS. 10 and 12, and may include use of sensed parameters 2400 (FIG. 11). In some examples, the patient may have an input for titrating (e.g., increasing) the stimulation amplitude over time. In various examples, at some point in time after the IMD is implanted in the patient, the stimulation amplitude for the IMD may be titrated for therapeutic patient use, such as after an initial setup via a clinician. For example, the IMD (e.g., via control portion 900 of FIG. 8A) may be programmed to guide the patient through (or to otherwise perform) the titration by starting at a baseline amplitude and increasing the stimulation amplitude over time (e.g., from about 1.4 Volts to about 2.2 Volts) and observing patient outcome and usage parameters in response to stimulation applied at the different stimulation amplitudes. In some examples, stepwise increases (e.g., increments) in the stimulation amplitude is made over a period of time, such as but not limited to, stepwise changes of 0.1 Volts over a first 90 days of therapy until patient outcomes improve (e.g., disease burden decrease) while a desirable usage rate (e.g., number of hours per night) is achieved and/or maintained. In some examples, if the patient outcomes decrease (e.g., disease burden increases) and/or usage parameters decrease (e.g., usage rate decreases), then the stimulation amplitude may be stepwise decreased (e.g., decremented). The stepwise increase and/or decrease of the stimulation amplitude may continue over the period of time until a suitable solution (e.g., stimulation amplitude value) is achieved which takes into consideration both favorable patient outcomes (decreasing disease burden (e.g., AHI) relative to a threshold or other criteria) and favorable patient usage (e.g., minimum number of hours per night, per week, etc.). In some such examples, a target solution may include selecting a stimulation amplitude which strikes a balance between the two goals of favorable patient outcomes (e.g., decreased disease burden) and favorable patient usage (e.g. number of hours used per day, per week, etc.).

In some instances, the patient (or the clinician or otherwise) may increase the stimulation therapy amplitude too quickly which may cause discomfort and/or sleep arousal, and may lead to reduced usage (which may include non-use) and/or rapid decrease in stimulation amplitude settings, either of which may qualify as patient non-compliance. In some cases, the patient may develop such a negative association with therapy that they may all together cease therapy. In some examples, the titration reference (sometimes herein interchangeably referred to as "stimulation amplitude change reference") may include a stimulation amplitude change associated with an average of many patients or other reference and/or maximum and minimum amplitude values. Patients which titrate (e.g., increase or decrease stimulation amplitude) at a rate differing from the reference (e.g., over or under the reference) may not be adhering to the treatment plan and/or may otherwise be a factor for why a patient may be non-compliant or may become non-compliant.

With this in mind, the later-described FIGS. 13A-13D provide example patterns of stimulation amplitude changes by various example patients.

For instance, in some examples, a patient may increase the stimulation amplitude of the IMD too quickly compared to the reference for a given time period (e.g. day(s), week(s), month(s)). This patient may be flagged as an attention-warranting-titration patient, which may then be displayed in a GUI portion (e.g., FIGS. 4A-4B, etc.) in accordance with various examples of the present disclosure. In some examples, a patient may increase the stimulation amplitude of the IMD too slowly compared to the reference for a given period of time (e.g., day(s), week(s), month(s)), and may be flagged as an attention-warranting-titration patient. In some examples, the stimulation amplitude changes may be displayed in an amplitude changes region 450 of a GUI portion 400, as illustrated further herein at least in connection with FIG. 5A.

In some examples, the patient survey region 226 refers to or includes a region displaying patient data pertaining to answer(s) a patient provides for a patient survey within the time period. In some examples, the patient survey region 226 is populated using, and/or displays, data that tracks answers a patient provides in a patient survey as part of a virtual check-in and/or how many and/or when the patient survey(s) were completed. As further described herein, the patient survey region 226 may be populated using data indicative of answers to automatic queries which are presented to the patient on a patient app which is implemented on a patient communication device. In some examples, in order to more conspicuously identify patient(s) which need attention from a caregiver, the patient survey region 226 is populated using, and/or displays, an answer that is negative or that otherwise indicates an issue with patient care, such as the patient being tired or uncomfortable with the IMD, which is sometimes herein referred to as an attention-warranting-answer.

In some examples, the patient survey region 226, which is populated using subjective patient data, may assist the clinician in identifying why the patient is non-compliant, how to resolve the non-compliance, and/or to predict the patient will or may become non-compliant. The answers to the patient surveys may include subjective patient data (and the patient not responding to a patient survey may include objective data (e.g., objective identification that subjective patient data is missing) which forms part of the update region 230 described below). For example, the patient survey may include answers to queries which are associated with: (i) nightly usage (e.g., "are you using the device every night?); (ii) comfort (e.g., "is the stimulation comfortable?"); (iii) hindrances; (iv) device visible indicators; (v) snoring (e.g., "has your snoring improved?"); (vi) feeling or energy levels (e.g., "do you feel tired?"), and/or other parameters. Answers which are negative may indicate there is an issue for the patient, such as the patient indicating they are not using their device every night, they are uncomfortable, snoring is not improving, and/or they have low energy levels (e.g., are feeling tired). The patient survey may be implemented and/or comprise at least some of substantially the same features and attributes as those described in the PCT Publication WO2022/182756, published on Sep. 1, 2022, and entitled "Integrating Stimulation Therapy, Patient Management, and External Patient Monitoring", corresponding to U.S. National Stage Application Ser. No. 18/278,263, filed Aug. 22, 2023, and published on Apr. 18, 2024 as U.S. Patent Application Publication 2024/0123232, the entire teachings of which are incorporated herein by reference (which includes the publication of the Appendix of the provisional).

In some examples, at least one filter (e.g., filter 29 of FIG. 1) associated with data populated in the patient survey region 226 may include answers to a query for a patient survey that is negative and is provided within the time period, such as answers indicating an issue for the patient (e.g., patient is tired or uncomfortable, patient is not using the IMD every night). In some examples, the patient survey region 226 may be populated using, and/or may display, data indicative of patients which have provided a particular answer to a patient survey indicating the issue. For example, as shown by 228 of FIG. 4C, the patient survey region 226 indicates the patient provided a negative answer to a virtual check-in at a particular date and associated with a query related to comfort (e.g., the patient answered "uncomfortable").

In some examples, the update region 230 refers to or includes a region displaying patient data pertaining to a therapy-related update status. The update region 230 may inform a clinician of a therapy effectiveness indication and/or a usage indication, etc., to help the clinician determine which patients are doing well and which may warrant faster or deeper attention. In the particular example, the update region 230 is populated using, and/or displays, information on the last update for the patient, which may include data pertaining to a patient not completing a patient survey within a time period, not providing utilization data within the time period or a second time period, and other updates.

In some examples, at least one filter associated with the update region 230 may include or be associated with patients whom have not provided the therapy-related update status in the threshold time period, such as thirty days. The therapy-related update status may include data from a patient remote and/or IMD indicative of stimulation provided and/or indicative of no response to a patient survey. In some examples, a filter associated with data populated in the update region 230 may include answers to a query for a patient survey that is outside (e.g., greater than) a time period, such as a patient not responding or providing answers to a patient survey within the time period. In some examples, update region 230 is displayed for patients that are compliant and patients that are non-compliant. For example, even patients that are compliant with the criteria associated with the filter (e.g., provided an update within thirty days) may still have data populated in the update region 230 for other reasons that patient(s) may need attention, such as a battery being low.

More particularly and in some examples, each patient listing 222, in the update region 230, is populated using update parameters indicative of the last therapy-related update status or lack of a therapy-related update status in the time period, as shown at 232-1, 232-2, 232-3, 232-4. The update region 230 may be further populated using, and/or displays, data that tracks whether or not a patient has completed a survey as part of a virtual check-in. For patients that are non-compliant, the update parameters may include a visual indication of the update not being provided in the threshold time period (e.g., utilization data and/or survey not being provided), a date the update was due, and/or an link that is selectable to cause or initiate a communication to be output to a patient communication device to request upload of data (e.g., "Request upload", "No data uploads for over 30 days from patient remote"), as shown by 232-2. In various examples, the patient survey region 226 is populated using, and/or displays, data identifying a patient survey has not been provided by the patient within a threshold time period, such as in one week, two weeks or thirty days. Said differently, the patient survey may be overdue. For example, the data may be indicative of patients which have not provided a patient survey at all and/or have not provided responses to particular queries within a threshold time period (e.g., comfort question, energy level question). As a specific example, as shown by 232-5 of FIG. 4E, the update region 230 indicates a virtual check-in was missed and is overdue by 7 days for the patient. Example data or parameters displayed for compliant patients includes, but is not limited to: (i) visual indications of the last update, such as a battery being low (232-1); (ii) a patient adding the clinician (232-3); and (iii) a patient removing the clinician with a link that is selectable to cause a communication to be output to a patient communication device to request adding the clinician. Adding the clinician by the patient may permit data to be communicated from the IMD to the clinician portal, such as through a patient communication device.

In various examples, the GUI portion 200 is further populated using, and/or displays, various icons which are selectable to expand on features. For example, the icons are selectable to cause transition to another of the plurality of GUI portions, such as those illustrated by FIGS. 4E-5G. As some examples, the GUI portion 200 includes a settings icon 211, an add patient icon 213, and/or a filter select icon 215. In some examples, the settings icon 211 is selectable to cause transition to the GUI portion 300 illustrated by FIG. 4I, and the add patient icon 213 is selectable to cause transition to the GUI portion 258 illustrated by FIG. 5F, as further described herein.

As further shown in FIG. 4C, the GUI portion 200 may be populated using, and/or may display, a plurality of filter icons 208, 210, 212. In some examples, the filter icons 208, 210, 212 may enable a clinician to filter or sort the patient listings 222 according to various criteria and based on the at least one filter for different classes of the plurality of patients. In response to selecting one of the filter icons 208, 210, 212, the display may transition to one of the GUI portions 250, 252, 254 of FIGS. 4E-4G. As a result, upon the clinician opening the GUI portion 200, the patient listings 222 may already be sorted according to the clinicians preferred criteria. Among other features, this arrangement may help the clinician quickly determine which patients the clinician would like to assess first or last, etc.

As described above, in some examples, the filter icons 208, 210, 212 may perform filtering according to which patient listings are identified as non-compliant (per a non-compliant criteria associated with a filter), with the filter icons 208, 210, 212 also having selection capabilities for which non-compliance classes are to be filtered, in some examples. The filter icons 208, 210, 212 and/or categorization functionality may enable a clinician to quickly spot the patient listings 222 for non-compliant patients or near non-compliant patients which may warrant faster or more attention. The filter icons 208, 210, 212 may comprise a manual selection feature by which the clinician may select a patient listing 222 to be visually displayed and/or may comprise an automatic selection feature by which the patient listings are automatically visually displayed with patient data according criteria pre-selected by the clinician and/or device manufacturer, etc. As a result, upon the clinician opening the GUI portion 200, at least some of the patient listings 222 may already be visually flagged according to the clinicians preferred criteria based on the at least one filter. Among other features, this arrangement may help the clinician quickly determine which patients the clinician would like to assess first or last, etc.

As described above, among other criteria by which a patient listing 222 may be filtered and/or flagged, the GUI portion 200 may enable sorting and/or flagging patient listings according to those patients which have missed appointments, are no longer seeking care, as well as other parameters further addressed in later Figures, such as the patient stopping use of the device, underutilization, discomfort, and the like.

In some examples, the at least one filter for different classes of the plurality of patients may be implemented automatically by which the GUI portion 200 automatically sorts the patient listings 222 according to criteria preselected by the clinician and/or device manufacturer, etc. For example, the patients in the patient listings 222 may be ordered and displayed with non-compliant patients and/or non-compliant patients at higher-relative degrees of non-compliance being listed first followed by lower-relative degrees of non-compliant patient and/or compliant patients. In some such examples, the non-compliant patients are automatically flagged first and highlighted to the clinician without and/or prior to the clinician selecting one of the filter icons 208, 210, 212.

Figure 4D:
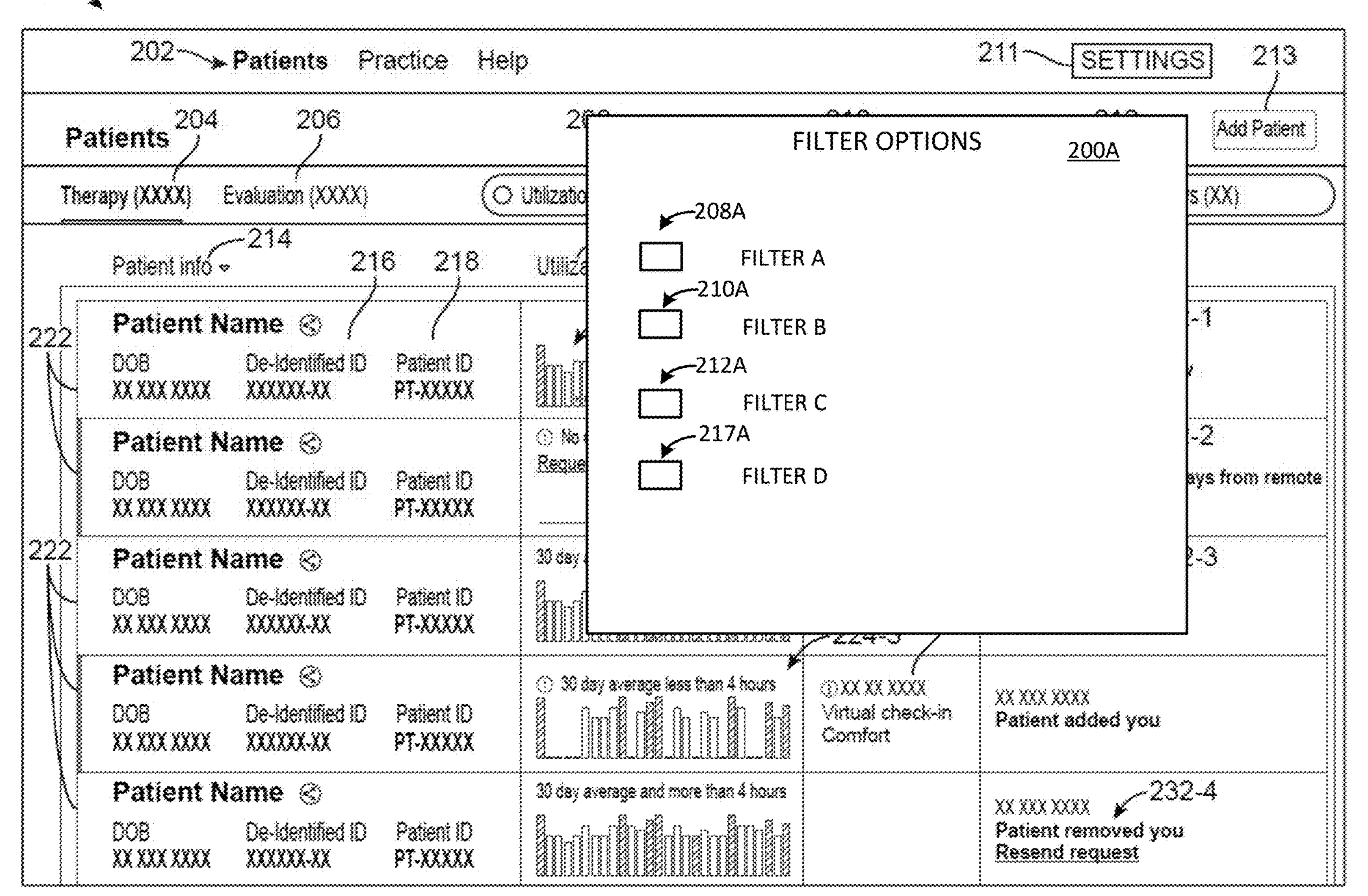

In some examples, the filter select icon 215 of GUI portion 200 of FIG. 4C may be selected to cause transition to GUI portion 200A illustrated by FIG. 4D. As shown by FIG. 4D, in response to user selection of the filter select icon 215, the GUI portion 200A may be populated using, and/or displays, an expanded window that visually displays different filter options 208A (Filter A), 210A (Filter B), 212A (Filter C), 217A (Filter D) which are available and/or selectable by the clinician. For example, the GUI portion 200A may be further populated using, and/or displays, different selectable filter options 208A, 210A, 212A, 217A which may result in the display of at least one of a plurality of filter icons 208, 210, 212, and/or other icons (such as an icon corresponding to filter option 217A) on GUI portion 200 of FIG. 4C in response to user selection and/or non-display or removal of at least one of the plurality of filter icons 208, 210, 212 (or other icon) on the GUI portion 200 of FIG. 4C in response to user non-selection or deselection of the filter options 208A, 210A, 212A, 217A in GUI portion 200A (FIG. 4D). In some: examples, the filter options may include under-utilizing patients, under-surveying patients, under-updating patients, attention-warranting-answer patients, and/or attention-warranting-titration patients, as previously described.

Figure 4E:
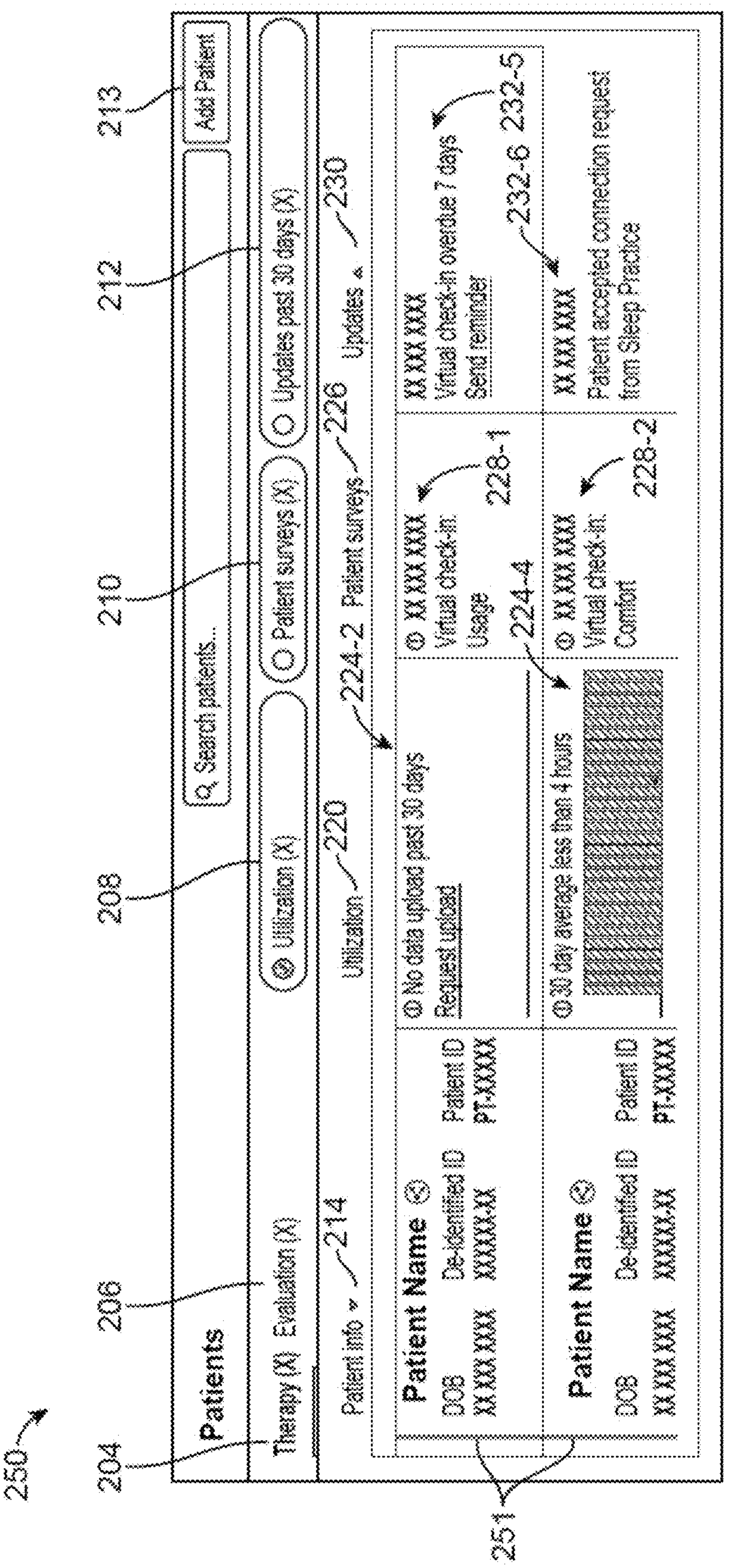

FIG. 4E is a block diagram schematically representing an example GUI portion 250 for patient care, which comprises at least some of substantially the same features and attributes of the GUI portion 200 of FIG. 4A, except being an example implementation in response to selection of the utilization filter icon 208 on GUI portion 200 of FIG. 4C. As shown by GUI portion 250, in response to the selection, the patient listing may be filtered such that non-compliant patients associated with utilization of respective IMDs are populated in and/or visually displayed in the GUI portion 250. In some examples, patients that are compliant with the utilization filter (e.g., criteria) are not populated in and/or displayed by the GUI portion 250. In some examples, the patients are filtered for non-compliance and the filtered patient listing 251 is displayed in the GUI portion 250 which is populated using at least some of the same data as GUI portion 200 of FIG. 4C, including the data (e.g., parameters, links, visual indicators) populated in the patient identifying region 214, the utilization region 220, the patient survey region 226, and the update region 230. The particular example illustrates further examples of patient data. For example, the utilization region 220 may be populated using a visual indication of no data uploaded within thirty days and the link to request upload, as shown by 224-2, and a graph with bars illustrating the average IMD usage and a visual indication that the average usage over the thirty days is less than four hours, as shown by 224-4. The example patient survey region 226 is populated using visual indications of a virtual check-in being missed for greater than a threshold time period and for different types of answers to queries (e.g., usage and comfort), as shown by 228-1, 228-2. The example update region 230 is populated using visual indications of the last therapy-related status update, such as the virtual check-in being late with a link to send a reminder (e.g., to promote patient compliance), as shown by 232-5, and a visual indication of the patient accepting a connection request, as shown by 232-6.

As may be apparent from FIG. 4E, in some examples, while the patients are filtered on the basis of utilization, GUI portion 250 also displays (e.g., co-displays) patient data in patient survey region 226 (e.g., patient survey parameters) and in update region 230 (e.g., update parameters) which may simultaneously indicate other types or degrees of non-compliance by a particular patient. As further shown by FIGS. 4F-4H, similarly in some examples, while the patients are filtered on the basis of patient surveys and/or updates (and/or utilization), the GUI portions 252, 254, 256 display (e.g., co-displays) patient data in the utilization region 220, the patient survey region 226, and the update region 230 (e.g., update parameters).

In some examples, the GUI portion 250 further includes the banner populated using, and/or displaying, the therapy icon 204, the evaluation icon 206, and/or the add patient icon 213, among other icons, such that the plurality of GUI portions may be transitioned between and with at least a portion being selectable directly from the GUI portion 250. As a further example, the GUI portion 250 may be populated using, and/or displaying, the filter icons 208, 210, 212 which are selectable to transition between GUI portion 250 and the GUI portions 252, 254, 256 of FIGS. 4F-4H, among others. As such, the clinician may efficiently and easily transition between different classes of non-compliant patients.

Figure 4F:
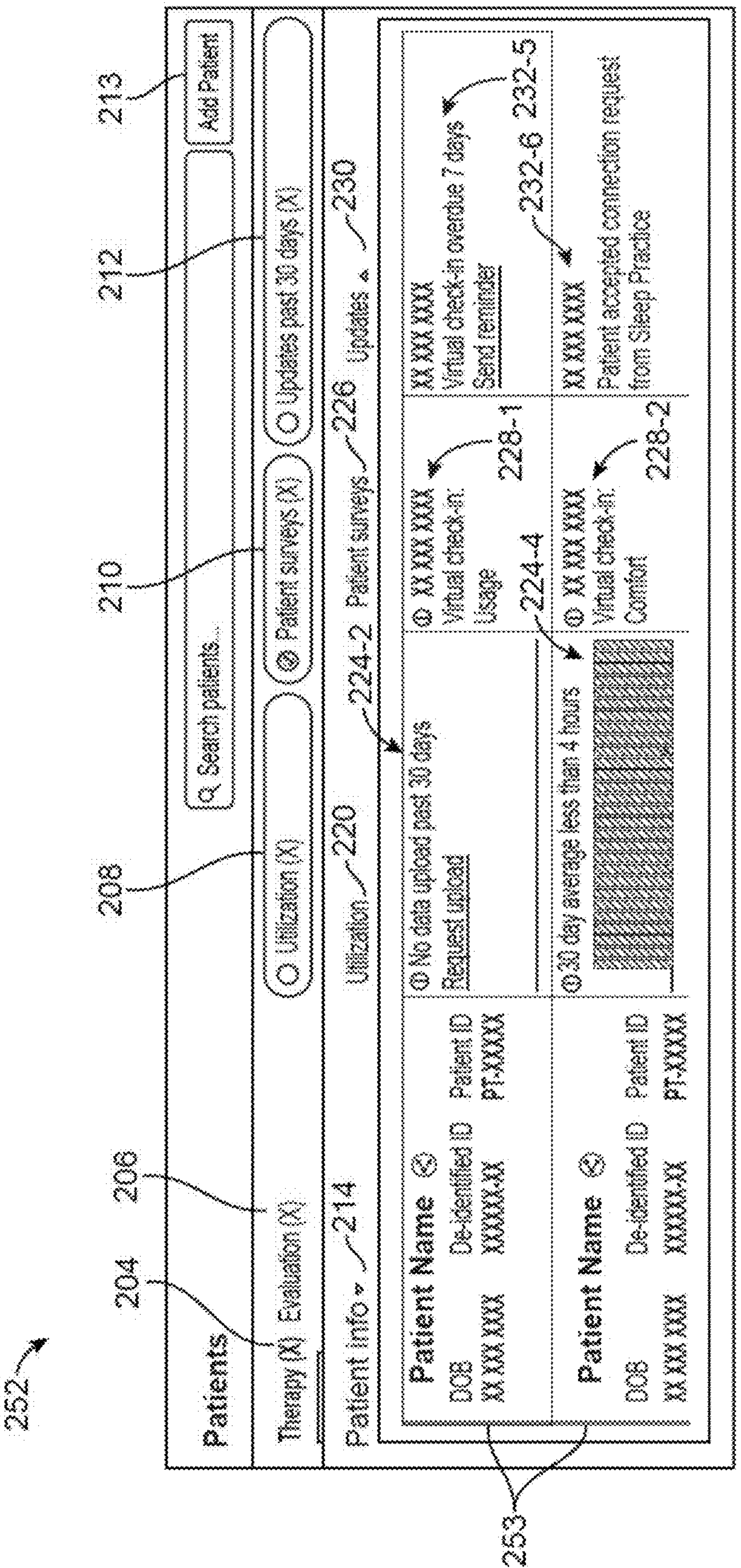

FIG. 4F is a block diagram schematically representing an example GUI portion 252 for patient care, which comprises at least some of substantially the same features and attributes of the GUI portion 200 of FIG. 4C, except being an example implementation in response to selection of the patient survey filter icon 210 on GUI portion 200 of FIG. 4C and/or from any other GUI portions containing a patient survey filter icon 210, such as GUI portion 250 of FIG. 4E. As shown by GUI portion 252, in some examples and in response to the selection, the patient listing is filtered such that non-compliant patients associated with patient surveys are populated, and/or visually displayed, in the GUI portion 252. In some examples, patients that are compliant with the patient survey filter (e.g., criteria) are not populated in, and/or displayed by, the GUI portion 252. The patients may be filtered for non-compliance and the filtered patient listing 253 is displayed in the GUI portion 250 which is populated using, and/or displays, at least some of the same data as previously described in association with FIG. 4A, including data in the patient identifying region 214, the utilization region 220, the patient survey region 226, and the update region 230. Similarly, the GUI portion 252 may further be populated using, and/or displays, the banner with the therapy icon 204, the evaluation icon 206, and/or the add patient icon 213, among other icons.

Figure 4G:
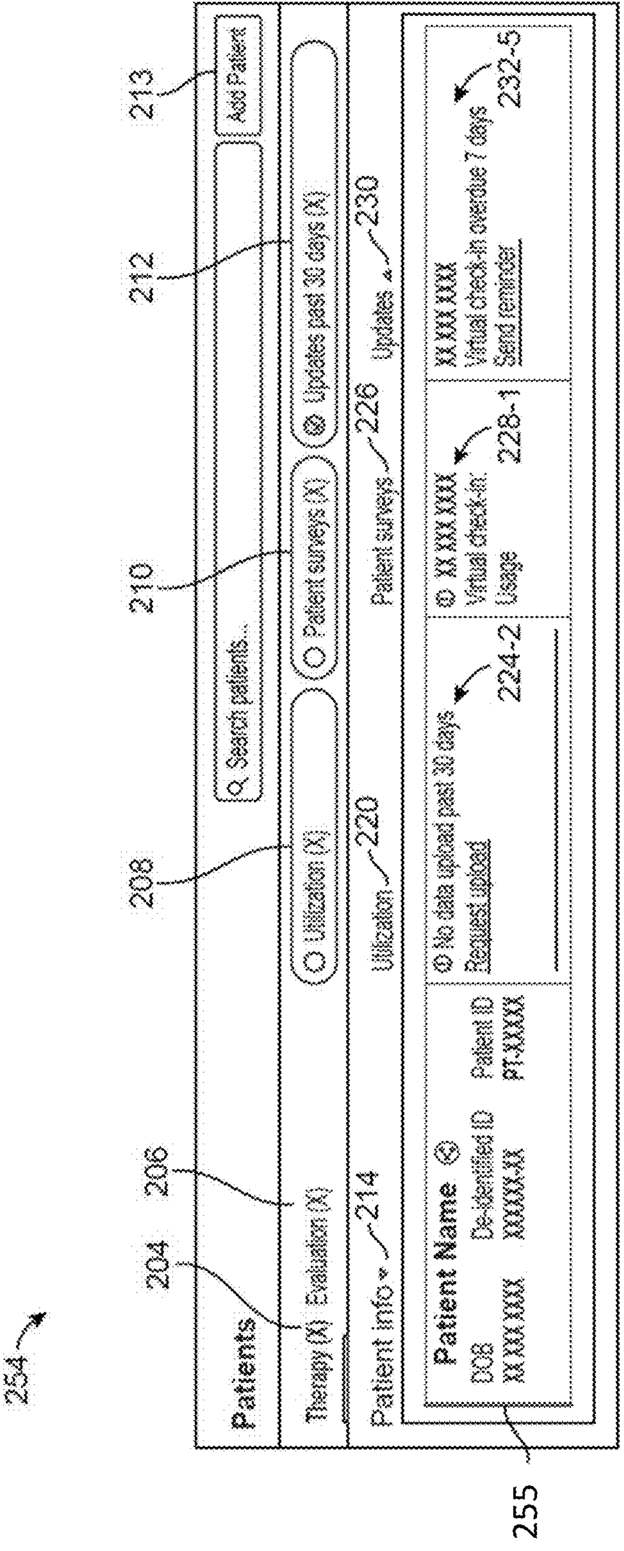

FIG. 4G is a block diagram schematically representing an example GUI portion 254 for patient care, which comprises at least some of substantially the same features and attributes of the GUI portion 200 of FIG. 4C, except being an example implementation in response to selection of the update filter icon 212 on GUI portion 200 of FIG. 4C and/or from any other GUI portions containing an update filter icon 212, such as GUI portion 250 of FIG. 4E. As shown by GUI portion 254, in some example and in response to the selection, the patient listing is filtered such that non-compliant patients associated with therapy-related status updates are populated, and/or visually displayed, in the GUI portion 254. In some examples, patients that are compliant with the update filter (e.g., criteria) may not be illustrated by the GUI portion 254. In some examples, the patients are filtered for non-compliance and the filtered patient listing 255 is displayed in the GUI portion 254, which is populated using, and/or displays, at least some of the same data as previously described in connection with FIG. 4C, including the data in the patient identifying region 214, the utilization region 220, the patient survey region 226, and the update region 230. Similarly, the GUI portion 254 may further be populated using, and/or may display, the banner with the therapy icon 204, the evaluation icon 206, and/or the add patient icon 213, among other icons.

Figure 4H:
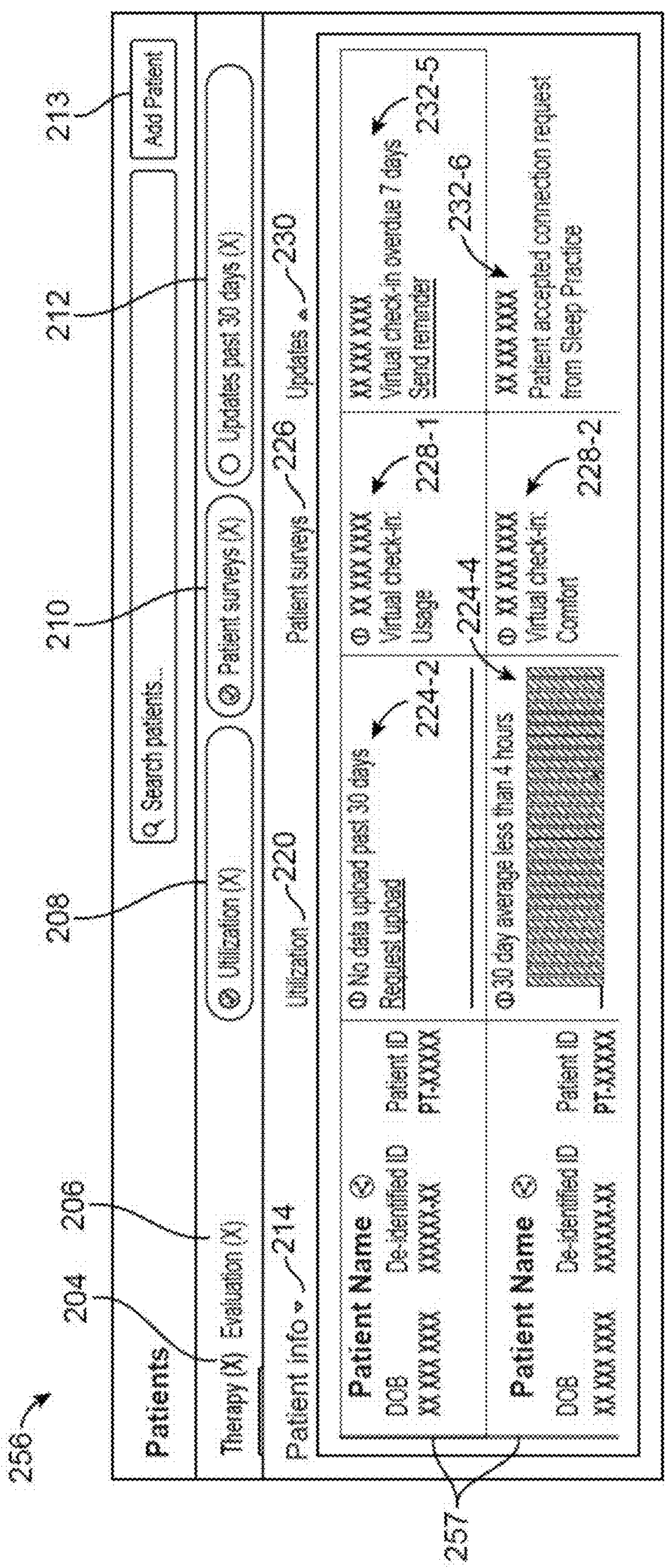

In some examples, more than one of the filter icons 208, 210, 212 may be selected at one time. FIG. 4H is a block diagram schematically representing an example GUI portion 256 for patient care, which comprises at least some of substantially the same features and attributes of the GUI portion 200 of FIG. 4C, except being an example implementation in response to selection of the utilization filter icon 208 and the patient survey filter icon 210 on GUI portion 200 of FIG. 4C and/or from any other GUI portions containing a utilization filter icon 208 and a patient survey filter icon 210, such as GUI portion 250 of FIG. 4E. As shown by GUI portion 256, in some examples and in response to the selection, the patient listing is filtered such that non-compliant patients associated with utilization and/or patient surveys are populated, and/or visually displayed, in the GUI portion 256. In some examples, patients that are compliant with the utilization and patient survey criteria may not be populated in, and/or displayed by, the GUI portion 256. In some examples, the patients are filtered for non-compliance and the filtered patient listing 257 is displayed in the GUI portion 254, which is populated using, and/or displays, at least some of the same data previously described in connection with FIG. 4C, including data in the patient identifying region 214, the utilization region 220, the patient survey region 226, and the update region 230. Similarly, the GUI portion 254 may further be populated using, and/or displays, the banner with the therapy icon 204, the evaluation icon 206, and/or the add patient icon 213, among other icons.

Figure 4I:
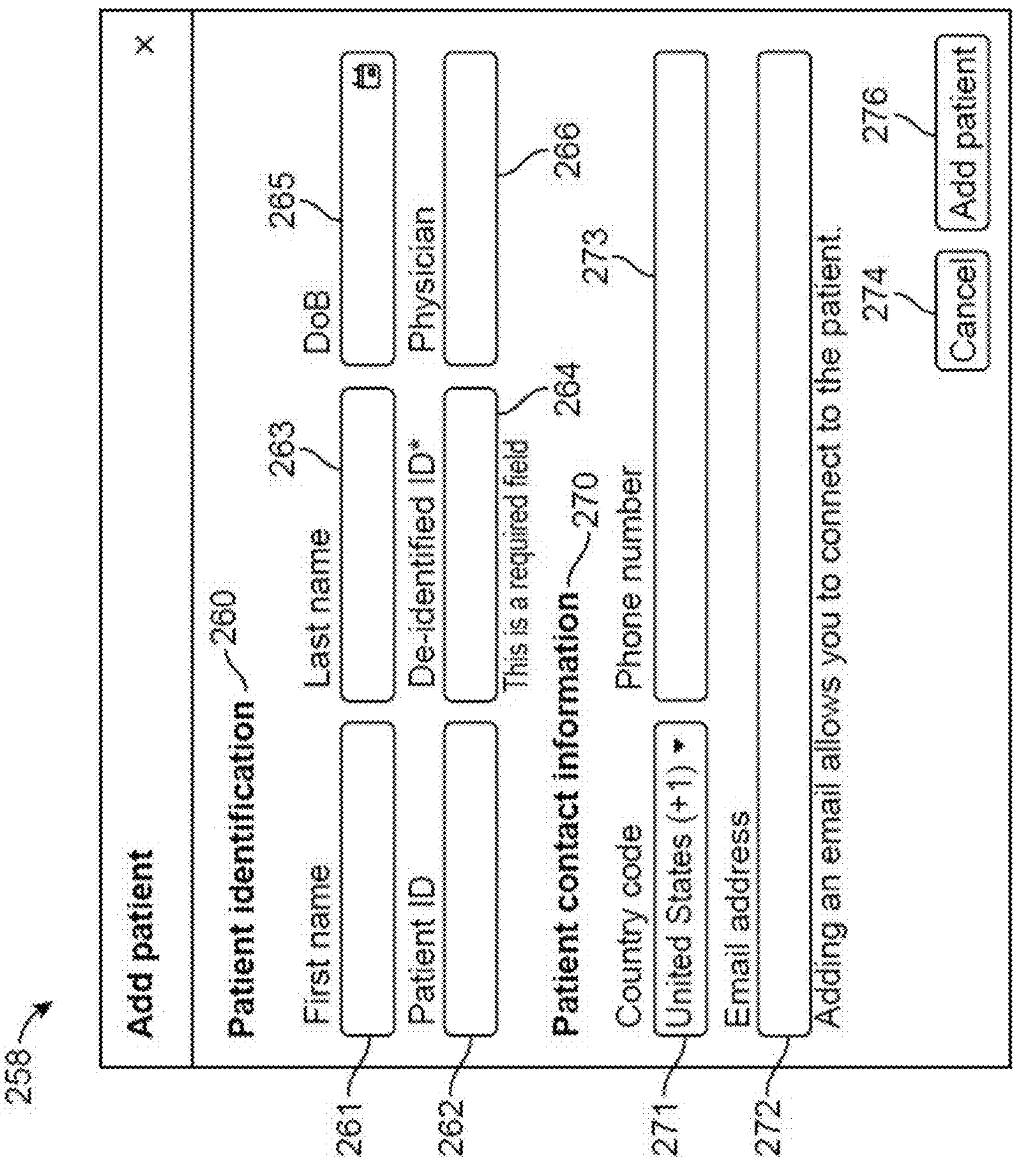

FIG. 4I is a block diagram schematically representing an example GUI portion 258 for patient care. The GUI portion 258 is an example implementation of a display from selection of the add patient icon 213 on GUI portion 200 of FIG. 4C and/or from any other GUI portions containing an add patient icon 213 in the banner, such as GUI portion 250 of FIG. 4E. As shown, in some examples, the GUI portion 258 is populated using, and/or displays, the patient identification region 260, which the clinician may use to input patient data into a plurality of input fields (or regions) 261, 263, 265, 262, 264, 266 (and which may include at least some of the patient identifying region 214 described above). For example, the clinician may input a first name of the patient, a last name of the patient, a DOB, a patient ID, a de-device ID which identifies the IMD and/or other patient communication devices, and a physician name (which may be the clinician or another clinician) into the input fields 261, 263, 265, 262, 264, 266. The GUI portion. 258 may further include patient contact region 270, which the clinician inputs data into a plurality of input fields 271, 273, 272. For example, the clinician may input a phone number including a country code and an email address into input fields 271, 273, 272. The input fields may include blank spaces in which data may be entered into, dropdown boxes to select options, and/or select boxes, among other types of fields. In some examples, the GUI portion 258 is further populated using, and/or displays, a cancel icon 274 which is selectable to cancel adding of a patient and an add patient icon 276 which is selectable to add the patient to a patient listing, such as the patient listing 222 illustrated by the GUI portion 200 of FIG. 4C.

Figure 4J:
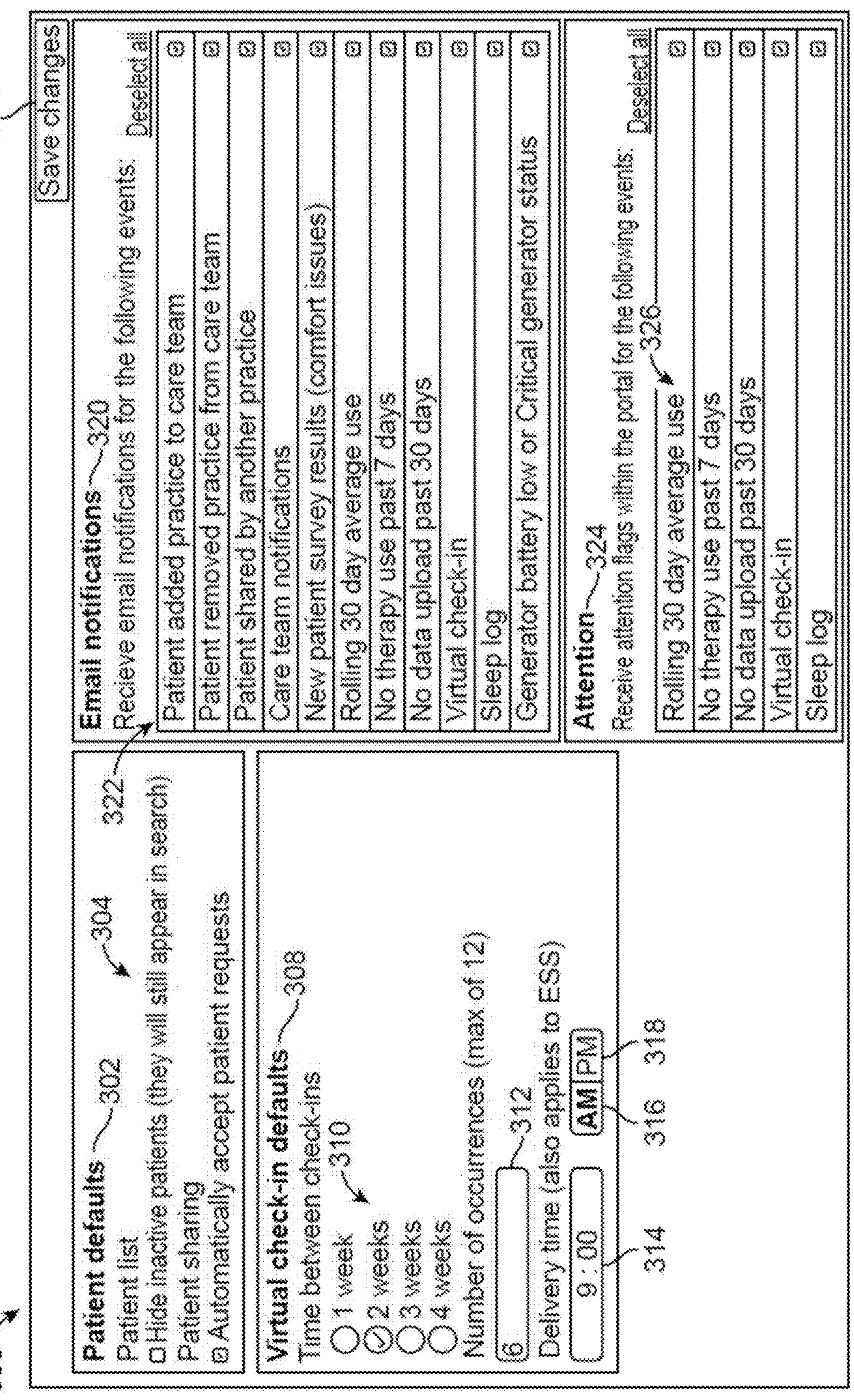

FIG. 4J is a block diagram schematically representing an example GUI portion 300 for patient care. The GUI portion 300 is an example implementation of a display from selection of the settings icon 211 on GUI portion 200 of FIG. 4C and/or from any other GUI portions containing a settings icon 211 in a banner. As shown, the GUI portion 300 may be populated using, and/or displays: (i) a patient default settings region 302, (ii) a virtual check-in default settings region 308, (iii) an email notification settings region 320, and/or (iv) an attention settings region 324, which the clinician may adjust or add data to via inputs into a plurality of input fields 304, 310, 322, 326. For example, the clinician may set different settings by selecting input fields 304, 310, 322, 326, e.g., selecting or deselecting boxes and/or inputting data. As a particular example, the clinician may adjust patient default settings in the patient default settings region 302 by selecting or deselecting boxes associated with the respective input fields 304 (e.g., hide inactive patients, automatically accept patient requests). In some examples, the clinician can adjust virtual check-in default settings in the virtual check-in default settings region 308 by selecting or deselecting boxes associated with the respective input fields 310 (e.g., time between check-in selected from different options of 1 week, 2 weeks, 3 weeks, or 4 weeks, a maximum number of occurrence 312, delivery time 314, and am or pm 316, 318). In some examples, the clinician can adjust email notification settings in the email notification settings region 320 by selecting or deselecting boxes associated with the respective input fields 322 and adjust attention settings or flags in the adjust attention settings region 324 that are associated with the different filters and which visually identify non-compliant patients by selecting or deselecting respective input fields 326 (which turns on or off different filters). The GUI portion 300 may be further populated using, and/or displays, a save changes icon 305 which is selectable to save the clinician inputs.

Figure 4K:
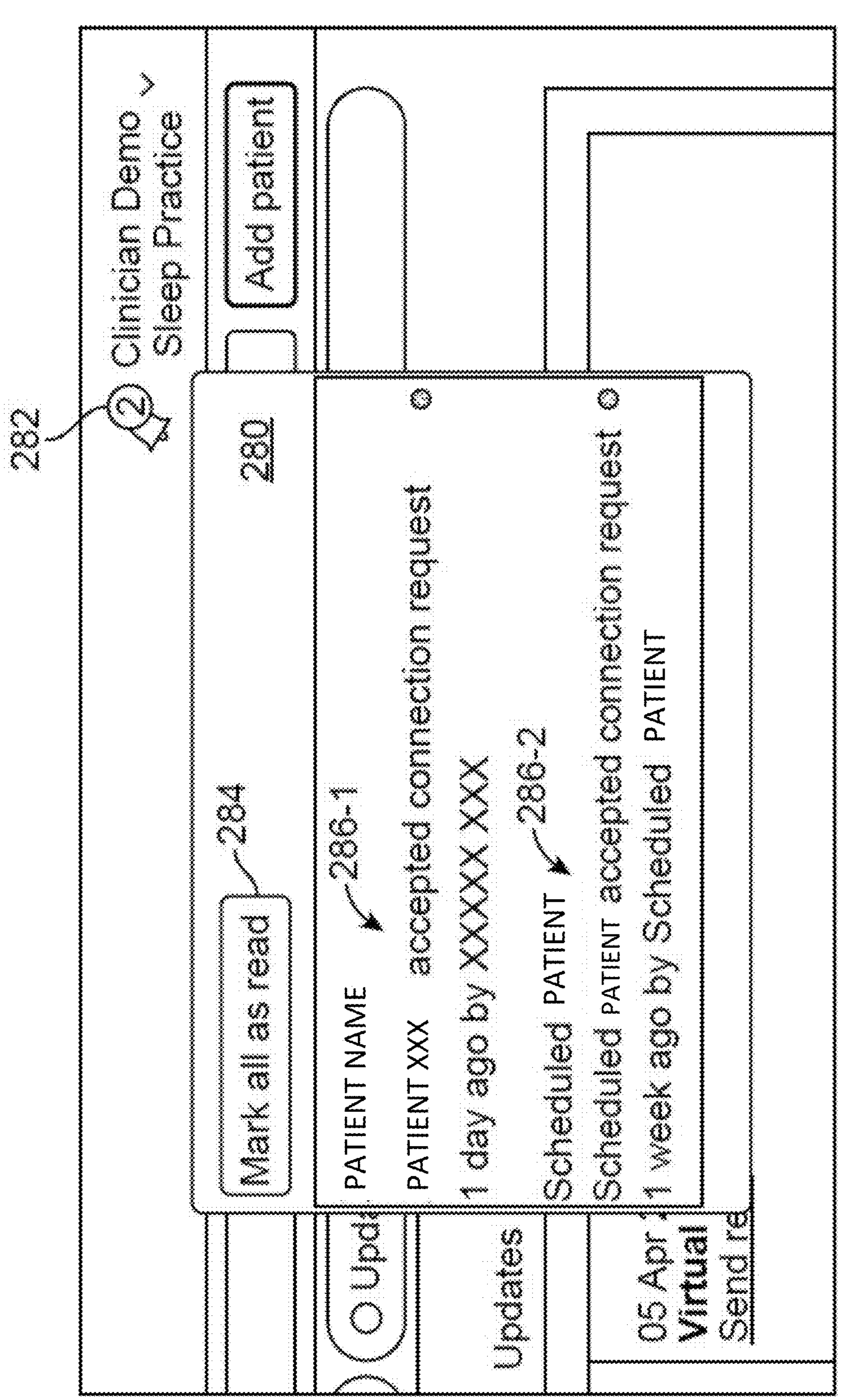

FIG. 4K is a block diagram schematically representing an example GUI portion 280 for patient care. The GUI portion 280 is an example implementation of a display from selection of the alarm icon 282 on GUI portion 200 of FIG. 4C (which is not illustrated by FIG. 4C but may be implemented as part of GUI portion 200) and/or from any other GUI portions containing an alarm icon 282 in a banner. As shown by FIG. 4K, in some examples and in response to user selection of the alarm icon 282, the GUI portion 280 is populated using, and/or displays, an expanded window that visually displays the different attentions, such as those selected in the attention settings region 324 of the GUI portion 300 of FIG. 4J. For example, the GUI portion 280 is further populated using, and/or displays, different attentions 286-1, 286-2 and an icon 284 which marks the attentions as read.

Figure 4L:
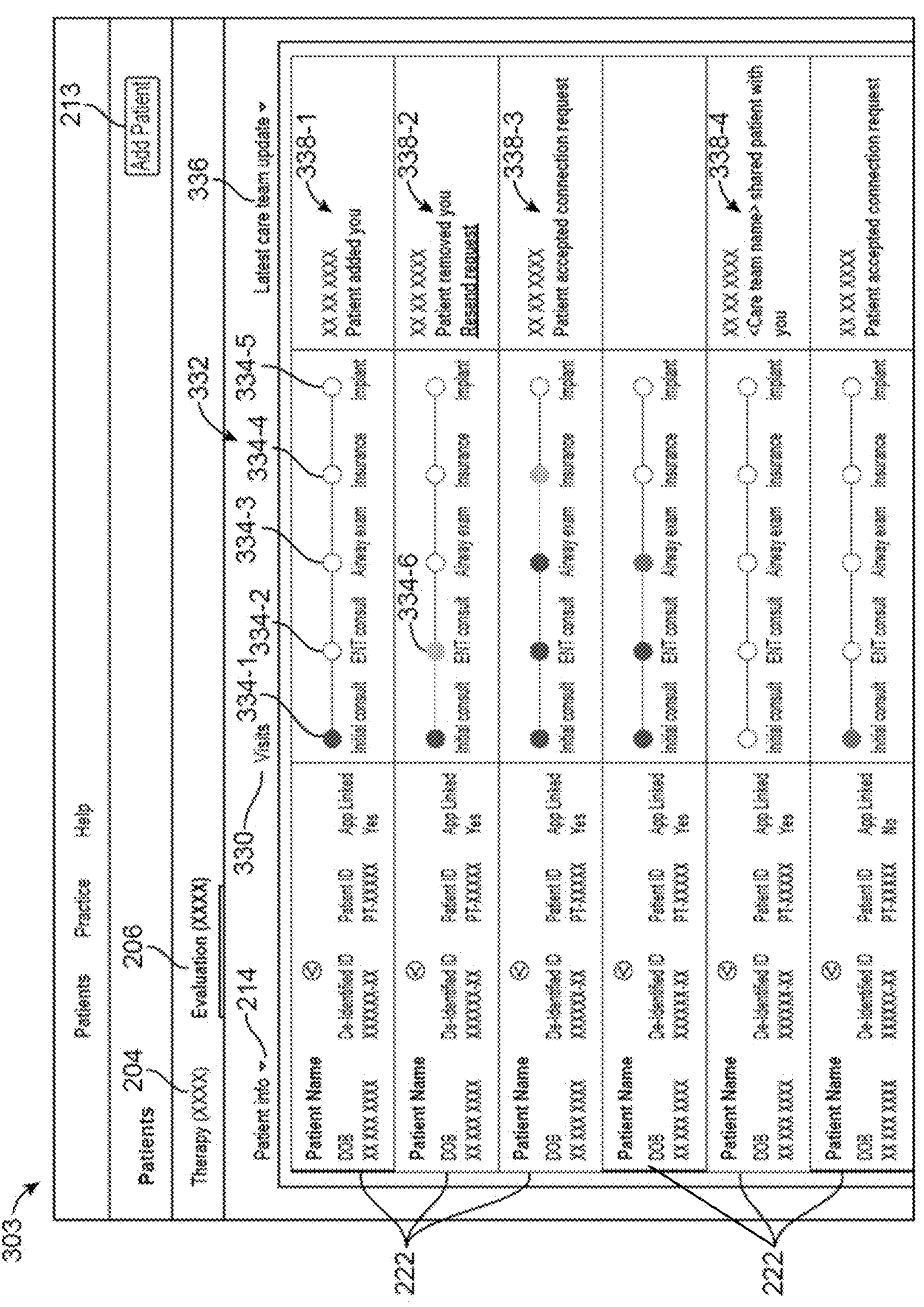

FIG. 4L is a block diagram schematically representing an example GUI portion 303 for patient care, which comprises at least some of substantially the same features and attributes of the GUI portion 200 of FIG. 4C, except being an example implementation in response to selection of the evaluation icon 206 instead of the therapy icon 204. FIG. 4L represents an example implementation upon selection of the evaluation icon 206, in which the GUI portion 303 is populated using, and/or displays, a patient identifying region 214 and a visit region 330 for a group of example patient listings 222 (e.g., patient record). In some examples, the patient identifying region 214 is populated using, and/or displays, at least some of the same type of information as previously described in connection with FIG. 4A. In some examples, each patient listing 222 may further comprise the visit region 330 which may be populated using, and/or may display, timeline graph 332 with different types of visits (e.g., Initial consult 334-1, ENT consult 334-2, Airway exam 334-3, Insurance consult 334-4, and Implant 334-5) and visual indication of the status of each respective visit within the graph 332. In the particular example, each of the different types of visits are illustrated for each respective patient of the patient listing 222 with the status being provided by a color or other visual indication associated with the visit being completed, as shown by 334-1, the visit not being completed or scheduled, as shown by 334-2, and/or the visit being scheduled but not completed, as shown by 334-6. It will be understood, of course, that for the many different types of patient care which may be provided, the types of visit may vary greatly and accordingly the types of visits (e.g., ENT consult, Airway exam) shown here are merely examples and are not limiting.

As further shown in FIG. 4L, GUI portion 303 may further be populated using, and/or displays, for each patient listing 222, "last care team update" region 336, by which the clinician may become informed of a therapy effectiveness indication, usage indication, etc., to help the clinician determine which patients are doing well and which may warrant faster or deeper attention (e.g., may be non-compliant). In some examples, the content of the region 336 for each patient listing 222 may be sorted (manually or automatically) per the at least one filter for different classes of the plurality of patients and/or may be flagged (manually or automatically) per the at least one filter, in a manner similar to that previously described for GUI portion 200 in associated with FIG. 4C. The "last care team update" region 336 may include similar or identical data to the therapy-related status update data, as previously described, and as shown at 338-1, 338-2, 338-3, 338-4.

Figure 4M:
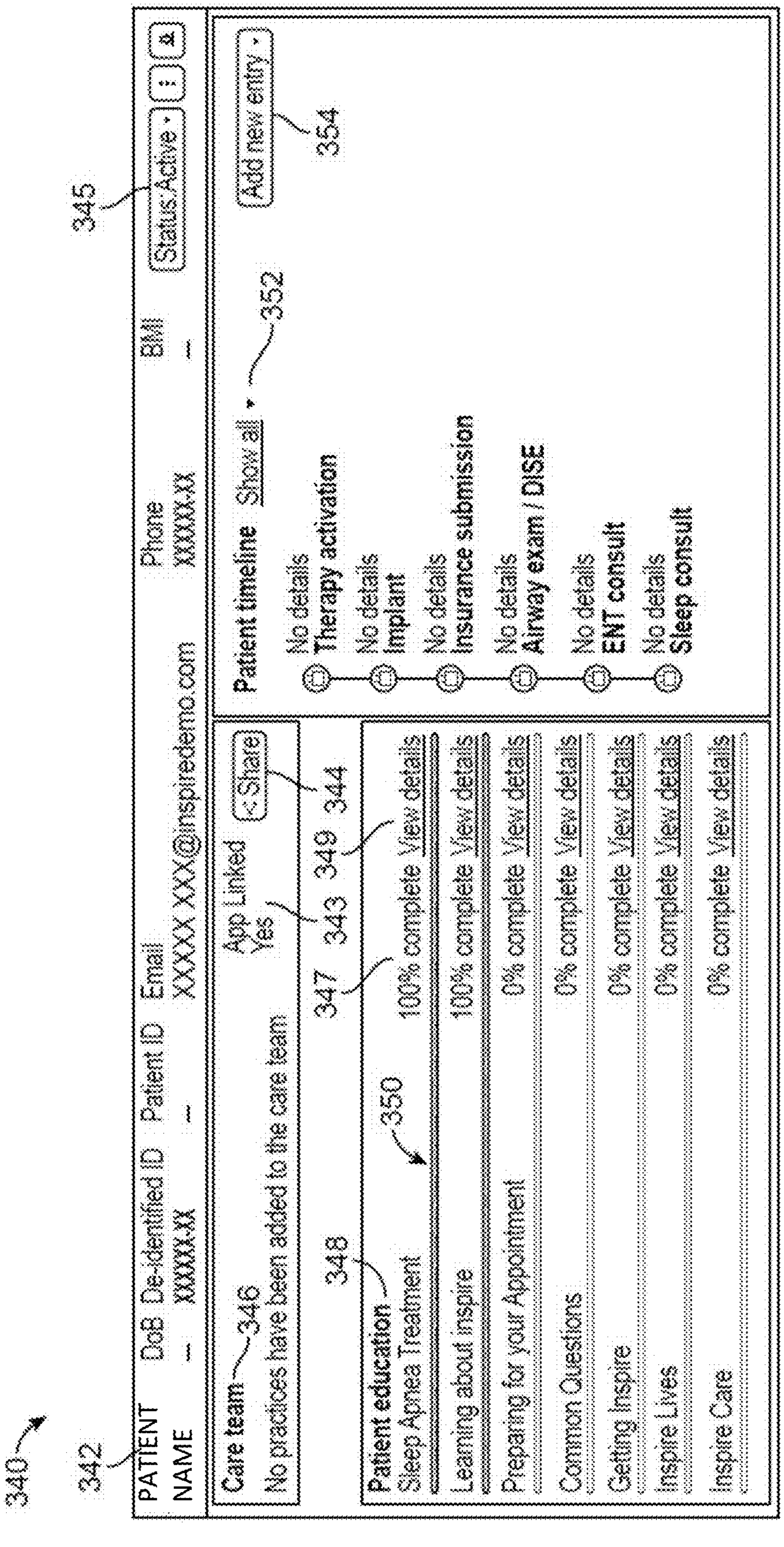

FIG. 4M is a block diagram schematically representing an example GUI portion 340. As shown in FIG. 4M, the GUI portion 340 provides an example implementation of a GUI viewable by a clinician upon selecting, for further review, one of the patient listings 222 in GUI portion 200 or GUI portion 303 of FIGS. 4C or 4L, or from any of the filtered patient listings 251, 253, 255, 257 of the GUI portions 250, 252, 254, 256 of FIGS. 4E-4H. The particular patient listing 342 may be selected for ordinary review or because the particular patient listing 342 was brought to the immediate attention of the clinician because it was filtered and/or visually flagged (in the manner previously described) to become conspicuously noticeable to the clinician in viewing one of the GUI portions 180, 200, 250, 252, 254, 256, 303.

As shown in FIG. 4M, in some examples, the GUI portion 340 is populated using, and/or displays, a banner with an individual patient listing 342 which lists the patient's name or other unique identifying information. In some examples, the banner area also may be populated using, and/or display, a status indicator 345 to indicate that the patient listing 342 is displaying patient evaluation information, such as but not limited to evaluating whether the patient is suitable for a particular type of therapy. In the case of SDB, the evaluation may be regarding whether the patient is a suitable candidate for upper airway stimulation, CPAP, or other types of therapy. With this in mind, as shown in FIG. 4M, in some examples, the GUI portion 340 may be populated using, and/or display, a patient timeline region 352 which includes a listing of several different evaluation milestones. Each milestone may correspond to a particular medical procedure, examination, consultation, or relate to other actions such as payment information (e.g. insurance accepted), which may be associated with the described visits. Each listed milestone also may comprise an indication of whether the particular milestone was completed. In some examples, at least some therapy-related milestones may be related to treating SDB, such "implant" and "activation and tuning". In a particular example, evaluation milestones relating to care for SDB may comprise initial consultation, EarNoseThroat (ENT) consultation, Airway Exam (Drug Induced Sleep Endoscopy—DISE), Insurance submission, Implant (surgical implantation of an IMD), and Activation and Tuning (of the IMD).

Among other features, the patient timeline region 352 may conveniently provide a summary and sequence by which a clinician may immediately recognize which evaluation milestones have been met by the patient and which milestones have yet to been achieved. Accordingly, in some examples, the patient timeline region 352 aids the clinician in quickly determining on what path to proceed to help the particular patient, and/or may help the clinician to quickly determine which care team member to communicate with to facilitate progression of the patient through the various milestones. The clinician may select one of the listed milestones to be taken to another GUI portion to obtain more detailed information regarding the selected milestone. As an example, upon selection of the initial consult milestone or the add new entry icon 354, the clinician is taken to GUI portion 650 in FIG. 5G, which is further described herein.

In some examples, the patient timeline region 352 also may facilitate patient care by the device manufacturer (or servicer) upon that entity becoming aware of certain milestones which a particular patient or a sampling of patients may have trouble achieving, and then take action to facilitate better outcomes in completing such milestones.

As shown in FIG. 4M, the patient timeline region 352 of the GUI portion 340 may be populated using, and/or displays, an add new entry icon 354. The add new entry icon 354 may include a dropdown box with a list of entry types that may be added. Example entries include scheduling a virtual check-in for the patient to provide a patient survey, scheduling an appointment with the clinician, and adding an apnea-hypopnea index (AHI), among other entries. The add new entry icon 354 may be used to facilitate scheduling a virtual check-in or physical check-in.

The GUI portion 340 may further comprise a care team region 346 which is populated using, and/or displays, a listing of the particular care team providers (e.g., associated with devices 850 in FIG. 7) which are caring for the particular patient. Accordingly, via this region 346, a clinician may quickly determine the members of the care team. In some examples, region 346 also may be populated using, and/or display, an "app linked" indicator 343 to determine whether the patient and/or a care team member has communicatively linked into the cloud (and therefore the patient management system). In some examples, region 346 is further populated using a share icon 344 that enables initiation of sharing information with a care team member and/or confirmation of the ability of a care team member to share care information.

As further shown in FIG. 4M, in some examples, the GUI portion 340 is populated using, and/or displays, a patient education region 348, which displays the progress the particular patient has made in viewing different patient education indicators 350. In some examples, these patient education indicators 350 may be provided and displayed via the patient app on patient communication devices, while in some examples they may be viewable via other resources linked to the processing resource. Data from the patient's engagement with the patient education indicators 350 may be processed via the processing resource (e.g., cloud computing system) and provided for display in patient education region 348 of the GUI portion 340. In some examples, the patient education region 348 may display a degree of progress according to percentage completion based on a percentage and/or a bar-type graphing, as shown by 347. Further details can be viewed by selecting a view details icon 349.

Among other features associated with the patient education region 348, a clinician may quickly determine whether the patient is making adequate progress in patient education, which in turn, may facilitate the type and manner of care provided by the clinician. In addition, this progress information may be filtered, sorted, and/or flagged according to the at least one filter and/or the filter icons (as previously described in connection with FIGS. 4C and 4L) to help the clinician quickly identify a patient which may need more encouragement to complete their evaluations.

In any of the GUI portions illustrated herein, such as those illustrated by FIGS. 4A-4M, the order in which items appear may be different and/or may be selectively changed by user and/or the service provider providing the clinician portal. For example, the content order may change such as what content is on top, middle, and/or bottom of the display.

In various examples, a particular patient may be selected by the clinician on one of the GUI portions, and to provide a display of expanded information on the particular patient. Similar to that described by FIGS. 4C and 4L, different views may be provided for the particular patient by selecting the therapy report icon or a timeline icon on a banner. FIGS. 5A-5G are each a diagram schematically representing further example GUI portions associated with a clinician portal, which are patient specific.

Figure 5A:
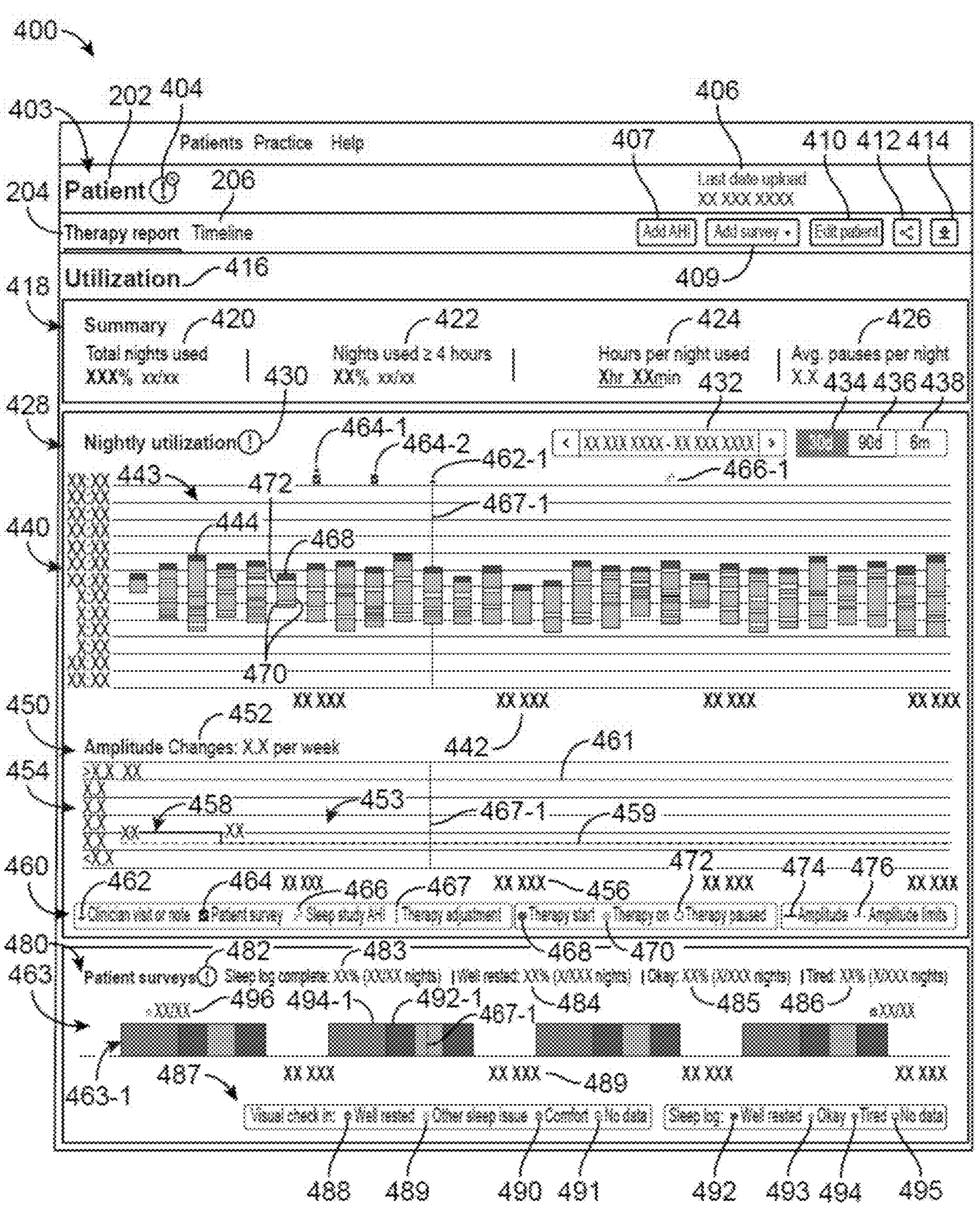

As shown in FIG. 5A, in some examples, the GUI portion 400 is populated using, and/or displays, a general region 403 and utilization region 416, which in turn includes a summary region 418, a nightly utilization region 428, an amplitude changes region 450, and a patient survey region 480. The GUI portion 400 may be further be populated using, and/or displays, selectable time period icons 434, 436, 438. For example, the GUI portion 400 may be displayed in response to selecting the particular patient from another GUI portion with a patient listing, such as GUI portion 200 of FIG. 4C, with the GUI portion 200 being the default display and/or being displayed in response to clinician selection of the therapy (report) icon 204 and the time period icon of 30 days icon 434.

In some examples, the general region 403 may be populated using, and/or display, data such as patient name, patient ID number(s), device IDs, and/or the like. In addition, in some examples, the general region 403 is populated using, and/or displays, icons which may act as a function to be activated and/or as a status indicator. For instance, the general region 403 may be populated using, and/or display, a therapy (report) icon 204, a timeline icon 206 (which may include the same icon as the evaluation icon 206), and a last upload indicator 406 which provides an indication of the last data update.

As further shown in FIG. 5A, in some examples, the general region 403 of the GUI portion 400 may be populated using, and/or display, an array of additional icons which are selectable to add entries or data, such as the add AHI icon 407, the add survey icon 409, the edit patient icon 410, the share icon 412, and the export icon 414. In some examples, upon activation via GUI portion 400, selection of at least some of the icons may cause certain information, status, etc. specific to each respective icon 407, 409, 410, 412, 414 to become displayed on GUI portion 400 or to become dormant on GUI portion 400, such as displaying another GUI portion 400 that was previously hidden. For example, selection of the add survey icon 409 may cause display (and operable access) of certain patient information related to a patient virtual check-in tool. Similar actions may occur in response to selecting the add AHI icon 407 and/or edit patient icon 410. The share icon 412 may cause selectable patient data to be shared from one clinician device (e.g., health care personnel at a sleep center) to another clinician device (e.g., health care personnel at a medical clinic) and the like. In some examples, the export icon 414 enables exporting patient data.

In some examples, the general region 403 is populated using, and/or displays, an attention icon 404 which may visually indicate the patient is non-compliant with at least one criteria associated with the at least one filter for different classes of the plurality of patients. The attention icon 404 may be selectable to cause display of additional information, such as identification of the non-compliance class and/or a degree of non-compliance.

In some examples, the above-noted icons 407, 409, 410, 412, 414, such as (but not limited to) the add survey icon 409, are further described later in association with at least FIG. 5F.

In some examples, the GUI portion 400 may further include various data, such as outcomes/effectiveness (e.g., performance) region, a setting region, and a programming region, which may in turn comprise a stimulation settings region, a sensing settings region, and a stimulation thresholds region, with such regions comprising comprise at least some of substantially the same features and attributes as shown by PCT Publication WO2022/182756.

The summary region 418 of GUI portion 400 is populated using, and/or displays, a summary of parameters, such as patient usage of an IMD over a time period. As noted above, the time period may be selectable via the time period icons 434, 436, 438. Some example time periods may comprise a week, a month (e.g., 30 days), a quarter (e.g., 90 days), a half year (e.g., 6 months), and the like. In some examples, the summary region 418 may be populated using, and/or may display, parameters including a total nights the IMD is used parameter 420, threshold utilization parameter 422 (e.g., nights used over threshold amount), average use parameter 424 (e.g., average hours used per night over the time period), and average pauses in use per night parameter 426.

Figure 7:
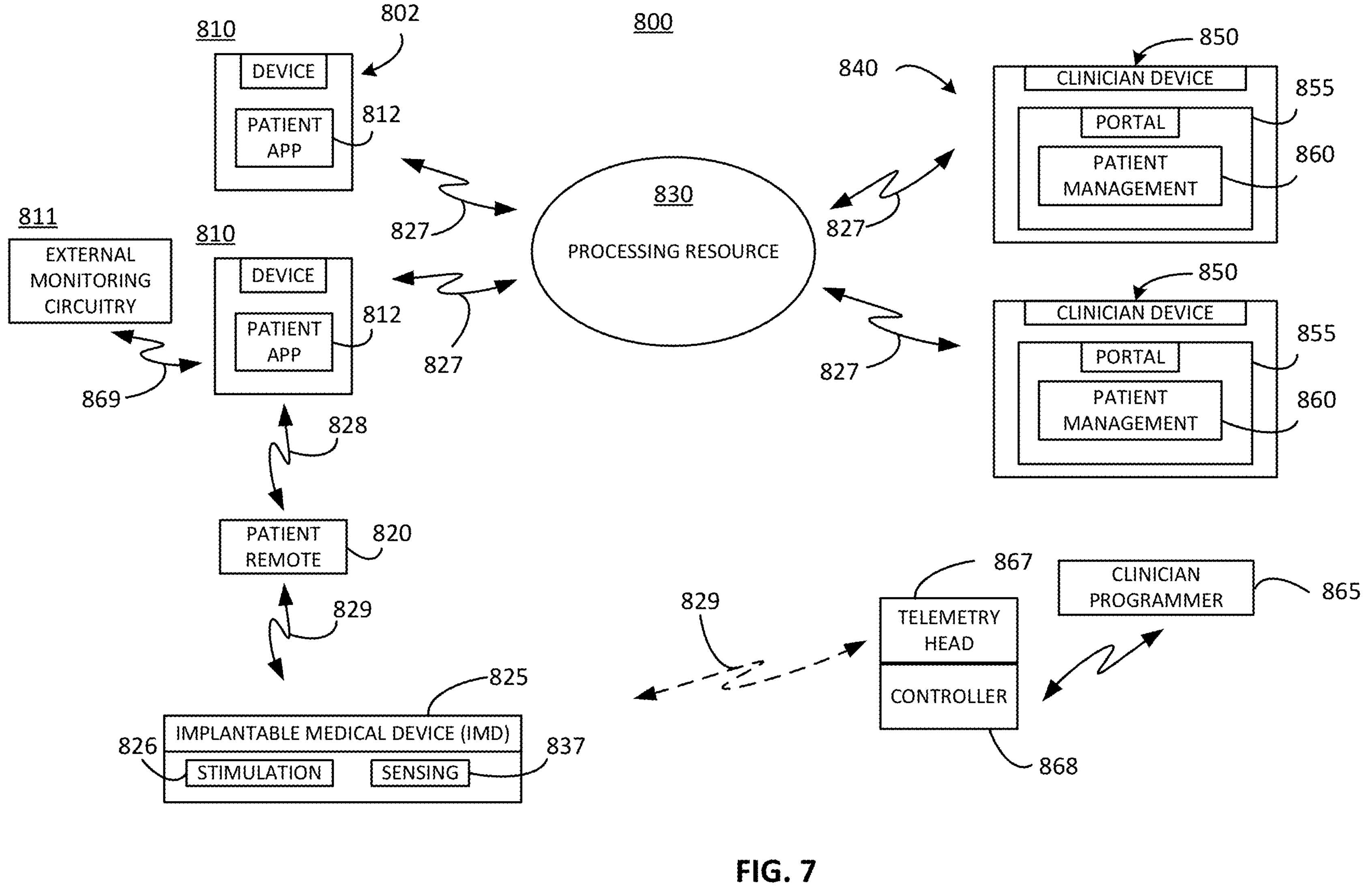
FIG. 7 is a block diagram schematically representing an example arrangement, deployable in an example method of (or as an example system for) patient management to facilitate patient care.

In some examples, a processing resource (e.g., of a cloud computing system, such as service provider 30 of FIG. 1 or processing resource 830 of FIG. 7) may track the various data displayed, such as the total nights which the patient used the stimulation therapy device within the selected time period (e.g., 30 days). This total may be displayed as a percentage, such as the number of days used relative to the total number of days within the selected period. One example implementation of the total nights the IMD is used parameter 420 is displayed in the summary region 418. As a particular non-limiting example, the total nights the IMD is used parameter 420 may include a percentage, such as 92%.

Similarly, in some examples, the processing resource tracks the number of nights (within the selected time period, e.g., 30 days) for which patient usage of the stimulation therapy met or exceeded a threshold. In some examples, the nights over threshold utilization parameter 422 may be expressed as nights relative to a threshold or nights relative to a criteria (e.g., used for more than "x" hours per night). In some non-limiting examples, the threshold may comprise a selectable amount of time, such as a number of hours (e.g., 4 hours, 5 hours, and the like). The amount of time may also be selected as a partial hour metric, such as 3.5 hours, 3.75 hours, 4.5 hours. In some examples, the selected time of 4 hours may be a significant indicator of a quantity of usage which may result in: significantly improved outcomes/effectiveness for the patient regarding their SDB. In some examples, it will be understood that the threshold may comprise "about" a selectable quantity (e.g., about 4 hours), which includes quantities of 3.8 hours, 3.85 hours, 3.9 hours, 3.95 hours, 4.05 hours, 4.1 hours, 4.15 hours, 4.2 hours, and the like, as examples. As a particular non-limiting example, the total nights the IMD is used parameter 420 may include a percentage, such as 96%.

In some examples, the processing resource may similarly track the average hours used per night and the average number of pauses in therapy per night parameters associated with the stimulation therapy device within the selected time period (e.g., 30 days). Both may be displayed as an average quantity, such as shown by 424 and 426 being displayed as parameters (of summary region 418).

In particular, for the average use parameter 424, the processing resource may track of a duration of usage per night, which may be expressed as an average, mean, and the like. As a particular non-limiting example, an average duration of stimulation therapy may include 6 hours and 48 minutes.

In some examples, per the above-noted average pauses per night parameter 426, the processing resource may track the number of times per night which stimulation therapy is paused by the patient, with the number of times being expressed as an average, mean, and the like. One example non-limiting example in which, for the days which therapy was used, the average number of pauses per night may include 0.9.

While each parameter alone may provide significant information regarding patient compliance, together parameters provide a more comprehensive picture of how well and how often the patient is using the stimulation therapy via the IMD. In some examples, the GUI portion 400 is populated using, and/or displays, various patient management information, which may include at least some of substantially the same features and attributes as described in PCT Publication WO2022/182756.

In some examples, the nightly utilization region 428 of GUI portion 400 is populated using, and/or displays, various icons 430, 432, 434, 436, 438, and a graph 443, sometimes herein referred to as "a nightly utilization graph". Icons 432, 434, 436, 438 may allow for selection of and/or display of the selectable time period of patient data to be reported, displayed, etc. A utilization attention icon 430 may be displayed in response to the patient being non-compliant with a criteria associated with the utilization filter.

As further shown in FIG. 5A, in some examples, a nightly utilization graph 443 may comprise a time scale 440 (e.g., hourly markers on a Y axis) relative to which each night's stimulation therapy usage may be displayed. The graph 443 also may comprise a selectable time period scale 442 (e.g., days, weeks, months, and the like on an X axis) for which the nightly usage data is displayed. More particularly, in some examples, the GUI portion 400 is displayed in response to the 30 day icon 434 being selected.

In some examples, graph 443 is populated using, and/or displays, an array (or plurality) of nightly usage indicators, as shown by the labeled indicator 444, which may take the form of bars, columns, and the like. In some examples, each nightly usage indicator comprises a start portion 468, therapy portion(s) 470, and pause portion(s) 472 (as applicable). Such indicators and indicator portions may provide more granular information, such as the exact time each therapy portion started, stopped, exact times at which the pause portion started, stopped, etc. As shown by FIG. 5A, via the nightly usage indicators, one can quickly visually see patterns of stimulation therapy usage.

As further shown in FIG. 5A, in some examples, the graph 443 also may be populated using, and/or displays, at least some of the indicators 464-1, 464-2, 462-1, 466-1, 467-1 which may be used to tag or mark various aspects of the nightly usage, such as when a sleep study (Sleep S, indicator 466) occurred, when a virtual check-in (patient survey, indicator 464) occurred, and the like. In some examples, the therapy adjustment indicator 467-1 may extend through each of the graphs 443, 453, 480 of the GUI portion 400.

In some examples, the GUI portion 400 may be populated using, and/or displays, a key 460 of the indicators, which may comprise a clinician visit or note indicator 462, a patient survey indicator 464, a sleep study AHI indicator 466, a therapy adjustment indicator 467, and/or other type indicators. The key 460 may provide additional information, such as indicating the different colors or other visual indications of the nightly usage indicator, e.g., the therapy start portion 468, therapy on 470, and therapy paused 472 portions. The key may additionally provide information on amplitude changes, such as identifying different lines representing amplitude 474 and amplitude limits 476.

In some examples, the amplitude changes region 450 of GUI portion 400 includes data indicative of stimulation therapy amplitude changes. One example implementation of the amplitude changes region 450 is shown by GUI portion 400 in FIG. 5A. In some examples, the amplitude changes region 450 may be populated using, and/or displays, a graph 453 which provides a plot 458 (shown as a solid line) of stimulation therapy amplitude over a selectable time period 456 (e.g., 30 days, 60 days, etc.). The graph 453 also may be populated using, and/or displays, lower and upper limits on an amplitude value selectable by the patient, which are shown via dashed lines as 459, 461, respectively, with the amplitude values 454 on the Y-axis and time period 456 on the X-axis.

In some examples, the amplitude changes region 450 may further be populated using, and/or displays, a patient changes/week indicator 452, which provides a metric of how often the patient is changing stimulation therapy amplitude within a time period (e.g., one week). This indicator may be expressed as an average, mean, or the like. The number of changes per week may sometimes provide an indication to a clinician of whether the patient finds the stimulation therapy to be comfortable, effective, etc.

The patient survey region 480 of GUI portion 400 may be populated using, and/or displays, a plurality of survey summary indicators 483, 484, 485, 486, an optional survey attention icon 482, and a graph 463. The survey summary indicators 483, 484, 485, 486, similar to the summary region 418, may include data tracked by the processing resource. For example, the indicators may provide parameters indicative of a percentage of sleep logs completed per night for the selected time period, as shown by indicator 483, a percent of nights the patient indicated they were well rested for the selected time period, as shown by indicator 484, a percent of nights the patient indicated they were okay rested for the selected time period, as shown by indicator 485, and a percent of nights the patient indicated they were tired for the selected time period, as shown by indicator 486. The survey attention icon 482 may be displayed in response to the patient being non-compliant with a criteria associated with the patient survey filter.

In some examples, the graph 463 of the patient survey region 480 may be populated using, and/or displays, an array (or plurality) of weekly patient survey indicators, as shown by the labeled indicator 463-1, which may take the form of bars, columns, and the like. In some examples, each weekly patient survey indicator comprises a plurality of portions for each patient survey of that week, such as illustrated by labeled portions 494-1, 492-1. Such indicators and indicator portions may provide more granular information regarding sleep status for the patient. As shown by FIG. 5A, via the patient survey indicators, one can quickly visually see patterns of sleep.

In some examples, the patient survey region 480 may be populated using, and/or displays, a key 487 of indicators, which may comprise visual indications of virtual check-ins, such as well rested 488, sleep issue 489, comfort 490, and no data 491. The key 487 may further include an indication of the meaning of the bars in the graph 463, such as visual colors or other indicators for well rested 492, okay 493, and no data 495, which may be populated in the graph 463 as shown by 496.

In some examples, the GUI portion 400 may be populated using, and/or displays, additional data. The additional data may include at least some of-substantially the same features and attributes as illustrated by PCT Publication WO2022/182756. For example, such data may include outcomes/effectiveness data, which provides a summary, details, etc., regarding various performance metrics regarding patient outcomes, therapy effectiveness (e.g., efficacy), etc. regarding the patient's stimulation therapy, data associated with a patient's AHI relative to various types of events and/or stages in the patient's progression, data associated with a patient's Epworth Sleepiness Scale (ESS) relative to various types of events and/or stages, a system information, generator summary data, therapy duration, stimulation levels and/or settings.

In some examples, the GUI portion 400 may be populated using, and/or may display, additional data such as, but not limited to, time spent in bed, time or amount of sleep, such as total sleep time and/or start and stop times. For example, the bars in the graph 463 of FIG. 5A may additionally or alternatively be used to display time spent in bed, total sleep time, start time, stop time, and/or sleep stage(s), and/or, in some examples, may be juxtaposed with the illustrated usage bars. Example sleep stages include awake, rapid eye movement (REM) (sometimes referred to as stage R), and non-rapid eye movement (NREM). In some examples, NREM sleep stages may include light sleep (e.g., NREM stages 1-2) and deep sleep (e.g., NREM stages 3-4).

Figure 5B:
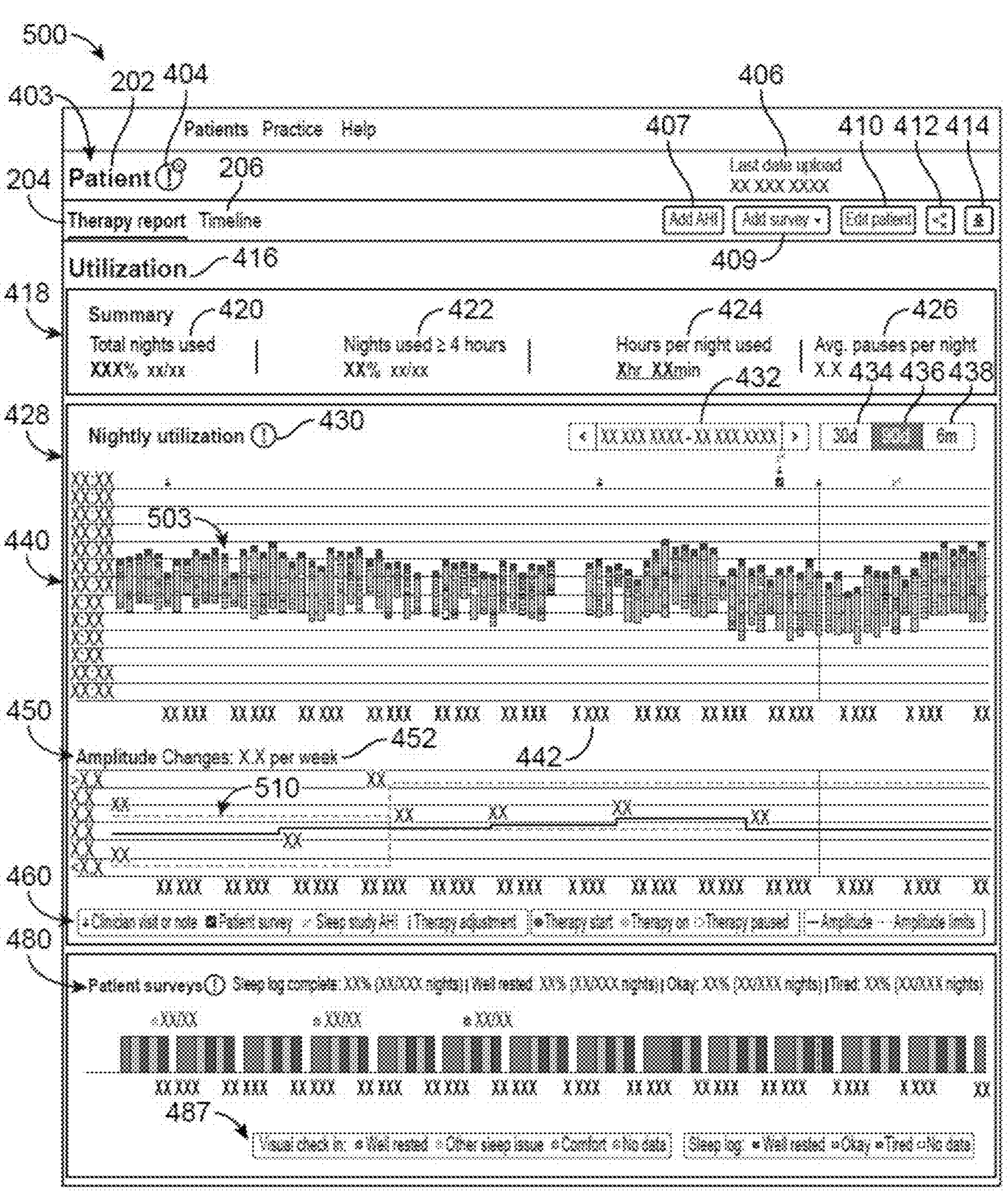

FIG. 5B is a block diagram schematically representing an example GUI portion 500 for patient care, which comprises at least some of substantially the same features and attributes of the GUI portion 400 of FIG. 5A, except being an example implementation in response to selection of the 90 day icon 436 on GUI portion 400 of FIG. 5A. As shown by GUI portion 500, in response to the selection, the GUI portion 500 is populated using, and/or displays, the general region 403 and the utilization region 416, which in turn includes summary region 418, a nightly utilization region 428, an amplitude changes region 450, and a patient survey region 480, which are populated using respective patient data for a time period of 90 days. The components of the general region 403 and utilization region 416 are substantially the same as described in connection with FIG. 5A and are not repeated for ease of reference, with the graph 503, 510, 463 being populated for a time period of 90 days instead of 30 days.

Figure 5C:
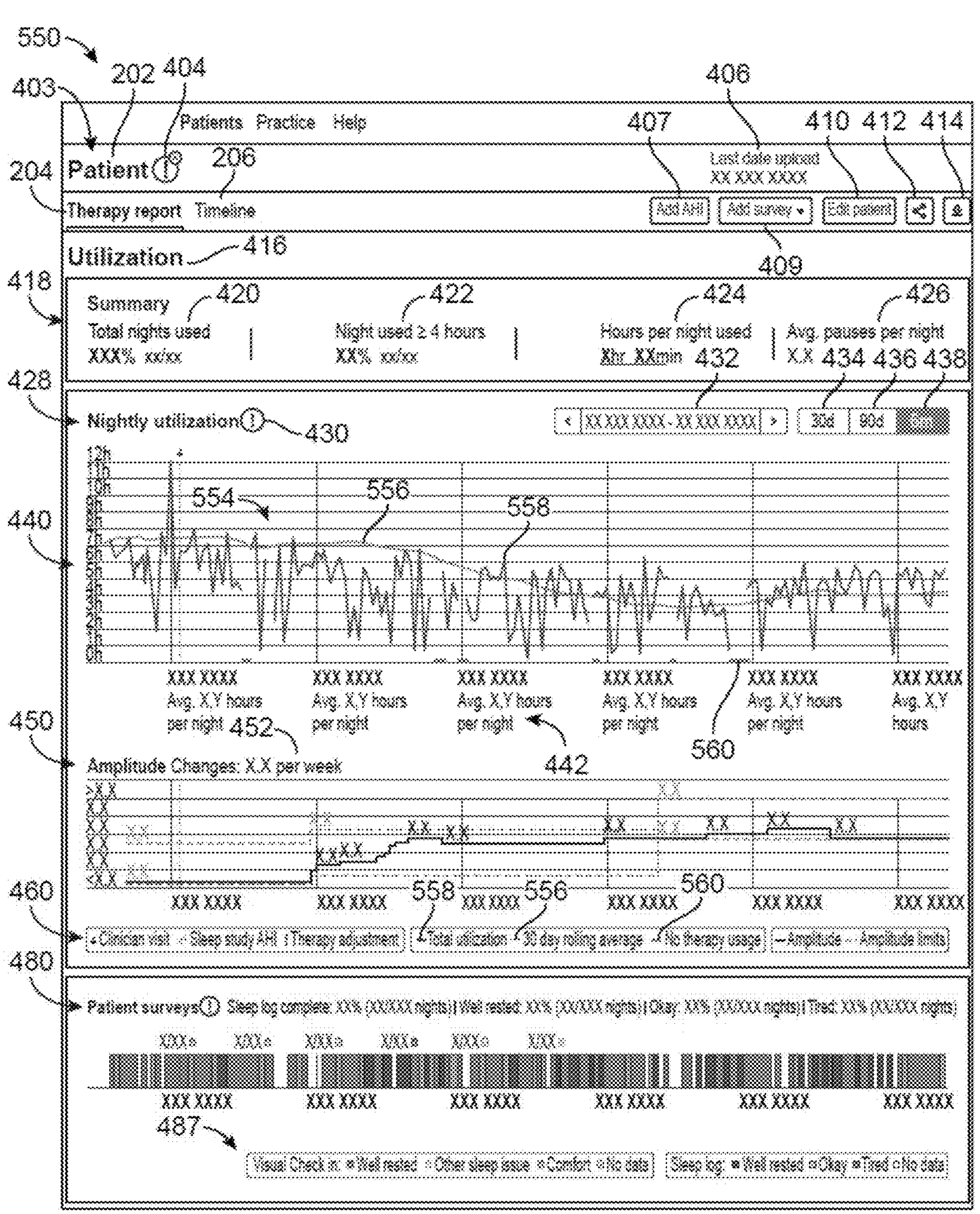

FIG. 5C is a block diagram schematically representing an example GUI portion 550 for patient care, which comprises at least some of substantially the same features and attributes of the GUI portion 400 of FIG. 5A and GUI portion 500 of FIG. 5B, except being an example implementation in response to selection of the 6 month icon 438 on GUI portion 400 of FIG. 5A and/or GUI portion 500 of FIG. 5B. As shown by GUI portion 550, in response to the selection, the GUI portion 550 is populated using, and/or displays, the general region 403 and utilization region 416, which in turn includes a summary region 418, a nightly utilization region 428, an amplitude changes region 450, and a patient survey region 480, are displayed with data for a time period of 6 months. As shown and in some examples, for the 6 month display, the graph 554 for the nightly utilization region 428 is a line graph rather than a bar graph to illustrate the additional amount of data, and which includes a thirty day rolling average line 556 and total utilization line 558, and with no line 560 representing no therapy use, as shown by the key 460. The components of the general region 403 and utilization region 416 are substantially the same as described in connection with FIG. 5A and are not repeated for ease of reference.

As shown by the GUI portions 500 and 550 of FIGS. 5B-5C, the different time periods may allow for the clinician to observe an amount and/or duration of utilization parameters (e.g., use over 4 hours each day) and trends (e.g., patterns) of the amount and/or duration of utilization over the time period, e.g., utilization has decreased or trended downward over time frame (e.g., 6 months). The non-compliance trend may be automatically populated and/or displayed (can select if that happens or not) so that the clinician may be drawn to see the non-compliance or lesser compliance trend.

Figure 5D:
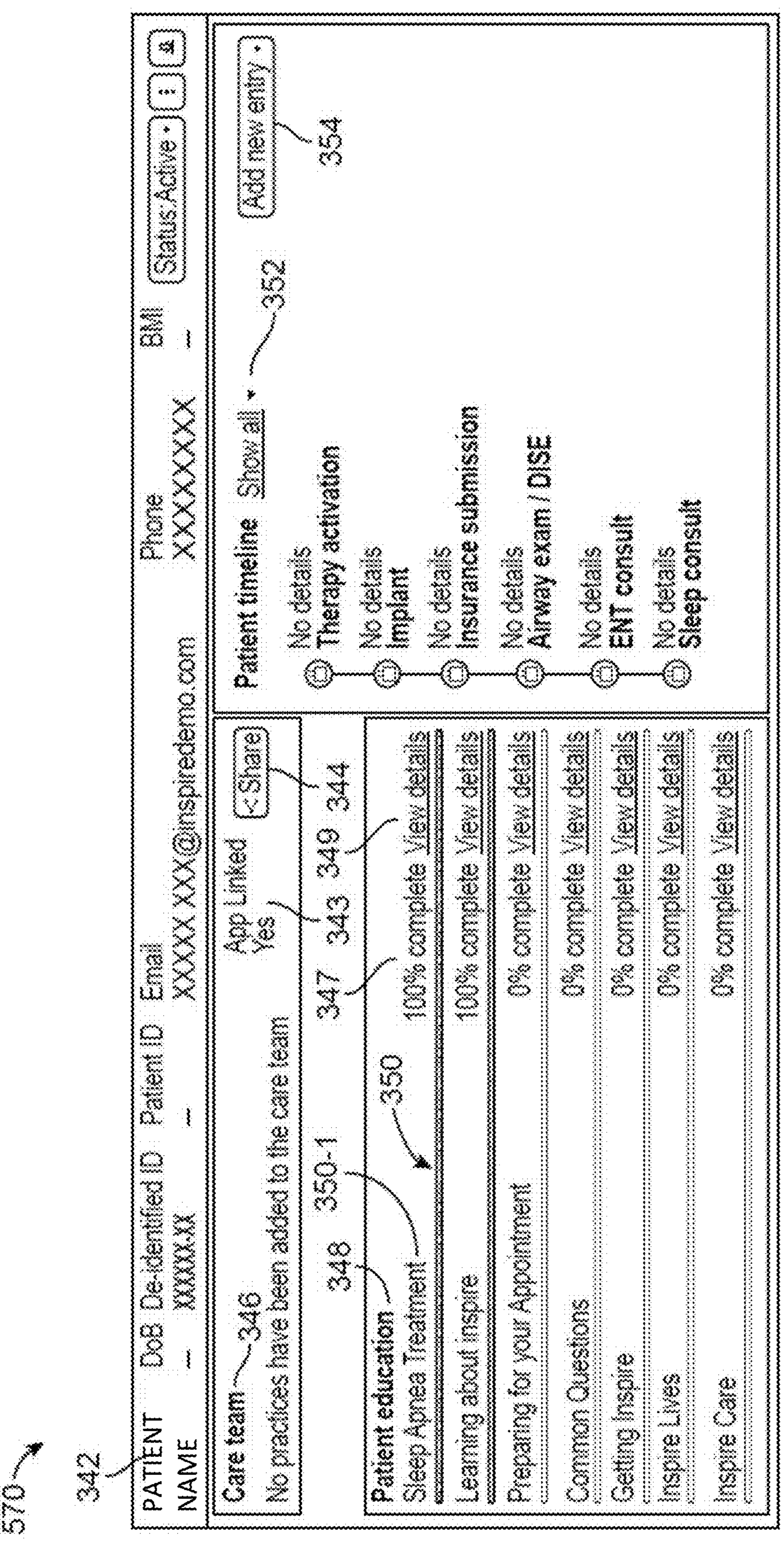

FIG. 5D is a block diagram schematically representing an example GUI portion 570 for patient care, which comprises at least some of substantially the same features and attributes of the GUI portion 400 of FIG. 5A, except being an example implementation in response to selection of the timeline icon 206 instead of the therapy icon 204. The data displayed in GUI portion 570 comprises substantially the same data as previously described for the GUI portion 340 in FIG. 4L, which is not repeated for ease of reference.

FIG. 5E is a block diagram schematically representing an example GUI portion 580 for patient care, which comprises at least some of substantially the same features and attributes of the GUI portion 570 of FIG. 5D, except being an example implementation in response to selection of one of the patient education indicators 350. For example, the particular patient educator indicator 350-1 is selected to cause the display of the GUI portion 580. In some examples and in response to the selection, the GUI portion 580 is populated using, and/or displays, various additional data 582, which was previously hidden. In some examples, each of the different patient education indicators 350 may be selected to expand the data displayed.

As shown in FIG. 5E, the GUI portion 580 may be populated using, and/or displays, an array of additional icons which are selected to add AHI icon 407, add survey icon 409, edit patient icon 410, share icon 412, and export icon 414, as previously described in connection with FIG. 5A. The add survey icon 409 may include a dropdown box with a list of entry types that may be added. Example entries include adding a scheduled virtual check-in for the patient to provide a patient survey or a physical check-in or consultation. The add survey icon 409 may be used to facilitate scheduling a virtual check-in or physical check-in.

In some examples, the patient timeline region 352 also may be populated using, and/or may display, a listing of patent virtual check-in records, with each listed record including a completion date. Upon selection of one of the virtual check-in records in region 352 of GUI portion 580, e.g., 352-1, the GUI portion 600 in FIG. 5F may be populated using, and/or displays, an expanded window 602 displaying the details of the selected virtual check-in. In some examples, GUI portion 600 collapses or hides the timeline or patient education regions 348, 352 to make room for the expanded window 602.

Figure 5F:
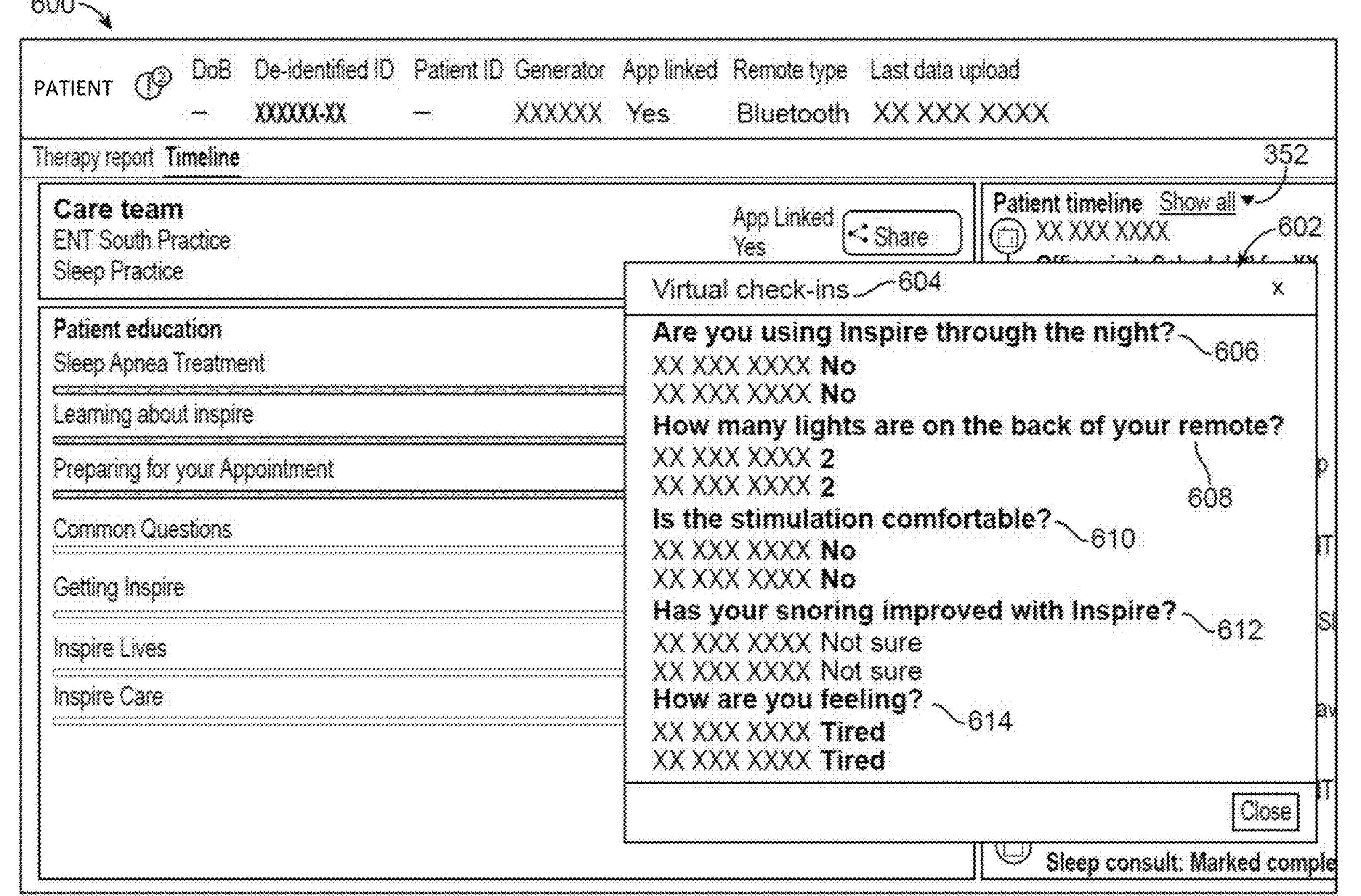

FIG. 5F is a block diagram schematically representing an example GUI portion 600 for patient care, which comprises at least some of substantially the same features and attributes of the GUI portion 570 of FIG. 5D, except being an example implementation in response to selection of one of the timeline indicators in the region 352, sometimes referred to as milestones. For example, the particular timeline indicator 352-1 may be selected to cause the display of the GUI portion 600, which includes an expanded milestone window 602. In some examples and in response to the selection, the GUI portion 600 is populated using, and/or displays, the expanded milestone window 602 which was previously hidden. For example, the virtual check-in 604 data provides further information on the patient survey answers, such as indication of use 606, verification of visual indicators on the remote 608, comfort 610, snoring 612, and sleep indicators 614. Examples are not so limited and may include additional variations. In some examples, each of the different timeline indicators in region 352 may be selected to expand the data displayed.

As shown by 604 in FIG. 5F, in some examples, the virtual check-in details include various automated queries and answers supplied by the patient from their engagement of the patient survey on the virtual check-in of the patient app 812 on device 810, as shown in FIG. 7. Moreover, the provided details may include the scheduled date. While the expanded window 602 within GUI portion 600 illustrates at least some example detailed queries and answers, a further description regarding such queries and answers as part of a patient survey may be provided.

It will be understood that upon selection of one of the other milestones, other expanded windows may be populated in GUI portion 600 with details particular to that milestone. For example, in response to selecting an initial consult milestone from the timeline, an expanded window may be populated using, and/or displays, scheduling details (e.g., date, completed, etc.), related files (e.g., patient assessment notes, images, etc.), a file upload input, and note input portion. The expanded windows may be referred to as pop-up windows.

Figure 5G:
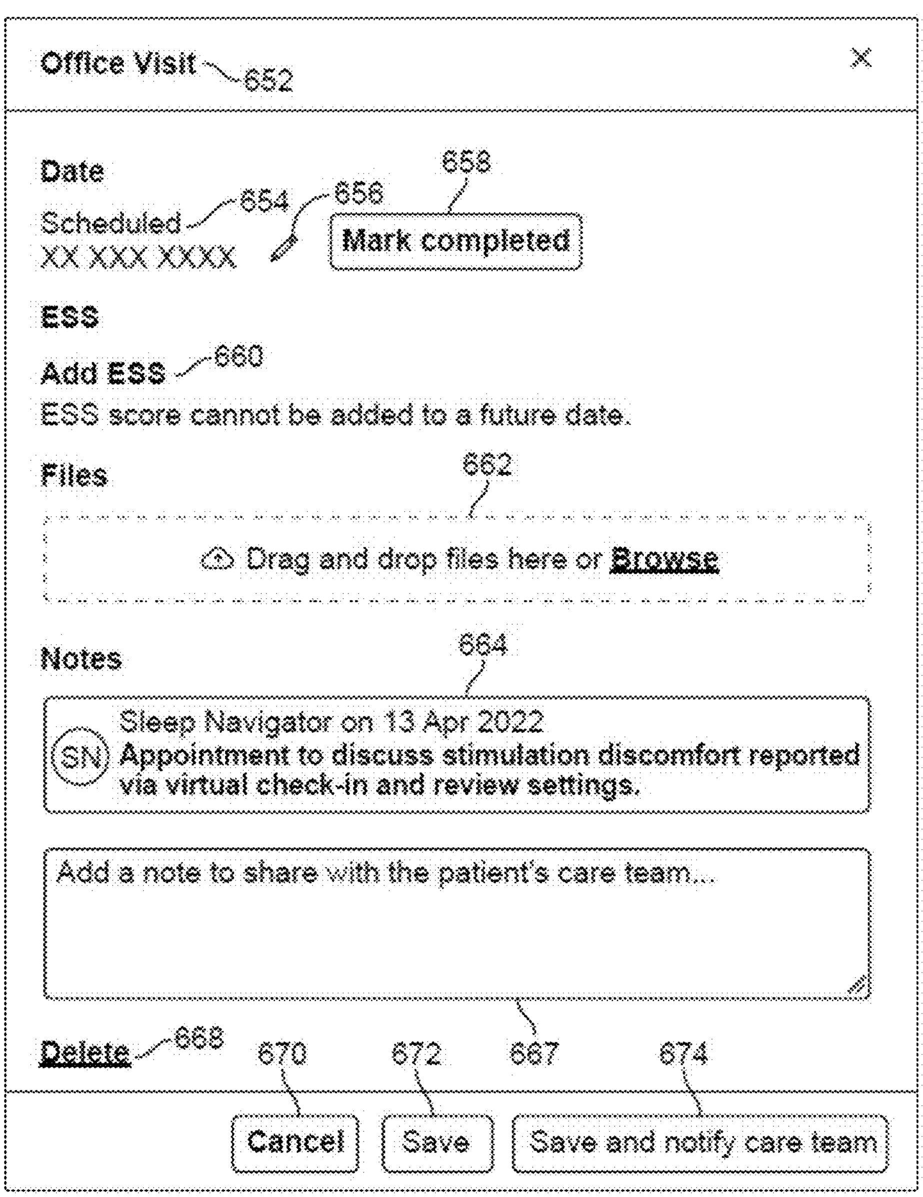

FIG. 5G is a block diagram schematically representing an example GUI portion 650 for patient care, which comprises at least some of substantially the same features and attributes of the GUI portion 570 of FIG. 5D, except being an example implementation in response to selection of the add new entry icon 354 of the GUI portion of FIG. 5D, which may be selected to add an entry, or one of the entries may be selected to add additional data. For example, the new entry icon 354 is selected to cause the display of the GUI portion 650. In response to the selection, the GUI portion 650 may be populated and/or displayed, which was previously hidden. For example, the GUI portion 650 is populated using, and/or displays, an office visit entry region 652 that displays a variety of icons and input fields 654, 660, 662, 664, 667, 668, which may be used to view the date of the entry (e.g., scheduled date icon 654, edit the date icon 656) and includes icons, such as a mark complete icon 658, an add ESS icon 660, a file drop box 662 to input files, a visual indication of entered notes 664, a notes input field 667 for clinician to input new notes, and/or a delete icon 667 to delete the entry. Other example icons include the cancel icon 670 to cancel the changes made, a save icon 672 to save changes made, and a save and notify care team icon 674 to save the changes and output a communication to another clinician-controlled communication device. Examples are not so limited and may include additional? variations. In some examples, each of the icons may be selected to expand the data displayed.

The above-described various features of the GUI portions, as driven via the various functions and parameters, provide a rich environment by which a clinician may manage patient care. For instance, in some examples, upon a clinician viewing the various displayed patient data in GUI portions of FIGS. 4A-4H regarding non-compliant patients of multiple different compliance classes which are visually highlighted or flagged, and GUI portions of FIGS. 5A-5C regarding nightly usage, amplitude changes, and/or patient survey answers, the clinician may make an assessment regarding patient symptoms, patient adherence, and/or therapy efficacy (e.g. patient outcomes). Based on the assessment, the clinician may order further patient education, changes to stimulation therapy programming, and the like, as desired. At least some further details regarding this information-rich environment for patient management are described in association with at least FIG. 7, among other examples throughout the present disclosure.

It will be understood that the data displayed, accessed, input, etc. on the various GUI displayed herein may be presented in a wide variety of formats, with the examples shown being just one example format. In some examples, any item shown in a particular GUI portion(s) may be selectively included for display or excluded from display. Likewise, in some examples, a new GUI portion may be constructed via selecting items from one GUI portion to be selectively mixed/matched with selected items from another GUI portion.

Figure 6:
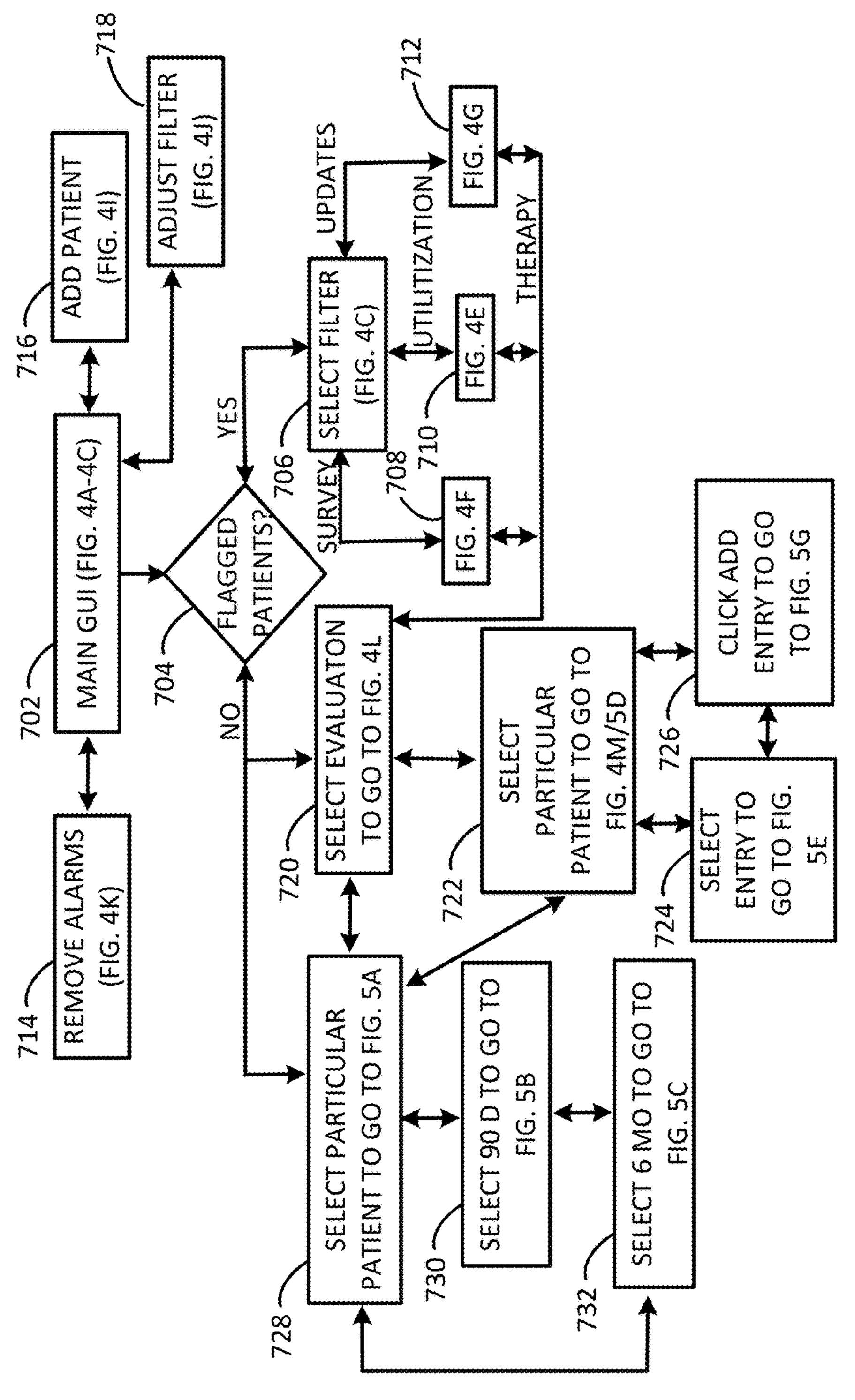
FIG. 6 is a flow diagram schematically representing example transitions through GUI portions.

FIG. 6 is a flow diagram schematically representing example transitions through GUI portions. The flow diagram may be implemented using the GUI portions associated with FIGS. 4A-4M and 5A-5G. The flow diagram represents an example process 700 of transitioning through the different GUI portions associated with a clinician portal and by a clinician.

In some examples, the clinician may log into a clinician portal on a clinician-controlled communication device, which is in communication with or includes a processing resource that tracks patient data, such as illustrated further herein. The clinician-controlled communication device may communicate with the processing resource to authenticate the clinician and retrieve patient data associated with patients of the clinician. In response, as shown at 702 of FIG. 6, the clinician-controlled communication device may display a main GUI, such as the main therapy GUI portion 180, 181, and/or 200 in FIGS. 4A-4C.

On the main GUI, the clinician may select a variety of different icons to transition to a different GUI portions. For example, the clinician may select: (i) the alarm icon (282 of FIG. 4K) to transition to the GUI portion 280 of FIG. 4K to view and/or remove alarms or attentions, as shown at 714; (ii) select the add patient icon (213 of FIG. 4C) to transition to the GUI portion 258 of FIG. 4I, as shown at 716; and/or (ii) select the settings icon (211 of FIG. 4C) to transition to the GUI portion 300 of FIG. 4J and to adjust settings, such as adjusting filter or attention settings, as shown at 718.

In some examples, as shown at 704, the main (therapy) GUI portion 180, 181 and/or 200 of FIGS. 4A-4C may display flagged patients which are non-compliant with one or more criteria. For example, in response to visual display of non-compliant patients, the clinician may select at least one filter icon (208, 210, 212 of FIG. 4C), as shown at 706. In some examples, in response to selecting the utilization filter icon 208 in GUI portion 200 of FIG. 4C, the GUI portion 250 of FIG. 4E is displayed, as shown at 710 of FIG. 6. In response to selecting the patient survey filter icon 210 in GUI portion 200 of FIG. 4C, the GUI portion 252 of FIG. 4F may be displayed, as shown at 708 of FIG. 6. In response to selecting the update filter icon 212 in GUI portion 200 of FIG. 4C, the GUI portion 254 of FIG. 4G may be displayed, as shown at 712 of FIG. 6. In considering process 700 in FIG. 6, it will be understood that in some examples multiple filter icons 208, 210, 212 in GUI portion 200 of FIG. 4C and in different combinations may be selected at the same time.

By clicking on the different filter icons and/or in different combinations, the clinician may efficiently view non-compliant patients, which may be used to improve patient compliance. For example, the clinician may efficiently and effectively become informed of potential issues which may contribute to patient compliance or adherence, therapy efficacy, and improved patient outcomes, and may communicate with the patient to pro-actively resolve or mitigate the issues and/or to prevent the patient from becoming non-compliant and/or to improve patient compliance.

In some examples, the clinician may select the evaluation icon 206 from any of the described GUI portions, e.g., 180, 200, 250, 252, 254, to transition to the GUI portion 303 of FIG. 4L or GUI portion 340 of FIG. 4M, as shown at 720 of FIG. 6 and as further described herein.

As shown at 720, the clinician may select the evaluation icon 206 from one of the GUI portions, such as from the GUI portion 180 and/or 200 of FIGS. 4A-4C. In response, the GUI portion 303 of FIG. 4L may be displayed. The clinician may select a particular patient from the GUI portion 303 of FIG. 4L, in which the evaluation icon is selected to transition to the GUI portion 340 of FIG. 4M or GUI portion 570 of FIG. 5D, as shown at 722. From the GUI portion 340 of FIG. 4M or GUI portion 570 of FIG. 5D, the clinician may select the add new entry icon 354 to transition to GUI portion 650 of FIG. 5G and to add a new office visit entry for the patient, as shown at 726 of FIG. 6. In some examples, from the GUI portion 340 of FIG. 4M or GUI portion 570 of FIG. 5D, the clinician may select one of entries in the patient education region 348 to transition to GUI portion 580 of FIG. 5E which illustrates further data about the entry associated with the indicator 350-1, as shown at 724. In some examples, the clinician may select one of the timeline entries from the timeline region 352 from the GUI portion 340 of FIG. 4M or GUI portion 570 of FIG. 5D to display the GUI portion 600 illustrated by FIG. 5F.

From the main therapy GUI screen, e.g., GUI portion 180 and/or 200 of FIGS. 4A-4C, or from the main evaluation GUI screen, e.g., GUI portion 303 of FIG. 4L, or from a patient specific GUI screen with a timeline icon selected, the clinician may select a particular patient and/or select the therapy icon 204 to transition to the GUI portion 400 of FIG. 5A that displays 30 day utilization data, as shown at 728 of FIG. 6. The clinician may transition to and/or between GUI portion 500 of FIG. 5B and GUI portion 550 of FIG. 5C, which respectively display 90 day utilization data and 6 month utilization data, as shown at 730 and 732 of FIG. 6. The different time periods may provide the clinician with better understanding of issues and/or causes of non-compliance, resolutions to improve compliance, and/or prediction of future non-compliance.

FIG. 6 is provided as a non-limiting example and a clinician may transition through the different GUI portions in different orders and/or sequences than illustrated. For example, the clinician may begin at different blocks and/or activate or engage different GUI portions (e.g., subsets or all).

FIG. 7 is a block diagram schematically representing an example arrangement 800, deployable in an example method of (or as an example system for) patient management to facilitate patient care. In some examples, the arrangement 800 may be used to implement the flow diagrams of FIGS. 3A-3D and FIG. 6 and/or to populate and display the GUI portions associated with FIGS. 4A-4M and 5A-5G. In some examples, the arrangement 800 may include an implementation of arrangement 20 of FIG. 1 and/or device 25 of FIG. 2. As shown in FIG. 7, example arrangement 800 may comprise an array 802 of patient communication devices 810, each of which host a patient app 812 relating to patient care. The devices 810 may sometimes be referred to as computing devices, patient computing devices, and the like. The patient app 812 may provide patient education, enable communication with a caregiver, device servicer, device manufacturer, etc. In some examples, the patient app 812 may communicate patient usage information (and some related therapy metrics) to a clinician-controlled device 850 (e.g., care entity), device servicer or service provider, device manufacturer, etc. In some examples, at least some of the patient communication devices 810 comprise a mobile computing device, such as a mobile phone, tablet, smartwatch, etc. which has a GUI to provide for operation of, and display of, the patient app 812.

In some examples, the patient app 812 may comprise a virtual check-in app or function to facilitate a patient checking in with a caregiver, such as a clinician, which may include at some of substantially the same features and attributes as described in the PCT Publication WO2022/182756. Among other functions and features, the patient app 812 (e.g., the virtual check-in app or function) may comprise a patient survey, which leads the patient through a series of questions (e.g., queries) regarding their use of their therapy device, how often they use the device, what may be preventing them from using the device, and the like. At least some example queries may include at some of substantially the same features and attributes as described in the PCT Publication WO2022/182756.

As shown in FIG. 7, in some examples, the example arrangement 800 may comprise an IMD 825. In some examples, the IMD 825 may be adapted for treating SDB and/or other patient conditions (e.g., cardiac, pelvic disorders, etc.). A patient remote 820 may communicate with the IMD 825 via a wireless communication protocol either directly or indirectly via an intermediary communication element (e.g., antenna, other), as illustrated by the directional arrows 828, 829. In some examples, such wireless communication may take the form of inductive telemetry and/or other wireless protocols such as (but not limited to) a Bluetooth® wireless protocol, infrared, near IR, etc. In some examples, the IMD 825 may comprise an implantable pulse generator (IPG) for generating stimulation therapy signals to be delivered to the patient via a stimulation element (e.g., electrode) within the patient.

In general terms, the patient remote 820 may enable a patient to have limited control over their stimulation therapy, such as turning the stimulation therapy on/off, pause, and/or increasing or decreasing the amplitude of stimulation within a lower and upper limit set by a clinician (and/or device manufacturer, supplier, etc.). In some examples, the patient remote 820 also tracks patient usage of these controls to enable a clinician, the patient, and others to learn about the patient's usage, therapy effectiveness, patient adherence, etc. In some examples, the patient remote 820 also may receive some information from the IMD 825 regarding stimulation metrics, sensing metrics, etc.

In some examples, the patient remote 820 is in communication with the patient app 812 such that patient app 812 on device 810 may receive the patient usage data from the patient remote 820, as well as whatever therapy, sensing, etc. information was communicated from the IMD 825 to the patient remote 820. In some examples, the communication between the patient remote 820 and the patient app 812 (on patient communication device 810) may occur wirelessly, as represented by directional arrow 828, via a number of wireless communication protocols such as, but not limited to, a Bluetooth® wireless communication protocol. In some examples, the communication between patient remote 820 and patient app 812 (on patient communication device 810) may occur via a wired connection.

As noted here and elsewhere, the patient app 812 may communicate data received from the patient remote 820 to one or more of the clinician-controlled devices 850 via processing resource 830 to facilitate patient management according to examples of the present disclosure. In some examples, the patient app 812 also may obtain some patient data through the patient's use of the patient app 812 which also may be communicated to the clinician-controlled devices 850 separately from, or integrated with, the patient usage data and therapy data from the patient remote 820 and/or IMD 825.

As further shown in FIG. 7, an example IMD 825 may comprise a stimulation component 826 and/or sensing component 837. In some examples, the stimulation component 826 comprises a stimulation engine to generate a stimulation signal to be applied to a tissue (e.g., nerve, muscle, etc.). In the examples in which the IMD 825 comprises an IPG, the tissue to be stimulated may comprise tissue to maintain or restore upper airway patency, such as but not limited to a hypoglossal nerve, an infrahyoid muscle (IHM)-innervating nerve (e.g. an ansa cervicalis-related nerve), and/or other nerves. In some such examples, the stimulation component 826 also may comprise circuitry for generating and delivering the stimulation signal. In some examples, the stimulation component 826 of the IMD 825 also may comprise a stimulation element, such as an electrode through which the stimulation signal may be applied to the target tissue.

In some examples, the sensing component 837 comprises a sensing engine to receive a sensing signal obtained relative to a tissue (e.g., muscle, organ, etc.). In some examples in which the IMD 825 comprises an IPG for treating SDB, the tissue to be sensed may be related to respiration, oxygenation, cardiac functions, upper airway patency, and the like. In some such examples, the sensing component 837 also may comprise circuitry for receiving and processing the sensing signal. In some examples, the sensing component 837 of the IMD 825 also may comprise a sensing element, such as an electrode or other element through which the sensing signal is obtained. In some examples, the sensing element may comprise an accelerometer for determining sleep information, respiratory information, posture information, and/or physical control information. The accelerometer may be implantable, and in some examples, may be incorporated within a device including a stimulation generating element (e.g., 826), such as an implantable pulse generator, which may comprise one example implementation of the IMD 825 in FIG. 7. In some examples, the accelerometer may be located external to the patient such as (but not limited to) being located in a patient support (e.g. mattress, pillow, chair, bed frame, etc.)

Of course, in contexts in which the IMD 825 relates to bodily organs, functions, etc. other than SDB, the stimulation component 826 and sensing component 837 may be deployed relative to other tissues. For instance, the IMD 825 may be deployed to treat pelvic disorders, such as stress incontinence or other conditions, with applicable tissues including the bladder, pudendal nerve, urinary and/or anal sphincters and the like.

In some examples, the stimulation component 826 and/or sensing component 837 may be on-board the IMD 825, which in some examples may comprise a microstimulator.

In some examples, at least a portion of the stimulation component 826 and/or sensing component 837 may be separate from, and independent of, a housing of the IMD 825 with one or both components 826, 837 being in wired or wireless communication with the IMD 825.

As further shown in FIG. 7, the patient communication devices 810 may communicate with other devices, entities, etc. via processing resource 830 via a wireless communication protocol as represented by directional arrows 827 and/or wired communication protocol in some examples. It will be understood that processing resource 830 may comprise a computing resource (including stored programming) provided via a third party to help provide and support patient management with the clinician-controlled devices 850 (e.g. clinician entities, care entities) and the patient app 812, such as the service provider 30 illustrated by FIG. 1. In some examples, the processing resource 830 may include a dedicated processor. In some examples, the processing resource 830 may include a plurality of distributed computing resource forming at least part of a cloud computing system, including programming, provided via a service provider (e.g., third party) to provide, support, and manage the patient management app for the care entities associated with the clinician-controlled devices 850 and the patient app 812 for the patients, which facilitates patient care and facilitates coordinated interaction among the care entities with each other and the respective patients. In some examples, the processing resource 830 may comprise at least a portion or, and/or an example implementation of, the control portion 900 (FIG. 8A) and user interface 940 (FIG. 9). In some examples, the processing resource 830 may be provided via a device manufacturer or servicer, or service provider contracted by a device manufacturer. The processing resource 830 and/or cloud computing system may be hosted via the internet, World Wide Web, and/or other network communication link.

As further shown in FIG. 7, example arrangement 800 may comprise an array 840 of clinician-controlled devices 850, which provide care in some manner to a patient associated with one of the devices 810. The clinician-controlled devices 850 may be associated with different entities, which provide care in some manner to a patient associated with one of the devices 810. The entities associated with each clinician-controlled device 850 may work together in at least some aspects to help coordinate care for the patient(s). Each entity may provide a particular form of expertise in patient care, such examples in which one entity (associated with a clinician-controlled device 850) may comprise a medical clinic, while another entity (associated with a different clinician-controlled device 850) may comprise a sleep center, and other entities may comprise providers which support patient care in some manner. There may greater or fewer than the two clinician-controlled devices (e.g., care entities) shown in FIG. 7 which form at least part of a care team.

In some examples, each clinician-controlled device 850 comprises a computing device, such as workstation or other computing device which may be stationary or mobile, including a user interface (e.g., 940 in FIG. 9) to support operation and display of GUIs associated with a clinician portal 855. Among other functions and features, the clinician portal 855 may comprise a patient management app 860 by which the particular care provider (e.g., medical clinic, sleep center, etc.) may manage patient care among a group of patients, for an individual patient, etc. The patient management app 860 also may enable communicating with other entities regarding patient care of the patients associated with devices 810. In some examples, the clinician-controlled devices 850 may communicate with each other via the processing resource 830 (e.g., network communication link, internet, web, etc.) as represented via the arrows 827.

At least some features and attributes of the patient management app 860 and/or patient app 812 may be implemented as described in association with PCT Publication WO2022/182756. The above-described GUI portions of FIGS. 4A-5G may be displayable on a display screen associated with a clinician-controlled devices 850 which may be mobile (e.g., phone, tablet, etc.) or stationary (e.g., desktop, workstation, etc.). In some examples, the GUI portions in FIG. 4A-5G may comprise example implementations of the patient management app 860 operable and displayable as a GUI of clinician portal 855, as described in association with FIG. 7.

It will be further understood that the arrangement of the various portions displayed on each respective example GUI portions and/or the detailed listings within each respective displayed GUI portion may form part of a method of patient management (including but not limited to stimulation therapy treatment) which a clinician (and/or other health care professional) may perform to advance patient care, such as any of the example methods of FIGS. 3A-3D and 6. Similarly, it will be apparent from FIG. 7 and the GUI portions in FIG. 4A-5G, and the engines, control portions, etc. in association with FIGS. 8A-12, that the various features, arrangements, components, etc. may be embodied as a system or apparatus.

In some examples, the example arrangement 800 may comprise a clinician programmer 865, which may periodically communicate with the IMD 825 wirelessly (e.g., inductive telemetry via a telemetry head 867) to initially configure and/or modify the configured stimulation therapy settings, sensing settings, etc. of the IMD 825 as represented via directional arrow 829.

In some examples, the programmer 865 comprises a user interface, such as but not limited to, a GUI to facilitate display and input relative to workflows by which a clinician operates the programmer 865. It will be further understood that the programmer 865 may perform tasks or operations (relating to patient care, maintenance) etc. other than programming stimulation-related aspects of the IMD 825. Moreover, in some examples, the programmer 865 may comprise or be in communication with a device dedicated solely for the purpose of communicating with, programming, etc., the IMD 825, such as the illustrated telemetry head 867 coupled to a controller 868. In some examples, the programmer 865 includes a portable computing device that is in communication with a telemetry head 867 that is dedicated solely for the purposes of communicating with the IMD 825. In some examples, the clinician programmer 865 also may communicate directly with the clinician portal 855 (such as via patient management app 860) to update the patient management system/method regarding at least stimulation settings, etc. which are configured in the IMD 825 per workflows of the clinician programmer 865.

In some examples, the telemetry head 867 and controller 868 may be implemented to include at least some of substantially the same features and attributes as described by PCT Publication WO2022/187471, published on Sep. 9, 2022, and entitled "Assemblies and Methods for Wirelessly Interfacing with an Implantable Medical Device", corresponding to U.S. National Stage application Ser. No. 18/280,156, filed Sep. 3, 2023, and granted as U.S. Pat. No. 12,589,250 on Mar. 31, 2026, which is hereby incorporated by reference in its entirety for its teaching.

In some examples, as noted above, the programmer 865 may comprise a non-dedicated device which may be used for purposes (e.g. general communication, general computing, etc.) other than communicating with or, programming the IMD 825. In some such examples, the programmer 865 may comprise a consumer device, such as a consumer tablet, smart phone, etc. which is also operable via secure modes/communications/paths to communicate with, program, etc., the IMD 825.

The GUI portion available on the clinician programmer 865 may comprise one example implementation of, and/or comprise at least some of the features and attributes as described at least in PCT Publication WO2022/182756.

Accordingly, it will be further understood that the programmer 865 and/or IMD 825 may comprise a control portion, or comprise an example implementation of one part of a control portion, such as control portion 900 as later described in association with at least FIG. 8A.

In some examples, the arrangement 800 may further include external monitoring circuitry 811 that senses or monitors patient data. The external monitoring circuitry 811 may comprise or form part of a device which is external to the patient. For example, the external monitoring circuitry 811 may be selectively worn by the patient such as around the wrist or on a finger, an arm, an ankle, a torso, a head, a neck, etc. of the patient. In some of these examples, external monitoring circuitry 811 may take the form of a wrist-watch, such as a smart watch. However, in some such examples, the external monitoring circuitry 811 may not be worn by the patient, but be positioned in a proximity to the patient sufficient for sensing to enable monitoring and/or diagnosis. In some of these examples, the external monitoring circuitry 811 may comprise a patient support such as, but not limited to, a mattress, bed, chair, and the like.

In some examples, the external monitoring circuitry 811 may comprise some components worn by the patient and some components which placed in close proximity to, but not worn, by the patient.

Whether worn on the patient and/or positioned near the patient, sensing components associated with external monitoring circuitry 811 become oriented in sensing relation to one or more portions of the patient's body so as to facilitate sensing various physiologic phenomenon such as (but not limited to) the sensing parameters.

In some examples, the external monitoring circuitry 811 may communicate directly with patient communication device 810, such that the patient data sensed and/or determine by the external monitoring circuitry 811 may be selectively integrated directly into, and/or be complementarily combined with, SDB care-related information on the patient communication device 810, such as on patient app 812. This SDB care-related information may comprise patient management information and/or stimulation therapy-related information, as further described below, or other information.

In some examples, communication (as represented by directional arrow 869) between the external monitoring circuitry 811 and the patient app 812 (hosted on patient communication device 810) may be performed via a wireless communication protocol (e.g., Bluetooth, infrared, near-field communication) and/or via a wired connection between the respective devices 810 and 811. In some instances, this communication pathway may sometimes be referred to as a direct communication pathway.

In some examples, the external monitoring circuitry 811 may comprise a general consumer product which is not specifically dedicated for use with patient communication device 810, patient remote 820, and/or IMD 825.

In some examples, the external monitoring circuitry 811 may be implemented according to at least some of substantially the same features and attributes as described by PCT Publication WO2022/182756 and/or the sensing functionalities described below in connection with FIGS. 11-12. For example, the external monitoring circuitry 811 may sense various parameters, such as cardiac parameters (e.g., heart rate, an electrocardiogram (ECG), and/or other cardiovascular phenomenon), respiration, breathing rhythm, chest motion, oximetry, peripheral arterial signal, blood pressure, body position, snoring, AHI, time in bed, sleep time (e.g., start and stop times, total time, types of sleep), posture, among other physiologic parameters or environmental parameters (e.g., air temperature, humidity, amount of light, external interruptions). In some examples, the external monitoring circuitry 811 may sense a plurality of parameters using different sensing modalities, such as but not limited to an accelerometer, pressure sensor, acoustic sensor, light sensor and/or communication with other devices, such as smart thermostat, smart lights, and other devices, among other sensing modalities. In some examples, the external monitoring circuitry 811 may determine a parameter using a combination of the other parameters, such as determining sleep from a combination of posture, time, snoring, heart rate and/or other parameters. For example, the external monitoring circuitry 811 may determine whether snoring sounds are attributable to the patient or someone else, such as another human or animal.

Although not illustrated by FIG. 7, the processing resource 830 may include a plurality of processing circuits which are distributed. For example, the different processing circuits may provide different operational support, such as providing GUI portions, diagnostics, monitoring, and communications, among other operations. In some examples, the processing resource 830 may be implemented as different resources, which may include the back-end diagnostic/monitoring functions and back end communication pathway.

FIG. 8A is a block diagram schematically representing an example control portion 900. In some examples, control portion 900 includes a controller 902 and a memory 904. In some examples, control portion 900 provides one example implementation of a control portion forming a part of, implementing, and/or generally managing the example arrangements, including clinician portals and/or patient management app, cloud resources, patient management systems, patient mobile apps, user interfaces, control portion, instructions, workflows, engines, functions, parameters, and/or methods, as described throughout examples of the present disclosure in association with FIGS. 1-7.

In general terms, the controller 902 of the control portion 900 comprises an electronics assembly 906 (e.g., at least one processor circuit, microprocessor, integrated circuits and logic, etc.) and associated memories or storage devices. The controller 902 is electrically couplable to, and in communication with, memory 904 to generate control signals to direct operation of at least some of the example arrangements, including clinician portals, cloud resources, patient management apps and/or systems, patient mobile apps, user interfaces, control portion, instructions, workflows, engines, functions, parameters, and/or methods, as described throughout examples of the present disclosure. In some examples, these generated control signals include, but are not limited to, employing instructions 907 and/or data 909 stored in memory 904 to at least direct and manage SDB care (e.g. sensing, stimulation, etc.) in the manner described in at least some examples of the present disclosure, such as but not limited to patient care and management including clinician portals, workflows and a patient virtual check-in. In some instances, the controller 902 or control portion 900 May 3893 sometimes be referred to as being programmed to perform the above-identified actions, functions, etc.

In response to or based upon commands received via a GUI (e.g., user interface 940 in FIG. 9 or example GUIs throughout FIGS. 2A-3G) and/or via machine readable instructions, controller 902 generates control signals as described above in accordance with at least some of the examples of the present disclosure. In some examples, controller 902 is embodied in a general purpose computing device while in some examples, controller 902 is incorporated into or associated with at least some of the example arrangements, including clinician portals, cloud resource, patient management apps and/or systems, patient mobile apps, user interface, control portion, instructions, workflows, engines, functions, parameters, and/or methods, etc. as described throughout examples of the present disclosure.

For purposes of this application, in reference to the controller 902, the term "processor" or "processing resource" shall mean a presently developed or future developed processor (or processing resources) that executes machine readable instructions contained in a memory or that includes circuitry to perform computations. In some examples, execution of the machine readable instructions, such as those provided via memory 904 of control portion 900 cause the processing resource to perform the above-identified actions, such as operating controller 902 to implement SDB care via the various example implementations as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 904. The machine readable instructions may include a sequence of instructions, a processor-executable machine learning model, or the like. In some examples, memory 904 comprises a computer readable tangible medium providing non-volatile storage of the machine readable instructions executable by a process of controller 902. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 902 may be embodied as part of at least one application-specific integrated circuit (ASIC), at least one field-programmable gate array (FPGA), and/or the like. In at least some examples, the controller 902 is not limited to any specific combination of hardware circuitry and machine readable instructions, nor limited to any particular source for the machine readable instructions executed by the controller 902.

In some examples, control portion 900 may be entirely implemented within or by a stand-alone device.

In some examples, the control portion 900 may be partially implemented in one of the example arrangements, clinician portals, cloud resources, patient management systems, patient mobile apps, etc. and partially implemented in a computing resource separate from, and independent of, the example arrangements, including clinician portals, cloud resources, patient management apps and/or systems, patient mobile apps, etc. but in communication with such example arrangements, etc. For instance, in some examples control portion 900 may be implemented via a server accessible via the cloud and/or other network pathways. In some examples, the control portion 90 may be distributed or apportioned among multiple devices or resources such as among a server, an example arrangement, and/or a user interface.

FIG. 8B is a diagram schematically illustrating at least some example arrangements of a control portion 900 by which the control portion 90 (FIG. 8A) may be implemented. In some examples, control portion 920 is entirely implemented within or by an IPG assembly 925, which has at least some of substantially the same features and attributes as a pulse generator (e.g., power/control element) as previously described throughout the present disclosure. In some examples, control portion 920 is entirely implemented within or by a remote control 930 (e.g., a programmer) external to the patient's body, such as a patient control 932 and/or a clinician control 934. In some examples, the control portion 900 is partially implemented in the IPG assembly 925 and partially implemented in the remote control 930 (patient control 932 and/or clinician control 934). In some examples, control portion 920 is entirely implemented within or by processing resource 936, such as a processor circuit associated with or in communication with a clinician-controlled device for implementing a clinician portal.

FIG. 9 is a block diagram schematically representing an example user interface. In some examples, control portion 900 includes, and/or is in communication with, a user interface 940 as shown in FIG. 9. In some examples, at least some portions or aspects of the user interface 940 are provided via a GUI, and may comprise a display 944 and input 942. In some examples, user interface 940 comprises a user interface or other display that provides for the simultaneous display, activation, and/or operation of at least some of the example arrangements, clinician portals, cloud resources, patient management systems, patient mobile apps, user interface, control portion, workflows, instructions, engines, functions, parameters, and/or methods, etc., as described in association with FIGS. 1-8B. For instance, the various user interfaces described in association with FIGS. 4A-5G may each provide an example implementation of user interface 940.

Some examples may be implemented using a patient management engine, which may include at least some of substantially the same features and attributes as described in PCT Publication WO2022/182756.

FIG. 10 is a block diagram schematically representing an example patient management engine. As shown in FIG. 10, in some examples a patient management engine 1300 may control, direct, etc., obtaining patient data and displaying such data to help manage patient care, etc., and may implement the flow diagrams of any of FIGS. 3A-3D and 6 and/or implement or display any of the GUI portions illustrated by FIGS. 4A-5G. At least some aspects of patient management includes actions, tools, etc. to deliver stimulation therapy to a tissue of a patient, such as but not limited to tissue which may maintain or restore upper airway patency to treat SDB. In some examples, the example methods and/or systems of the present disclosure directed to patient management may lead to adjustments in stimulation programming (and related settings), which are used to configure the IMD (e.g., IMD 825 of FIG. 7) such that the stimulation programming settings become stored within, and are implemented via the IMD to deliver stimulation therapy and related care to the patient.

With further reference to FIG. 10, in some examples the patient management engine 1300 comprises a usage tracking sub-engine 1310, a display tools sub-engine 1350, and a communication sub-engine 1380. In some examples, all or some of the features of the patient management engine 1300 may be implemented via, and/or as part of, control portion 900 as described in association with FIG. 8A. Moreover, it will be understood that features and aspects of the patient management engine 1300 are not strictly limited to the sub-engines 1310, 1350, and/or 1380. At least some aspects of the patient management engine 1300 are described in association with the GUI portions previously described in connection with FIGS. 4A-5G.

In various examples, the usage tracking sub-engine 1310 may track different patient data associated with usage of an IMD. For example, the patient management engine 1300, via a usage tracking sub-engine 1310, may track total number of nights stimulation therapy was used parameter 1314, the number of nights (within the selected period, e.g. 30 days) for which patient usage of the stimulation therapy met or exceeded a threshold to determine the nights over a threshold parameter 1316, as previously described.

As further shown in FIG. 10, the usage tracking sub-engine 1310 comprises a night function 1320 by which usage may be tracked, evaluated, etc. according to the details of each night within the selected period (of function 1312). Moreover, in some examples, the night function parameter 1314 may operate according to a duration parameter 1322 and/or a pause parameter 1324. In particular, per the duration parameter 1322, usage tracking sub-engine 1310 may cause tracking of a duration of usage per night, which may be expressed as an average, mean, and the like. One example implementation of the duration parameter 1322 is displayed as parameter 424 (of summary region 418) in the example GUI portion 400 in FIG. 5A.

Moreover, per the above-noted pause parameter 1324, usage tracking sub-engine 1310 may cause tracking of the number of times per night which stimulation therapy was paused by the patient, with the number of times being expressed as an average, mean, and the like. One example implementation of the pause parameter 1324 is displayed as parameter 426 (of summary region 418) in the example GUI portion 400 in FIG. 5A, which shows a non-limiting example in which, for the days which therapy was used.

In some examples, the usage tracking sub-engine 1310 also may provide a stimulation settings parameter 1330 that tracks and/or displays the stimulation settings for the IMD which is used to provide the stimulation therapy delivered to the patient. Example stimulation settings parameter 1330 include a pulse width, a pulse rate, and/or electrodes used to apply the stimulation therapy.

With further reference to FIG. 10, the patient management engine 1300 comprises a display tools sub-engine 1350 by which the engine 1300 is to cause display of patient management information as a GUI on a display screen of a clinician-controlled device. As shown in FIG. 10, in some examples the display tools sub-engine 1350 may include a filter display function 1351 to provide the display of various attentions or alerts indicative of non-compliant patients, such as the attention icon(s) 224-2, 224-3 and resulting filters for the filter icons 208, 210, 212 illustrated by the GUI portion 200 of FIG. 4C and the attention icon(s) 404, 430, 482 illustrated by GUI portion 400 of FIG. 5A, among others.

The display tools sub-engine 1350 may further comprise a summary display function 1352 to provide a summary of various (selectable) usage parameters for display. One example implementation of summary display function 1352 (FIG. 10) comprises the parameters of summary region 418 in FIG. 5A. In some examples, the summary also may display a date range icon 432, which specifies and displays a date range for which the values of the parameters were obtained.

As further shown in FIG. 10, the nightly usage per period parameter function 1354 (of display tools sub-engine 1350) may cause display of nightly usage information for a selectable period (e.g., 30 days, 60 days, etc.), with one example implementation being provided in the GUI portion 400 in FIG. 5A as nightly utilization region 428.

The display tools sub-engine 1350 (of patient management engine 1300) may comprise an amplitude changes display function 1356 by which patient changes in stimulation therapy amplitude may be displayed. One example implementation of the amplitude changes display function 1356 is provided as amplitude changes region 450 of GUI portion 400, as shown in FIG. 5A.

The display tools sub-engine 1350 (of patient management engine 1300) may comprise a patient survey display function 1357 by which summary of patient surveys from virtual check-ins may be displayed. One example implementation of the patient survey display function 1357 is provided as patient survey region 480 of GUI portion 400, as shown in FIG. 5A.

With further reference to the patient management engine 1300 in FIG. 10, in some examples the display tools sub-engine 1350 may comprise an outcomes display function 1358, which provides a summary, details, etc. regarding various performance metrics regarding patient outcomes, therapy effectiveness (e.g., efficacy), etc. regarding the patient's stimulation therapy.

In some examples, the display tools sub-engine 1350 may comprise an equipment display function 1360. In an example implementation, the equipment display function 1360 may provide a system region and a generator region. The system region may display data regarding a type of equipment (e.g. stimulation lead, sensor lead, pulse generator), with such information including model numbers, serial numbers, location in body, and the like. The generator region may provide more detailed information regarding the pulse generator such as, but not limited to, battery status (e.g. good, bad, high, low, etc.), and the like.

In some examples, the display tools sub-engine 1350 may comprise a programming function 1370, which may comprise a stimulation parameter function 1372, a sensing parameter function 1374, and a thresholds parameter function 1376 that track and/or display different parameters. In one example implementation, the programming function 1370 (FIG. 10) may be used to provide parameters in different GUI portions.

The display tools sub-engine 1350 may comprise an other display function 1377 by which other parameters relating to stimulation therapy, patient management, etc. may be automatically or selectively displayed on a user interface. For instance, in some examples, via the other display function 1377 of display tools sub-engine 1350, upon activation of any one or more of the icons (e.g., filter icon), subsets of the listing of patients which are associated with the icon may be displayed on a GUI portion.

As further shown in FIG. 10, the communication sub-engine 1380 (of patient management engine 1300) may control, affect, facilitate, etc., at least in part, communications among various elements of the example arrangement 800 in FIG. 7, such as clinician portals 855 (of clinician-controlled devices 850), patient apps 812 (of devices 810), patient remote 820, etc.

In some examples, the communication sub-engine 1380 may comprise a link function 1382 to specify and/or drive communications per a selectable link specified via a type function 1384 and/or a status function 1386. The type function 1384 may comprise various types of communication links, which may be wired or wireless (e.g. internet, Bluetooth, peer-to-peer, LAN, WAN, and the like).

In some examples, the communication sub-engine 1380 in FIG. 10 also may comprise a tools function 1390 providing various communication tools including, but not limited to, a share function 1392 by which various patient management information, actions, etc. may be shared, such as among members of a care team (e.g. the different clinicians associated with the different devices 850 in FIG. 7). Similarly, via function 1392, such information also may be shared with a patient, insurer, other.

Accordingly, the above-described various features of the GUI portions, e.g., FIGS. 4A-5G, as driven via the various functions and parameters of the display tools sub-engine 1350 in FIG. 10, provide a rich environment by which a clinician may manage patient care. For instance, in some examples, upon a clinician viewing the various displayed patient data a main therapy GUI, such as GUI portion 200 of FIG. 4C, patients which are non-compliant may be automatically visually displayed, with different class (e.g., type or categorization) of non-compliance identified. Accordingly, patients which are non-compliant and/or classes or type of non-compliance, is easily viewable to the clinician and the clinician may filter for different types of non-compliance to more easily assess the same and resolve issues to improve patient compliance. Based on the assessment, the clinician may order further patient education, communicate request for data and/or patient survey, make changes to stimulation therapy programming, and the like, as desired.

FIG. 11 is a block diagram schematically representing example sensing parameters associated with at least a third party diagnostic/monitoring portion. In some examples, the example arrangement used to sense the parameters 2400 may comprise at least some of substantially the same features and attributes as the example arrangement of FIGS. 1-10.

In some examples, the sensing parameters may be sensed by, and/or received at, the third party diagnostic/monitoring circuitry, such as an external monitoring circuitry 811 (e.g., sensor or device) of FIG. 7.

In general terms, these sensing parameters are in addition to any parameters sensed by the IMD 825, patient remote 820, and/or patient app 812 (hostable on device 810), which are generally considered part of, or related to, a therapy system owned or provided by an entity other than the third party which sells, manages, supports, etc. the third party diagnostic/monitoring portion. However, in some examples, via contractual relationship or other mechanism, the third party diagnostic/monitoring portion may be controlled by the same entity which controls, manufactures, etc. the IMD 825, patient remote 820, and/or patient app 812 (hostable on device 810).

In some examples, the sensing parameters may comprise cardiac parameters 2410 such as, but not limited to, a heart rate (HR) 2412, an electrocardiogram (ECG) 2414, and/or other cardiovascular phenomenon.

In some examples, the sensing parameters 2400 may comprise parameters of respiration 2420, chest motion 2422, and/or oximetry 2424. In some examples, the sensed chest motion 2422 may comprise just one of several modalities to sense respiration 2420. The oximetry parameter 2424 may be sensed via pulse oximetry, such as a finger-mountable pulse oximetry unit or other modality.

In some examples, the sensing parameters 2400 may comprise parameters of a peripheral arterial signal 2426, blood pressure 2428, and/or actigraphy 2430.

In some examples, the sensing parameters 2400 may comprise parameters of body position 2432, snoring 2434 (or other acoustic parameters), and/or other 2438 parameters of physiologic phenomenon or environmental phenomenon, which may relate to patient care for treating SDB.

As further shown in FIG. 11, in some examples, the sensing parameters 2400 may comprise an interruption parameter 2439, which may sense or be used to determine interruptions to sleep, which in some examples may be external interruptions. The interruptions may be sensed or determined via one or more of the above-identified sensing modalities, parameters, etc. of sensing parameters 2400 of FIG. 11 and/or may be sensed or determined via addition or alternative sensing modalities, parameters, etc. In some examples, such interruptions may be sensed using an acoustic sensor, a pressure sensor, and/or other sensors, and may be indicative of sounds that may wake the patient (e.g., alarm systems, fire alarm, city noises, train noise, other ambient noise), snoring of another person or animal, movement on the bed (e.g., animal or another human moving on the bed), and other potential interruptions to the patient's sleep. In some examples, snoring sounds may be distinguished between those generated by the patient and those generated by another human or animal. Among various alternative or additional sensing modalities, in some examples at least some of the interruptions may be sensed via an accelerometer (or other movement sensor), which may be external to the patient (e.g., on/in bed, pillow, sleep mat, etc.), worn by the patient, or even implanted in the patient.

FIG. 12 is a block diagram schematically representing example determined parameters 2500 associated with at least a third party diagnostic/monitoring portion.

In general terms, the determined parameters 2500 may be determined from, or in association with, at least some of the sensed parameters 2400 of FIG. 11 and/or other sensing (e.g., parameters, modalities, etc.) described throughout the examples of present disclosure.

In some examples, the determined parameters 2500 may comprise SDB events 2510, which may comprise apnea events, hypopnea events, and or other detectable events. The apnea events may comprise events of obstructive sleep apnea, central sleep apnea, and/or mixed sleep apnea.

In some examples, the determined parameters 2500 may comprise various indices for quantifying an intensity or severity of such SDB events such as, but not limited to, an AHI 2512, respiratory disturbance index (RDI) 2514, and/or an oxygen desaturation index (ODI) 2516.

In some examples, the determined parameters 2500 may comprise various parameter for quantifying aspects of sleep 2530 (e.g., sleep quality) such as, but not limited to, sleep state 2532, sleep stage 2534, time 2536, score 2540, and time-in-bed 2538. In some such examples, the sleep state parameter 2532 may comprise a sleep-wake status, sleep start time, sleep stop time, sleep pause times, and the like. The time parameter 2536 may relate to total sleep time, total stimulation therapy time, and/or other time parameters related to sleep. In some examples, the score parameter 2540 may relate to a sleep score which provides information about sleep quality. In some examples, the sleep score may be impacted by external interruptions, such as noises and/or movement that occur during the total sleep time. In some examples, the time-in-bed parameter 2538 may provide a total time-in-bed within an intended sleep period (e.g. 10 μm to 6 am), within a twenty-four hour period, etc. Among other aspects, the time-in-bed parameter 2538 may help provide context for the start times, stop times, number and duration of pause times, and/or total therapy-on duration, which in turn may be used to evaluate therapy efficacy, patient adherence, and related care parameters.

In some examples, the determined parameters 2500 may comprise a home sleep test (HST) parameter 2550, which may comprise information obtained from a sleep study performed in a home study using at least some of the sensed parameters 2400 in FIG. 11 obtainable via third party diagnostic/monitoring portion (e.g., device). In some such examples, the home sleep study may approximate a formal polysomnongraphy (PSG) study.

In some examples, the determined parameters 2500 may comprise cardiac parameters 2560 such as, but not limited to, atrial fibrillation 2562 and/or other parameters 2564, which may relate to other arrhythmias or other indicators of negative and/or positive cardiac health, which may be used to evaluate, adjust, etc. aspects of SDB care.

FIGS. 13A-13D are graphs illustrating example patterns for patients titrating stimulation amplitude, such as during an initial period of therapy use of an IMD (e.g., for sleep disordered breathing). The graphs illustrated by FIGS. 13A-13D may be used to identify, classify, and/or filter attention-warranting-titration patients, as described by any of FIGS. 1-12. The graphs of FIGS. 13A-13D each illustrate stimulation amplitude changes made by (or for) a patient, as represented via line 3003, and a reference by which attention-warranting-titration patients may be identified. On the graphs in FIGS. 13A-13D, the Y-axis represents the stimulation amplitude change (e.g., from the baseline illustrated as 0.0 Volts and which may extend up to 1.2 Volts in some examples) and the X-axis represents the number of usage days since first use. In some examples, each stepwise change in stimulation may include 0.1 Volts.

In some examples, a titration reference (which may sometimes interchangeably be referred to herein as "a stimulation amplitude change reference") may be represented by line 3001 and may comprise (or alternatively may be defined relative to) an average (e.g., median, mean) of stimulation amplitude changes made by a plurality of compliant patients over the period of initial use. In some examples, the titration reference may comprise (or alternatively may be defined relative to) a standard deviation from the median/mean (line 3001), which is represented via shaded region 3005. As shown by each of FIGS. 13A-13D, each attention-warranting-titration patient exhibits some stimulation amplitude changes, illustrated via line 3003, which deviate from titration reference when implemented as line 3001. For instance, in the example of FIG. 13A, the stimulation amplitude (line 3003), which may be patient's selected, rapidly and significantly deviates from the reference (e.g., line 3001) within the first 5-10 days of use, and still differs from the reference (line 3001) up through day 20. Among other potential factors, this deviation may be quantified as a percentage difference (or other metric) from the reference (line 3001) and upon the deviation meeting a criteria (e.g., exceeding a threshold deviation), the patient may be flagged as a patient which is non-compliant or likely to become non-compliant due to overly-aggressively titrating, e.g. overly-aggressively increasing their stimulation amplitude within a given time frame (e.g., 5, 10, or 20 days).

Figure 13A:
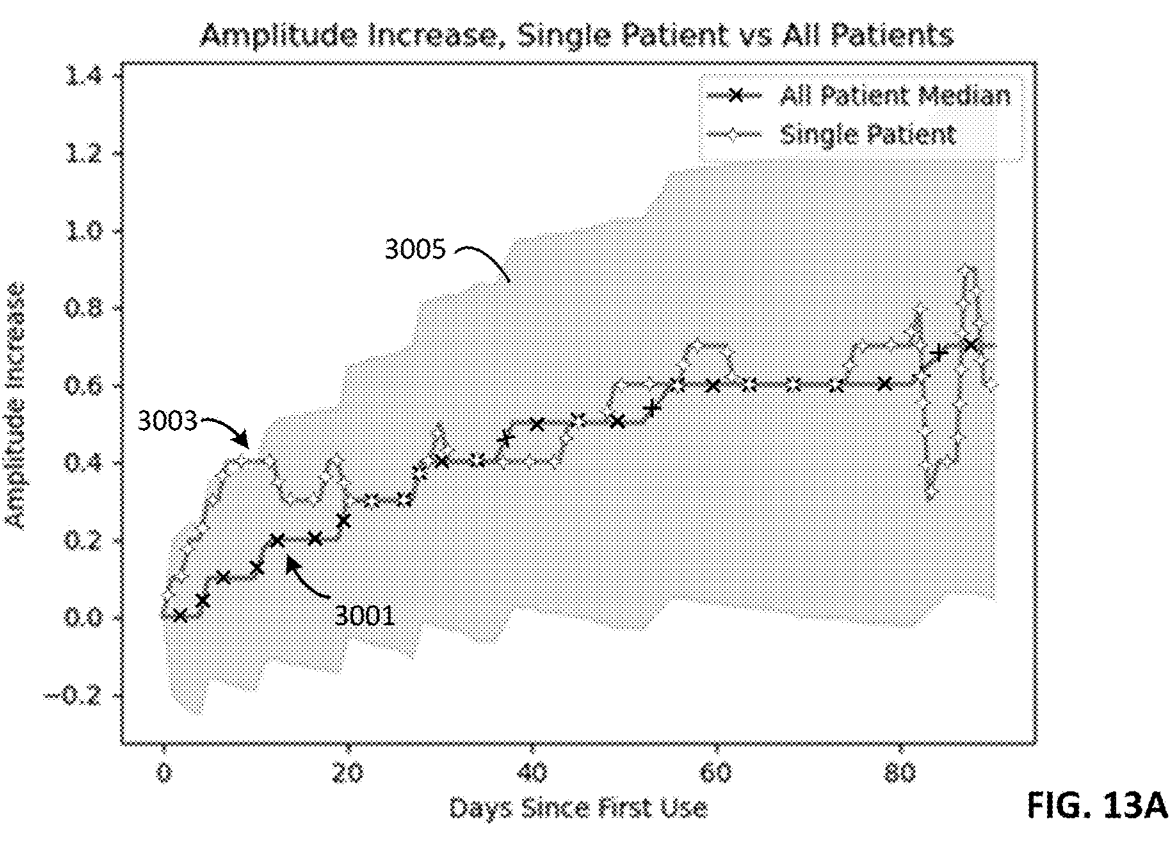
FIGS. 13A-13D are graphs illustrating example patterns of patients titrating stimulation amplitude, such as during an initial use period.
Figure 13B:
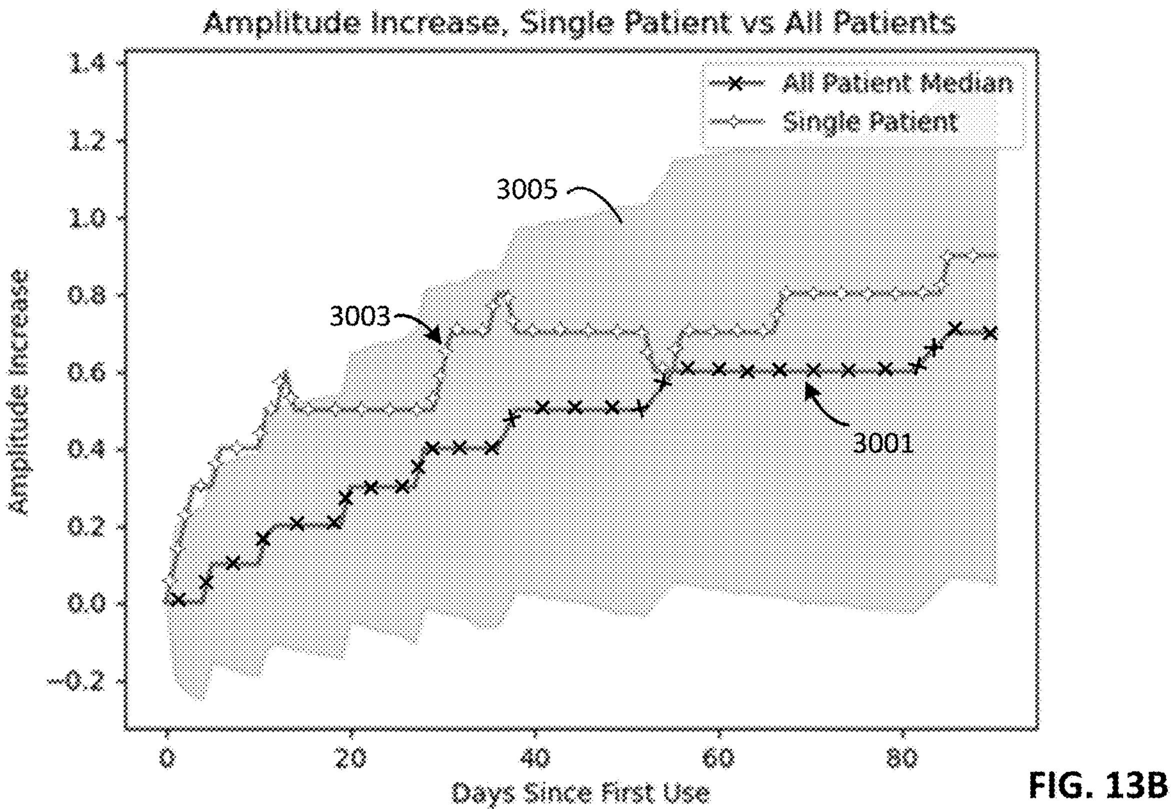

Similarly, in the example of FIG. 13B, the stimulation amplitude (line 3003), which may be patient's selected, rapidly and significantly deviates from (e.g., is much higher than) the reference (e.g. line 3001) within the first 5-10 days of use, and still differs from the reference (line 3001) up through about day 50, and again from about day 50 through the end of the initial use period (e.g., 90 days). As in the example FIG. 13A, among other potential factors, this deviation shown in FIG. 13B may be quantified as a percentage difference (or other metric) from the reference (line 3001) and upon the deviation meeting a criteria (e.g., exceeding a threshold deviation), the patient may be flagged as a patient which is non-compliant or likely to become non-compliant due to overly-aggressively titrating, e.g. overly-aggressively increasing their stimulation amplitude within a given time frame (e.g., 5, 10, 20, 50, 90 days).

Figure 13C:
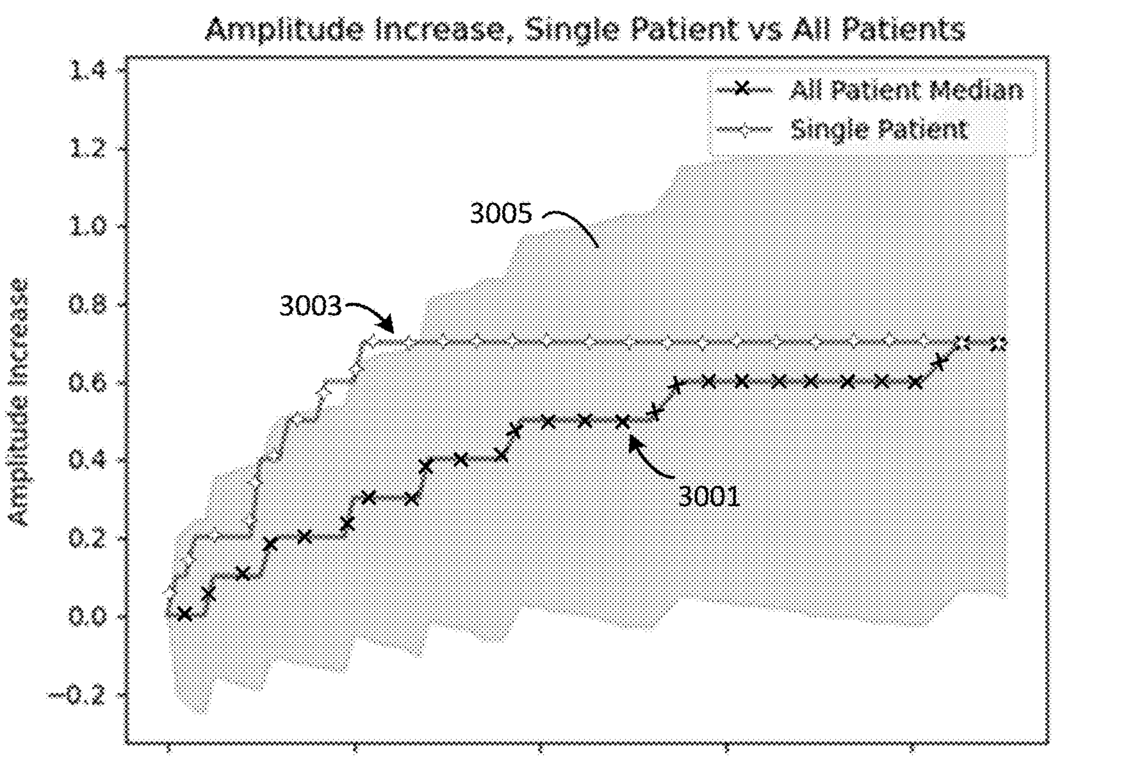

Moreover, even though the patient represented in FIG. 13C exhibits a stimulation amplitude change which is static from about 20 days to 90 days, the rapid increase over the first 20 days (and attendant significant deviation from line 3001), in some examples, may still provide a basis to identify (e.g., flag) this patient as being non-compliant and/or likely to become non-compliant during or after the initial use period.

Figure 13D:
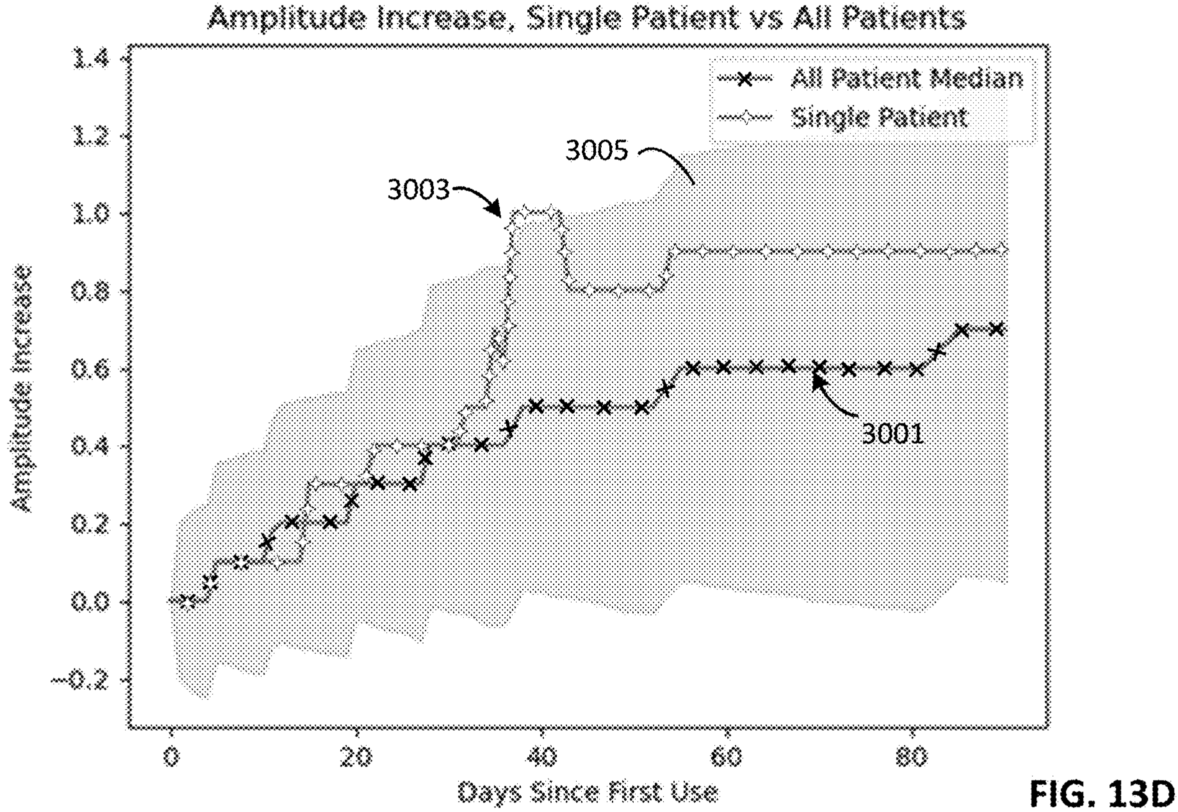

Finally, the patient represented in FIG. 13D exhibits stimulation amplitude changes which generally correspond to the reference (implemented as or relative to line 3001 in one example) such that the patient may be considered compliant and/or likely to remain compliant over a longer term. However, during the period of about 30 days to 35 days, the patient exhibits rapid increases in stimulation amplitude changes, which may provide a basis to identify (e.g., flag) this patient as being non-compliant and/or likely to become non-compliant during or after the initial use period, even with the later largely static period from day 40 through 90 days.

Accordingly, in some examples, one or more of the patients represented in FIGS. 13A-13D may identified as an attention-warranting titration patient to be populated in a GUI portion (e.g. FIGS. 4A, 4B) to quickly bring this patient to the attention of the clinician so that some counsel or intervention can be made during the period of deviation from a titration reference (e.g., line 3001). This early notification, via a GUI portion (e.g., FIGS. 4A, 4B), to the clinician may result in intervention (e.g., limiting patient changes to stimulation amplitude, related counseling, etc.) with the aim of increasing the likelihood of compliance in both the short term and long term, which in turn may improve patient outcomes (e.g., disease burden decrease) and/or patient usage (e.g., maintain minimum usage for a number of hours-per-day, number of days-per-week, number of weeks, etc.) in both the short term and long term.

While the examples of FIGS. 13A-13D are primarily directed to patient titration during an initial use period (e.g., 90 days in some examples) of a therapeutic stimulation device, it will be understood that the features and attributes of these examples (in context with all the example of the present disclosure) may be implemented for periods of use beyond the initial use period.

Various examples are implemented in accordance with the underlying Provisional Application Ser. No. 63/341,854, entitled "Clinician User Interface," filed May 13, 2022, to which benefit is claimed and which is fully incorporated herein by reference for its general and specific teachings. For instance, examples herein and/or in the Provisional Application can be combined in varying degrees (including wholly). Examples discussed in the Provisional Application are not intended, in any way, to be limiting to the overall technical disclosure, or to any part of the claimed disclosure unless specifically noted.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The following examples may comprise at least some of substantially the same features and attributes as, and/or example implementations of, the previously described examples of the present disclosure. The following examples may be implemented alone or together, which may comprise any various complementary combinations.

Example A1. A device comprising: a processing resource; and a display screen configured with the processing resource to present a graphical user interface (GUI) associated with a clinician portal including a plurality of GUI portions that are individually and selectively displayable to present patient data for a plurality of patients based on at least one filter for different classes of the plurality of patients.

Example A2. The device of example A1, wherein the patient data comprises objective patient data at least indicative of stimulation therapy activity and subjective patient data indicative of patient feedback and the display screen and processing resource are configured to present the GUI displaying at least one of the plurality of GUI portions populated using at least portions of the objective patient data juxtaposed with at least portions of the subjective patient data for the plurality of patients.

Example A3. The device of example A1, wherein: the processing resource is configured to receive the patient data for a plurality of patients, the patient data comprising objective patient data indicative of patient feedback; and the display screen and processing resource are configured to present the GUI by displaying selective ones of the plurality of GUI portions on the display screen.

Example A4. The device of example A1, wherein: the processing resource is configured to implement the clinician portal and to selectively integrate the patient data comprising objective patient data indicative of stimulation therapy activity and subjective patient data indicative of patient feedback; and the display screen is configured with the processing resource to present the plurality of GUI portions which are populated using at least a portion of the selectively integrated patient data.

Example A5. The device of example A1, wherein the display screen and processing resource are configured to: based on the patient data and the different classes of the plurality of patients, present a visual identification of respective ones of the plurality of patients on at least one of the plurality of GUI portions as being at least one of non-compliant patients or predicted non-compliant patients based on the at least one filter.

Example A6. The device of example A1, wherein the display screen and processing resource are configured to display the plurality of GUI portions with expanded features visually displayed on the display screen to manage the plurality of patients by exception based on a non-compliant criteria associated with the at least one filter.

Example A7. The device of example A1, wherein the plurality of GUI portions include a main GUI display which automatically presents a plurality of different non-compliance classes for each of the plurality of patients and a degree of each of the different non-compliance classes based on the at least one filter and as juxtaposed together, wherein areas of the main GUI display are selectable to transition to other respective ones of the GUI portions that expand on respective features.

Example A8. The device of example A7, wherein the different non-compliance classes include: under-utilizing patients which utilize an implantable medical device at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and/or attention-warranting-titration patients exhibiting stimulation amplitude change behavior deviating from a stimulation amplitude change reference.

Example A9. The device of example A1, wherein the patient data comprises objective and subjective patient data, and the objective patient data comprises at least one of: stimulation therapy activity reported from an implantable medical device associated with each respective one of the plurality of patients; or physiologic information reported from an implantable medical device associated with each respective one of the plurality of patients.

Example A10. The device of example A1, wherein the patient data is associated each respective patient of the plurality of patients as received from a plurality of sources selected from: an implantable medical device; a patient communication device; and clinician input to the clinician portal.

Example A11. The device of example A10, wherein the patient communication device comprises at least one of: a dedicated patient remote control; or a consumer electronic device.

Example A12. The device of example A11, wherein the patient data comprises objective and subjective patient data, and the patient remote control is in communication with, and is to at least receive the objective patient data from, the implantable medical device and the consumer electronic device is in communication with, and is to at least receive the objective patient data, from the patient remote control.

Example A13. The device of example A1, wherein the processing resource is configured to: based on the patient data for a patient of the plurality of patients, performing patient care by determining, within the clinician portal, a stimulation therapy to be delivered to upper airway patency-related tissue to treat sleep disordered breathing.

Example A14. The device of example A13, wherein the processing resource is configured to communicate the determined stimulation therapy to an implantable medical device of the patient via at least one of: a dedicated patient remote control; or a consumer electronic device.

Example A15. The device of example A1, wherein the processing resource is configured to based on the patient data, perform patient care by determining at least one patient management action and communicating the at least one patient management action to a patient communication device.

Example A16. The device of example A15, wherein the at least one patient management action comprises at least one of: scheduling a patient office visit; implementing at least one of a communication or a command to adjust parameters of stimulation therapy; implementing at least one of a communication or a command to adjust parameters of sensing; or implementing at least one of a communication or a command to adjust parameters of external patient monitoring.

Example A17. The device of example A1, wherein the different classes of the plurality of patients comprise patients with implantable medical devices that are categorized as: non-compliant patients; and compliant patients.

Example A18. The device of example A1, wherein the different classes of the plurality of patients comprise a plurality of classes of non-compliant patients with implantable medical devices, wherein the plurality of classes of non-compliant patients comprise: under-utilizing patients which utilize the implantable medical devices at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and/or attention-warranting-titration patients exhibiting stimulation amplitude change behavior deviating from a stimulation amplitude change reference.

Example A19. The device of example A1, wherein the patient data comprises objective and subjective patient data, and the processing resource is configured to: receive the objective patient data from patient communication devices, the objective patient data comprising at least one of sensed physiologic information or externally monitored information including at least one of: implantable medical device usage; cardiac information; respiratory information; chest motion; oxygen desaturation information; peripheral arterial information; blood pressure; body position; acoustic information including snoring; sleep information including at least one of time spent in bed, total sleep time, start time, stop time, and sleep stage(s); or sleep disordered breathing (SDB)-related index information.

Example A20. The device of example A1, wherein the patient data comprises objective and subjective patient data, wherein the processing resource is configured to receive the subjective patient data from patient communication devices, the subjective patient data comprising patient survey information including at least one of: implantable medical device usage; comfort levels; usage hindrances; device visible indicators; snoring levels; or energy levels.

Example A21. The device of example A1, wherein the patient data further comprises patient management information input to the clinician portal via clinician input to at least one of the plurality of GUI portions.

Example A22. The device of example A1, wherein the display screen and processing resource are configure to: represent respective ones of the plurality of GUI portions on other ones of the plurality of GUI portions via a corresponding icon, each of which is user selectable to cause transitions between respective ones of the GUI portions.

Example A23. The device of example A1, wherein the display screen and processing resource are configured to automatically present information which visually identifies non-compliant patients of the plurality of patients based on the at least one filter and an input field for clinician input via at least a portion of the plurality of GUI portions.

Example A24. The device of example A23, wherein the processing resource is configured to automatically output data to at least one patient communication device in response to clinician input to the input field to drive patient compliance.

Example A25. The device of example A1, wherein at least a subset of the plurality of GUI portions automatically present visual identification of non-compliant patients of the plurality of patients based on the at least one filter to cause at least one of improve patient compliance, prevent patient non-compliance, or mitigate further patient non-compliance.

Example A26. The device of example A1, wherein at least a subset of the plurality of GUI portions are patient specific and are selectable from at least another subset of the plurality of GUI portions which visually identify the plurality of patients.

Example A27. The device of example A26, wherein the processing resource is configured to: identify a patient of the plurality of patients based on at least one of the at least one filter and in at least one of the plurality of GUI portions; and receive a clinician input to the at least one of the plurality of GUI portions associated with the patient; and in response, output a communication to a patient communication device of the patient.

Example A28. The device of example A27, wherein the communication is provided at least one: prior to the patient being classified as non-compliant; and in response to the patient being classified as non-compliant based on the at least one filter.

Example B1. A non-transitory computer-readable storage medium comprising instructions that when executed cause a processing resource to: present a graphical user interface (GUI) associated with a clinician portal, the GUI including a plurality of GUI portions that are individually and selectively displayable to present patient data for a plurality of patients based on at least one filter for different classes of the plurality of patients.

Example B2. The computer-readable storage medium of example B1, wherein the GUI is presented on a display screen.

Example B3. The computer-readable storage medium of example B2, further comprising the display screen.

Example B4. The computer-readable storage medium of example B1, further comprising instructions that when executed, cause the processing resource to communicate a signal to a stimulation element to deliver stimulation to a patient among the plurality of patients.

Example B5. The computer-readable storage medium of example B4, further comprising the stimulation element to deliver a stimulation signal to the patient in response to the signal from the processing resource.

Example B6. The computer-readable storage medium of example B1, wherein the patient data comprises objective patient data at least indicative of stimulation therapy activity and subjective patient data indicative of patient feedback, and further comprising instructions that when executed, cause the processing resource to present the GUI displaying at least one of the plurality of GUI portions populated using at least portions of the objective patient data juxtaposed with at least portions of the subjective patient data for the plurality of patients.

Example B7. The computer-readable storage medium of example B1, further comprising instructions that when executed, cause the processing resource to: receive the patient data for a plurality of patients, the patient data comprising objective patient data indicative of patient feedback, and present the GUI by displaying selective ones of the plurality of GUI portions on the display screen.

Example B8. The computer-readable storage medium of example B1, further comprising instructions that when executed, cause the processing resource to: implement the clinician portal and to selectively integrate the patient data comprising objective patient data indicative of stimulation therapy activity and subjective patient data indicative of patient feedback; and present the plurality of GUI portions which are populated using at least a portion of the selectively integrated patient data.

Example B9. The computer-readable storage medium of example B1, further comprising instructions that when executed, cause the processing resource: based on the patient data and the different classes of the plurality of patients, present a visual identification of respective ones of the plurality of patients on at least one of the plurality of GUI portions as being at least one of non-compliant patients or predicted non-compliant patients based on the at least one filter.

Example B10. The computer-readable storage medium of example B1, further comprising instructions that when executed, cause the processing resource to display the plurality of GUI portions with expanded features visually displayed on the display screen to manage the plurality of patients by exception based on a non-compliant criteria associated with the at least one filter.

Example B11. The computer-readable storage medium of example B1, wherein the plurality of GUI portions include a main GUI display which automatically presents a plurality of different non-compliance classes for each of the plurality of patients and a degree of each of the different non-compliance classes based on the at least one filter and as juxtaposed together, wherein areas of the main GUI display are selectable to transition to other respective ones of the GUI portions that expand on respective features.

Example B12. The computer-readable storage medium of example B11, wherein the different non-compliance classes include: under-utilizing patients which utilize an implantable medical device at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and attention-warranting-titration patients exhibiting stimulation amplitude change behavior deviating from a stimulation amplitude change reference.

Example B13. The computer-readable storage medium of example B1, wherein the patient data comprises objective and subjective patient data, and the objective patient data comprises at least one of: stimulation therapy activity reported from an implantable medical device associated with each respective one of the plurality of patients; or physiologic information reported from an implantable medical device associated with each respective one of the plurality of patients.

Example B14. The computer-readable storage medium of example B1, wherein the patient data is associated each respective patient of the plurality of patients as received from a plurality of sources selected from: an implantable medical device; a patient communication device; and clinician input to the clinician portal.

Example B15. The computer-readable storage medium of example B14, wherein the patient communication device comprises at least one of: a dedicated patient remote control; or a consumer electronic device.

Example B16. The computer-readable storage medium of example B15, wherein the patient data comprises objective and subjective patient data, and the patient remote control is in communication with, and is to at least receive the objective patient data from, the implantable medical device and the consumer electronic device is in communication with, and is to at least receive the objective patient data, from the patient remote control.

Example B17. The computer-readable storage medium of example B1, further comprising instructions that when executed, cause the processing resource to: based on the patient data for a patient of the plurality of patients, perform patient care by determining, within the clinician portal, a stimulation therapy to be delivered to upper airway patency-related tissue to treat sleep disordered breathing.

Example B18. The computer-readable storage medium of example B17, further comprising instructions that when executed, cause the processing resource to send a signal to a stimulation element to cause delivery of a stimulation signal to the upper airway patency-related tissue.

Example B19. The computer-readable storage medium of example B17, further comprising instructions that when executed, cause the processing resource to communicate the determined stimulation therapy to an implantable medical device of the patient via at least one of: a dedicated patient remote control; or a consumer electronic device.

Example B20. The computer-readable storage medium of example B1, further comprising instructions that when executed, cause the processing resource to, based on the patient data, perform patient care by determining at least one patient management action and communicating the at least one patient management action to a patient communication device.

Example B21. The computer-readable storage medium of example B20, wherein the at least one patient management action comprises at least one of: scheduling a patient office visit; implementing at least one of a communication or a command to adjust parameters of stimulation therapy; implementing at least one of a communication or a command to adjust parameters of sensing; or implementing at least one of a communication or a command to adjust parameters of external patient monitoring.

Example B22. The computer-readable storage medium of example B1, wherein the different classes of the plurality of patients comprise patients with implantable medical devices that are categorized as: non-compliant patients; and compliant patients.

Example B23. The computer-readable storage medium of example B1, wherein the different classes of the plurality of patients comprise a plurality of classes of non-compliant patients with implantable medical devices, wherein the plurality of classes of non-compliant patients comprise: under-utilizing patients which utilize the implantable medical devices at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and/or attention-warranting-titration patients exhibiting stimulation amplitude change behavior deviating from a stimulation amplitude change reference.

Example B24. The computer-readable storage medium of example B1, wherein the patient data comprises objective and subjective patient data, and further comprising instructions that when executed, cause the processing resource to: receive the objective patient data from patient communication devices, the objective patient data comprising at least one of sensed physiologic information or externally monitored information including: implantable medical device usage; cardiac information; respiratory information; chest motion; oxygen desaturation information; peripheral arterial information; blood pressure; body position; acoustic information including snoring; sleep information including at least one of time spent in bed, total sleep time, start time, stop time, and a sleep stage(s); and/or sleep disordered breathing (SDB)-related index information.

Example B25. The computer-readable storage medium of example B1, wherein the patient data comprises objective and subjective patient data, and further comprising instructions that when executed, cause the processing resource to receive the subjective patient data from patient communication devices, the subjective patient data comprising patient survey information including at least one of: implantable medical device usage; comfort levels; usage hindrances; device visible indicators; snoring levels; or energy levels.

Example B26. The computer-readable storage medium of example B1, wherein the patient data further comprises patient management information input to the clinician portal via clinician input to at least one of the plurality of GUI portions.

Example B27. The computer-readable storage medium of example B1, further comprising instructions that when executed, cause the processing resource to represent respective ones of the plurality of GUI portions on other ones of the plurality of GUI portions via a corresponding icon, each of which is user selectable to cause transitions between respective ones of the GUI portions.

Example B28. The computer-readable storage medium of example B1, further comprising instructions that when executed, cause the processing resource to automatically present information which visually identifies non-compliant patients of the plurality of patients based on the at least one filter and an input field for clinician input via at least a portion of the plurality of GUI portions.

Example B29. The computer-readable storage medium of example B28, further comprising instructions that when executed, cause the processing resource to automatically output data to at least one patient communication device in response to clinician input to the input field to drive patient compliance.

Example B30. The computer-readable storage medium of example B1, wherein at least a subset of the plurality of GUI portions automatically present visual identification of non-compliant patients of the plurality of patients based on the at least one filter to cause at least one of improve patient compliance, prevent patient non-compliance, or mitigate further patient non-compliance.

Example B31. The computer-readable storage medium of example B1, wherein at least a subset of the plurality of GUI portions are patient specific and are selectable from at least another subset of the plurality of GUI portions which visually identify the plurality of patients.

Example B32. The computer-readable storage medium of example B31, further comprising instructions that when executed, cause the processing resource to: identify a patient of the plurality of patients based on at least one of the at least one filter and in at least one of the plurality of GUI portions; and receive a clinician input to the at least one of the plurality of GUI portions associated with the patient; and in response, output a communication to a patient communication device of the patient.

Example B33. The computer-readable storage medium of example B32, wherein the communication is provided at least one: prior to the patient being classified as non-compliant; and in response to the patient being classified as non-compliant based on the at least one filter.

Example BB1. A system comprising: the computer-readable storage medium of any of examples B1-B33 and a stimulation element configured to deliver a stimulation signal to a patient among the plurality of patients in response to a signal from the processing resource for treating the patient.

Example BB2. The system of example BB1, comprising instructions that when executed, cause the processing resource to send the signal to the stimulation element in response to clinician input received.

Example C1. A system comprising: at least one memory to store instructions and patient data for a plurality of patients; and at least one processing resource configured to execute the instructions to: provide a clinician portal to a clinician communication device, the clinician portal including a plurality of GUI portions that are individually and selectively displayable to present the patient data for the plurality of patients based on at least one filter for different classes of the plurality of patient; and receive the patient data from a plurality of patient communication devices and the clinical communication device.

Example C2. The system of example C1, further comprising a stimulation element configured to provide a stimulation signal to a patent among the plurality of patients in response to a signal from the processing resource, wherein the processing resource configured to execute the instructions to send the signal to the stimulation element responsive to clinician input.

Example C3. The system of example C1, wherein the patient data comprises objective patient data at least indicative of stimulation therapy activity and subjective patient data indicative of patient feedback, and the processing resource is configured to execute the instructions to present the GUI displaying at least one of the plurality of GUI portions populated using at least portions of the objective patient data juxtaposed with at least portions of the subjective patient data for the plurality of patients.

Example C4. The system of example C1, wherein the processing resource is configured to execute the instructions to: receive the patient data for a plurality of patients, the patient data comprising objective patient data indicative of patient feedback, and present the GUI by displaying selective ones of the plurality of GUI portions on the display screen.

Example C5. The system of claim C1, wherein the processing resource is configured to execute the instructions to: implement the clinician portal and to selectively integrate the patient data comprising objective patient data indicative of stimulation therapy activity and subjective patient data indicative of patient feedback; and present the plurality of GUI portions which are populated using at least a portion of the selectively integrated patient data.

Example C6. The system of example C1, wherein the processing resource is configured to execute the instructions to: based on the patient data and the different classes of the plurality of patients, present a visual identification of respective ones of the plurality of patients on at least one of the plurality of GUI portions as being at least one of non-compliant patients or predicted non-compliant patients based on the at least one filter.

Example C7. The system of example C1, wherein the processing resource is configured to execute the instructions to display the plurality of GUI portions with expanded features visually displayed on the display screen to manage the plurality of patients by exception based on a non-compliant criteria associated with the at least one filter.

Example C8. The system of example C1, wherein the plurality of GUI portions include a main GUI display which automatically presents a plurality of different non-compliance classes for each of the plurality of patients and a degree of each of the different non-compliance classes based on the at least one filter and as juxtaposed together, wherein areas of the main GUI display are selectable to transition to other respective ones of the GUI portions that expand on respective features.

Example C9. The system of example C8, wherein the different non-compliance classes include: under-utilizing patients which utilize an implantable medical device at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and attention-warranting-titration patients exhibiting stimulation amplitude change behavior deviating from a stimulation amplitude change reference.

Example C10. The system of example C1, wherein the processing resource is configured to execute the instructions to based on the patient data for a patient of the plurality of patients, perform patient care by determining, within the clinician portal, a stimulation therapy to be delivered to upper airway patency-related tissue to treat sleep disordered breathing.

Example D1. A method comprising: presenting, via a processing resource, a graphic user interface (GUI) associated with a clinician portal including a plurality of GUI portions that are individually and selectively displayable to present patient data for a plurality of patients based on at least one filter for different classes of the plurality of patients.

Example D2. The method of example D1, wherein the patient data comprises objective patient data at least indicative of stimulation therapy activity and subjective patient data indicative of patient feedback and presenting the GUI includes displaying at least one of the plurality of GUI portions which is populated using at least portions of the objective patient data juxtaposed with at least portions of the subjective patient data for the plurality of the patients.

Example D3. The method of example D1, further comprising: receiving, using the processing resource, the patient data for the plurality of patients, the patient data comprising objective patient data at least indicative of stimulation therapy activity and subjective patient data indicative of patient feedback; and presenting the GUI by displaying selective ones of the plurality of GUI portions on a display screen of a clinician-controlled device.:

Example D4. The method of example D1, further comprising integrating the patient data, wherein the patient data comprises objective patient data at least indicative of stimulation therapy activity and subjective patient data indicative of patient feedback and presenting the plurality of GUI portions which are populated using at least a portion of the integrated patient data.

Example D5. The method of example D1, further comprising: based on the patient data and the different classes of the plurality of patients, presenting a visual identification of respective ones of the plurality of patients on at least one of the plurality of GUI portions as being at least one of non-compliant patients or predicted non-compliant patients based on the at least one filter.

Example D6. The method of example D1, wherein the plurality of GUI portions are displayed to expand features visually displayed on a display screen to manage the plurality of patients by exception based on a non-compliant criteria associated with the at least one filter.

Example D7. The method of example D1, wherein the plurality of GUI portions include a main GUI display which automatically presents a plurality of different non-compliance classes for each of the plurality of patients and a degree of each of the different non-compliance classes based on the at least one filter and as juxtaposed together, wherein areas of the main GUI display are selectable to transition to other respective ones of the GUI portions that expand on respective features.

Example D8. The method of example D7, wherein the different non-compliance classes include: under-utilizing patients which utilize an implantable medical device at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and attention-warranting-titration patients exhibiting stimulation amplitude change behavior deviating from a stimulation amplitude change reference.

Example D9. The method of example D1, wherein the patient data comprises objective and subjective patient data, and the objective patient data comprises stimulation therapy activity reported from an implantable medical device associated with each respective one of the plurality of patients.

Example D10. The method of example D1, wherein the patient data comprises objective and subjective patient data, and the objective patient data comprises physiologic information reported from an implantable medical device associated with each respective one of the plurality of patients.

Example D11. The method of example D1, comprising: receiving the patient data for each respective patient of the plurality of patients from a plurality of sources selected from: an implantable medical device; a patient communication device; and clinician input to the clinician portal.

Example D12. The method of example D11, wherein the patient communication device comprises at least one of: a dedicated patient remote control; or a consumer electronic device.

Example D13. The method of example D12, wherein the patient data comprises objective and subjective patient data, and the patient remote control is in communication with, and is to at least receive the objective patient data from, the implantable medical device and the consumer electronic device is in communication with, and is to at least receive the objective patient data, from the patient remote control.

Example D14. The method of example D1, further comprising: based on the patient data for a patient of the plurality of patients, performing patient care by determining, within the clinician portal and via a clinician-controlled device, a stimulation therapy to be delivered to upper airway patency-related tissue to treat sleep disordered breathing.

Example D15. The method of example D14, comprising: communicating the determined stimulation therapy from the clinician-controlled device in communication with clinician portal or the processing resource implementing the clinician portal to an implantable medical device of the patient via at least one of: a clinician-controlled communication device; a dedicated patient remote control; a consumer electronic device; or the processing resource.

Example D16. The method of claim example D1, further comprising: based on the patient data, performing patient care by determining at least one patient management action and communicating the at least one patient management action to a patient communication device.

Example D17. The method of example D16, wherein the at least one patient management action comprises at least one of: scheduling a patient office visit; implementing at least one of a communication or a command to adjust parameters of stimulation therapy; implementing at least one of a communication or a command to adjust parameters of sensing; or implementing at least one of a communication or a command to adjust parameters of external patient monitoring.

Example D18. The method of example D1, wherein the different classes of the plurality of patients comprise patients with implantable medical devices that are categorized as: non-compliant patients; and compliant patients.

Example D19. The method of example D1, wherein the different classes of the plurality of patients comprise a plurality of classes of non-compliant patients with implantable medical devices.

Example D20. The method of example D19, wherein the plurality of classes of non-compliant patients comprise: under-utilizing patients which utilize the implantable medical devices at a rate less than a threshold; under-surveying patients which complete a patient survey outside a threshold time period; under-updating patients which provide a therapy-related update status outside a threshold time period; attention-warranting-answer patients which provide an answer to a patient survey that is indicative of an issue; and/or attention-warranting-titration patients exhibiting stimulation amplitude change behavior deviating from a stimulation amplitude change reference.

Example D21. The method of example D1, wherein the patient data comprises objective and subjective patient data, the method further comprising: receiving the objective patient data from patient communication devices, the objective patient data comprising at least one of sensed physiologic information or externally monitored information including at least one of: implantable medical device usage; cardiac information; respiratory information; chest motion; oxygen desaturation information; peripheral arterial information; blood pressure; body position; acoustic information including snoring; sleep information including at least one of time spent in bed, total sleep time, start time, stop time, or sleep stage(s); and sleep disordered breathing (SDB)-related index information.

Example D22. The method of example D1, wherein the patient data comprises objective and subjective patient data, the method further comprising receiving the subjective patient data from patient communication devices, the subjective patient data comprising patient survey information including at least one of: implantable medical device usage; comfort levels; usage hindrances; device visible indicators; snoring levels; or energy levels.

Example D23. The method of example D1, wherein the patient data further comprises patient management information input to the clinician portal via clinician input to at least one of the plurality of GUI portions.

Example D24. The method of example D1, comprising: representing respective ones of the plurality of GUI portions on other ones of the plurality of GUI portions via a corresponding icon, each of which is user selectable to cause transitions between respective ones of the GUI portions.

Example D25 . . . . The method of example D1, further comprising automatically presenting information which visually identifies non-compliant patients of the plurality of patients based on the at least one filter and an input field for clinician input via at least a portion of the plurality of GUI portions.

Example D26. The method of example D25, further comprising automatically outputting data to at least one patient communication device in response to clinician input to the input field to drive patient compliance.

Example D27. The method of example D1, wherein at least a subset of the plurality of GUI portions automatically present visual identification of non-compliant patients of the plurality of patients based on the at least one filter to cause at least one of improving patient compliance, preventing patient non-compliance, or mitigating further patient non-compliance.

Example D28. The method of example D1, wherein at least a subset of the plurality of GUI portions are patient specific and are selectable from at least another subset of the plurality of GUI portions which visually identify the plurality of patients.

Example D29. The method of example D28, further comprising; identifying a patient of the plurality of patients based on at least one of the at least one filter and in at least one of the plurality of GUI portions; and receiving a clinician input to the at least one of the plurality of GUI portions associated with the patient; and in response, outputting, via the processing resource, a communication to a patient communication device of the patient.

Example D30. The method of example D29, wherein the communication is provided prior to the patient being classified as non-compliant or in response to the patient being classified as non-compliant based on the at least one filter.

The invention claimed is:

1. A non-transitory computer-readable storage medium comprising instructions that when executed cause a processing resource to:

present a graphical user interface (GUI) associated with a clinician portal, the GUI including a plurality of GUI portions that are individually and selectively displayable to present patient data for a plurality of patients based on filters for different classes of the plurality of patients, the different classes of the plurality of patients comprising a plurality of classes of non-compliant patients having implantable medical devices and the patient data comprising objective patient data indicative of stimulation therapy activity applied by the implantable medical devices to the plurality of patients.

2. The computer-readable storage medium of claim 1, wherein the GUI is presented on a display screen, and wherein the objective patient data indicative of stimulation therapy activity applied by the implantable medical devices comprises average rates of use of the implantable medical devices or stimulation amplitude changes for the stimulation therapy activity applied by the implantable medical devices.

3. The computer-readable storage medium of claim 1, wherein the different classes of the plurality of patients further comprises a class of compliant patients having implantable medical devices, wherein the patient data further comprises subjective patient data indicative of patient feedback, and further comprising instructions that when executed, cause the processing resource to:

present the GUI displaying at least one of the plurality of GUI portions populated using at least portions of the objective patient data juxtaposed with at least portions of the subjective patient data for the plurality of patients, the plurality of GUI portions including visual identification of respective ones of the patients that are categorized as at least one of the plurality of classes of non-compliant patients having implantable medical device based on the filters for the different classes of patients.

4. The computer-readable storage medium of claim 1, further comprising instructions that when executed, cause the processing resource to:

receive the patient data for the plurality of patients, the patient data further comprising objective patient data indicative of patient feedback, and present the GUI by displaying selective ones of the plurality of GUI portions on a display screen; and in response to user selection of a filter icon on the GUI associated with one filter of the filters, present a revised GUI by:

displaying respective patient data for respective patients which are non-compliant with a criteria associated with the one filter, and are thereby classified as one of the plurality of classes of non-compliant patients, and not displaying patient data for the remaining patients which are compliant with the criteria associated with the one filter.

5. The computer-readable storage medium of claim 1, further comprising instructions that when executed, cause the processing resource to:

categorize each of plurality of patients as at least one of the different classes based on the filters, wherein respective ones of the plurality of patients are categorized as at least one of the plurality of classes of non-compliant patients having implantable medical devices based on the filters and at least one of the filters comprises a criteria associated with a stimulation amplitude change of the stimulation therapy activity applied by the implantable medical devices that differs from a reference;

implement the clinician portal and to selectively integrate the patient data comprising the objective patient data indicative of stimulation therapy activity and subjective patient data indicative of patient feedback; and in response, present the plurality of GUI portions which are populated using at least a portion of the selectively integrated patient data and based on the categorization.

6. The computer-readable storage medium of claim 1, further comprising instructions that when executed, cause the processing resource:

based on the patient data and the different classes of the plurality of patients, present a visual identification of respective ones of the plurality of patients on at least one of the plurality of GUI portions as being at least one of non-compliant patients or predicted non-compliant patients based on at least one of the filters, wherein the objective patient data indicative of the stimulation therapy activity is associated with stimulation by the implantable medical devices to the plurality of patients for treatment of sleep disordered breathing.

7. The computer-readable storage medium of claim 1, further comprising instructions that when executed, cause the processing resource to display the plurality of GUI portions with expanded features visually displayed on a display screen to manage the plurality of patients by exception based on non-compliant criteria associated with the filters.

8. The computer-readable storage medium of claim 1, wherein the plurality of GUI portions include a main GUI display which automatically presents the plurality of classes of non-compliant patients for each of the plurality of patients and a degree of each of the classes of non-compliant patients based on the filters and as juxtaposed together, wherein areas of the main GUI display are selectable to transition to other respective ones of the GUI portions that expand on respective features.

9. The computer-readable storage medium of claim 8, wherein the plurality of classes of non-compliant patients include:

under-utilizing patients which utilize an implantable medical device at a rate less than a threshold;

under-surveying patients which complete a patient survey outside a threshold time period;

under-updating patients which provide a therapy-related update status outside a threshold time period;

attention-warranting-answer patients which provide an answer to a patient survey that is indicative of an issue; and attention-warranting-titration patients exhibiting stimulation amplitude change behavior deviating from a stimulation amplitude change reference.

10. The computer-readable storage medium of claim 1, wherein the patient data comprises the objective patient data and subjective patient data, and the objective patient data comprises:

the applied stimulation therapy activity reported from the implantable medical devices as associated with each respective one of the plurality of patients; and physiologic information reported from the implantable medical devices as associated with each respective one of the plurality of patients.

11. The computer-readable storage medium of claim 1, wherein the patient data is associated each respective patient of the plurality of patients as received from a plurality of sources selected from:

the implantable medical devices;

patient communication devices; and clinician input to the clinician portal, wherein each of the patient communication devices comprise at least one of:

a dedicated patient remote control; or a consumer electronic device.

12. The computer-readable storage medium of claim 11, wherein the patient data comprises the objective patient data and subjective patient data, and the patient remote controls are in communication with, and are to at least receive the objective patient data from, the implantable medical devices and the consumer electronic devices are in communication with, and are to at least receive the objective patient data, from the patient remote controls, wherein the objective patient data indicative of stimulation therapy activity applied by the implantable medical devices comprises average rates of use of the implantable medical devices and stimulation amplitude changes for the stimulation therapy activity applied by the implantable medical devices.

13. The computer-readable storage medium of claim 1, further comprising instructions that when executed, cause the processing resource to:

based on the patient data for a patient of the plurality of patients, perform patient care by determining, within the clinician portal, a stimulation therapy to be delivered to upper airway patency-related tissue by a respective implantable medical device of the implantable medical devices to treat sleep disordered breathing.

14. The computer-readable storage medium of claim 13, further comprising instructions that when executed, cause the processing resource to send a signal to a stimulation element to cause delivery of a stimulation signal to the upper airway patency-related tissue.

15. The computer-readable storage medium of claim 13, further comprising instructions that when executed, cause the processing resource to communicate the stimulation therapy to the implantable medical device of the patient via at least one of:

a dedicated patient remote control; or a consumer electronic device.

16. The computer-readable storage medium of claim 1, further comprising instructions that when executed, cause the processing resource to, based on the patient data, perform patient care by determining at least one patient management action and communicating the at least one patient management action to a patient communication device.

17. The computer-readable storage medium of claim 16, wherein the at least one patient management action comprises at least one of:

scheduling a patient office visit;

implementing at least one of a communication or a command to adjust parameters of stimulation therapy;

implementing at least one of a communication or a command to adjust parameters of sensing; or implementing at least one of a communication or a command to adjust parameters of external patient monitoring.

18. The computer-readable storage medium of claim 1, wherein the plurality of classes of non-compliant patients comprise at least two of:

under-utilizing patients which utilize the implantable medical devices at a rate less than a threshold;

under-surveying patients which complete a patient survey outside a threshold time period;

under-updating patients which provide a therapy-related update status outside a threshold time period;

attention-warranting-answer patients which provide an answer to a patient survey that is indicative of an issue; and attention-warranting-titration patients exhibiting stimulation amplitude change behavior of a respective implantable medical device of the implantable medical devices deviating from a stimulation amplitude change reference.

19. The computer-readable storage medium of claim 1, wherein the patient data comprises the objective patient data and subjective patient data, and further comprising instructions that when executed, cause the processing resource to:

receive the objective patient data from patient communication devices, the objective patient data comprising implantable medical device usage and at least one of sensed physiologic information or externally monitored information including at least one of:

cardiac information;

respiratory information;

chest motion;

oxygen desaturation information;

peripheral arterial information;

blood pressure;

body position;

acoustic information including snoring;

sleep information including at least one of time spent in bed, total sleep time, start time, stop time, or a sleep stage; or sleep disordered breathing (SDB)-related index information.

20. The computer-readable storage medium of claim 1, wherein the patient data comprises the objective patient data and subjective patient data, and further comprising instructions that when executed, cause the processing resource to receive the subjective patient data from patient communication devices, the subjective patient data comprising patient survey information including at least one of:

implantable medical device usage;

comfort levels;

usage hindrances;

device visible indicators;

snoring levels; or energy levels.

* * * * *